(12) United States Patent
Pelcman et al.

(10) Patent No.: US 11,648,216 B2
(45) Date of Patent: May 16, 2023

(54) FLUOROPHENYL BETA-HYDROXYETHYLAMINES AND THEIR USE IN THE TREATMENT OF HYPERGLYCAEMIA

(71) Applicant: ATROGI AB, Stockholm (SE)

(72) Inventors: Benjamin Pelcman, Stockholm (SE); Tore Bengtsson, Vaxholm (SE)

(73) Assignee: ATROGI AB, Stockholm (SE)

( * ) Notice: Subject to any disclaimer, the term of this patent is extended or adjusted under 35 U.S.C. 154(b) by 218 days.

(21) Appl. No.: 16/646,497

(22) PCT Filed: Sep. 13, 2018

(86) PCT No.: PCT/GB2018/052594
§ 371 (c)(1),
(2) Date: Mar. 11, 2020

(87) PCT Pub. No.: WO2019/053426
PCT Pub. Date: Mar. 21, 2019

(65) Prior Publication Data
US 2020/0268688 A1 Aug. 27, 2020

(30) Foreign Application Priority Data
Sep. 13, 2017 (GB) ...................................... 1714734

(51) Int. Cl.
| | | |
|---|---|---|
| *A61K 31/137* | (2006.01) | |
| *A61K 31/167* | (2006.01) | |
| *A61K 45/06* | (2006.01) | |
| *A61P 3/10* | (2006.01) | |
| *C07C 215/30* | (2006.01) | |
| *C07C 215/34* | (2006.01) | |
| *C07C 215/42* | (2006.01) | |
| *C07C 215/68* | (2006.01) | |
| *C07C 215/60* | (2006.01) | |
| *C07C 233/43* | (2006.01) | |

(52) U.S. Cl.
CPC .......... *A61K 31/137* (2013.01); *A61K 31/167* (2013.01); *A61P 3/10* (2018.01); *C07C 215/34* (2013.01); *C07C 215/42* (2013.01); *C07C 215/68* (2013.01); *C07C 233/43* (2013.01)

(58) Field of Classification Search
CPC .... A61K 31/137; A61K 31/167; A61K 45/06; A61K 2300/00; A61P 3/10; C07B 2200/07; C07C 215/30; C07C 215/34; C07C 215/42; C07C 215/68; C07C 215/60; C07C 233/43; C07C 2601/02; C07C 2601/04
See application file for complete search history.

(56) References Cited

U.S. PATENT DOCUMENTS

| | | |
|---|---|---|
| 2,308,232 A | 1/1943 | Scheuing et al. |
| 2,460,144 A | 1/1949 | Moore |
| 3,056,836 A | 10/1962 | Hendrik |
| 3,341,594 A | 9/1967 | Otto et al. |
| 3,410,944 A | 11/1968 | Claassen et al. |
| 3,801,631 A | 4/1974 | Comer et al. |
| 3,910,934 A | 10/1975 | Sankey et al. |
| 3,952,101 A | 4/1976 | Jen et al. |
| 3,954,871 A | 5/1976 | Buu-Hoi et al. |
| 3,985,887 A | 10/1976 | Kaiser et al. |
| 4,024,156 A | 5/1977 | Bagli et al. |
| 4,119,710 A | 10/1978 | Engelhardt et al. |
| 4,223,137 A | 9/1980 | Yoshizaki et al. |
| 4,244,967 A | 1/1981 | Engelhardt et al. |
| 4,248,884 A | 2/1981 | Legrand et al. |
| 4,743,604 A | 5/1988 | Alig et al. |
| 4,835,315 A | 5/1989 | Lafon |
| 4,863,959 A | 9/1989 | Bentley et al. |
| 4,927,836 A | 5/1990 | Holloway et al. |
| 5,019,578 A | 5/1991 | Fisher et al. |
| 5,061,727 A | 10/1991 | Bloom et al. |
| 5,705,515 A | 1/1998 | Fisher et al. |
| 6,346,532 B1 | 2/2002 | Maruyama et al. |
| 6,403,612 B2 | 6/2002 | Nantermet et al. |
| 7,795,310 B2 | 9/2010 | Lee et al. |
| 9,657,348 B2 | 5/2017 | Bengtsson |
| 9,784,726 B2 | 10/2017 | Bengtsson |
| 9,891,212 B2 | 2/2018 | Bengtsson |

(Continued)

FOREIGN PATENT DOCUMENTS

| | | |
|---|---|---|
| AT | 285583 B | 11/1970 |
| BE | 823841 A | 4/1975 |

(Continued)

OTHER PUBLICATIONS

Lands, 1952, Journal of Pharmacology and Experimental Therapeutics, 106, 440-443.*

(Continued)

*Primary Examiner* — Sun Jae Yoo

(74) *Attorney, Agent, or Firm* — McCarter & English, LLP; Steven G. Davis; Michael J. DeGrazia

(57) ABSTRACT

There is herein provided a compound of formula (I).

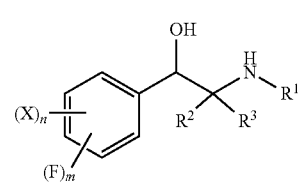

5 Claims, No Drawings

(56) References Cited

U.S. PATENT DOCUMENTS

| | | |
|---|---|---|
| 10,288,602 B2 | 5/2019 | Bengtsson |
| 11,357,757 B2 | 6/2022 | Pelcman et al. |
| 2001/0044454 A1 | 11/2001 | Nantermet et al. |
| 2003/0018061 A1 | 1/2003 | Ogawa et al. |
| 2004/0105819 A1 | 6/2004 | Hale et al. |
| 2004/0266867 A1 | 12/2004 | Cheng et al. |
| 2005/0250944 A1 | 11/2005 | Chen |
| 2006/0223886 A1 | 10/2006 | Dargazanli et al. |
| 2008/0306160 A1 | 12/2008 | Kobayashi et al. |
| 2009/0181976 A1 | 7/2009 | Buschmann et al. |
| 2010/0022658 A1 | 1/2010 | Epstein et al. |
| 2010/0022659 A1 | 1/2010 | Meyerson et al. |
| 2010/0173928 A1 | 7/2010 | Sabatini et al. |
| 2011/0306552 A1 | 12/2011 | Rao et al. |
| 2013/0331433 A1 | 12/2013 | Thibonnier |
| 2017/0153225 A1 | 6/2017 | Bengtsson |
| 2019/0119196 A1 | 4/2019 | Pelcman et al. |
| 2019/0314301 A1 | 10/2019 | Pelcman et al. |
| 2020/0268687 A1 | 8/2020 | Pelcman et al. |
| 2020/0277259 A1 | 9/2020 | Pelcman et al. |
| 2020/0315993 A1 | 10/2020 | Pelcman et al. |
| 2021/0030731 A1 | 2/2021 | Pelcman et al. |
| 2021/0338603 A1 | 11/2021 | Pelcman et al. |
| 2022/0133703 A1 | 5/2022 | Pelcman et al. |
| 2022/0152004 A1 | 5/2022 | Pelcman et al. |
| 2022/0194920 A1 | 6/2022 | Pelcman et al. |

FOREIGN PATENT DOCUMENTS

| | | | |
|---|---|---|---|
| CN | 103565784 | A | 2/2014 |
| CN | 105078946 | A | 11/2015 |
| CN | 106083837 | A | 11/2016 |
| DE | 638650 | C | 11/1936 |
| DE | 45721 | A | 11/1966 |
| DE | 2015573 | A1 | 10/1970 |
| DE | 2128258 | A1 | 12/1971 |
| DE | 2157040 | A1 | 5/1973 |
| DE | 2212600 | A1 | 9/1973 |
| DE | 2259282 | A1 | 6/1974 |
| DE | 2300614 | A1 | 7/1974 |
| DE | 2413102 | A1 | 10/1975 |
| DE | 2548053 | A1 | 5/1976 |
| DE | 2700193 | A1 | 7/1977 |
| DE | 2819458 | A1 | 11/1978 |
| DE | 4209989 | A1 | 10/1992 |
| EP | 0023385 | A1 | 2/1981 |
| EP | 0043807 | A2 | 1/1982 |
| EP | 0128120 | A2 | 12/1984 |
| EP | 0195396 | A1 | 9/1986 |
| EP | 0224001 | A1 | 6/1987 |
| EP | 0272976 | A2 | 6/1988 |
| EP | 0290122 | A1 | 11/1988 |
| EP | 0303546 | A2 | 2/1989 |
| EP | 0357956 | A2 | 3/1990 |
| EP | 0436435 | A1 | 7/1991 |
| EP | 0543662 | A2 | 5/1993 |
| EP | 0611003 | A1 | 8/1994 |
| EP | 0659737 | A2 | 6/1995 |
| EP | 1095932 | A1 | 5/2001 |
| EP | 1277736 | A1 | 1/2003 |
| EP | 1829534 | A1 | 9/2007 |
| EP | 2426202 | A1 | 3/2012 |
| FR | 1324914 | A | 4/1963 |
| FR | 2647310 | A1 | 11/1990 |
| GB | 1142508 | A | 2/1969 |
| GB | 1199630 | A | 7/1970 |
| GB | 1517934 | A | 7/1978 |
| GB | 2054581 | A | 2/1981 |
| GB | 2133986 | A | 8/1984 |
| GB | 2151612 | A | 7/1985 |
| JP | 49-094640 | A | 9/1974 |
| JP | 50-100065 | A | 8/1975 |
| JP | 51-122073 | A | 10/1976 |
| JP | 52-105138 | A | 9/1977 |
| JP | 54-001693 | A | 1/1979 |
| JP | 55-038375 | A | 3/1980 |
| JP | 55-45688 | A | 3/1980 |
| JP | S56055355 | A | 5/1981 |
| JP | 57-169450 | A | 10/1982 |
| JP | 61-251621 | A | 11/1986 |
| JP | 64-42468 | A | 2/1989 |
| JP | H08-239349 | A | 9/1996 |
| JP | 2005-097149 | A | 4/2005 |
| JP | 2007-217368 | A | 8/2007 |
| JP | 2008-505176 | A | 2/2008 |
| JP | 2008-505956 | A | 2/2008 |
| JP | 2009-502733 | A | 1/2009 |
| JP | 2009-510067 | A | 3/2009 |
| JP | 2010-530402 | A | 9/2010 |
| JP | 2013-522302 | A | 6/2013 |
| JP | 7046842 | B2 | 4/2022 |
| NL | 7804582 | A | 11/1978 |
| RU | 2095344 | C1 | 11/1997 |
| WO | WO-1991/09596 | A1 | 7/1991 |
| WO | WO-1993/15041 | A1 | 8/1993 |
| WO | WO-1996/04234 | A1 | 2/1996 |
| WO | WO-1997/25311 | A1 | 7/1997 |
| WO | WO-1998/22480 | A1 | 5/1998 |
| WO | WO-1998/32753 | A1 | 7/1998 |
| WO | WO-1999/20607 | A1 | 4/1999 |
| WO | WO-1999/35279 | A1 | 7/1999 |
| WO | WO-1999/43326 | A1 | 9/1999 |
| WO | 1999/65311 | A1 | 12/1999 |
| WO | WO-1999/65308 | A1 | 12/1999 |
| WO | WO-1999/65877 | A1 | 12/1999 |
| WO | WO-2000/075114 | A1 | 12/2000 |
| WO | WO-2001/74782 | A1 | 10/2001 |
| WO | WO-2002/032897 | A1 | 4/2002 |
| WO | WO-2003/032969 | A2 | 4/2003 |
| WO | 2003/101958 | A2 | 12/2003 |
| WO | WO-2004/004451 | A1 | 1/2004 |
| WO | 2004/022566 | A1 | 3/2004 |
| WO | WO-2004/071388 | A2 | 8/2004 |
| WO | WO-2004/110375 | A2 | 12/2004 |
| WO | WO-2005/013666 | A2 | 2/2005 |
| WO | WO-2005/025570 | A1 | 3/2005 |
| WO | 2005/037781 | A2 | 4/2005 |
| WO | 2005/075458 | A1 | 8/2005 |
| WO | 2005/108381 | A1 | 11/2005 |
| WO | 2005/111002 | A2 | 11/2005 |
| WO | WO-2005/102350 | A1 | 11/2005 |
| WO | WO-2005/110990 | A1 | 11/2005 |
| WO | WO-2005/114195 | A1 | 12/2005 |
| WO | 2006/04803 | A1 | 1/2006 |
| WO | 2006/005551 | A1 | 1/2006 |
| WO | WO-2006/027579 | A2 | 3/2006 |
| WO | WO-2006/122788 | A1 | 11/2006 |
| WO | 2007/011065 | A1 | 1/2007 |
| WO | 2007/026630 | A1 | 3/2007 |
| WO | WO-2007/102011 | A1 | 9/2007 |
| WO | 2007/109882 | A1 | 10/2007 |
| WO | 2008/011453 | A2 | 1/2008 |
| WO | WO-2008/022038 | A1 | 2/2008 |
| WO | 2008/071948 | A2 | 6/2008 |
| WO | 2009/010660 | A2 | 1/2009 |
| WO | WO-2009/124166 | A1 | 10/2009 |
| WO | WO-2009/124167 | A1 | 10/2009 |
| WO | WO-2009/156413 | A1 | 12/2009 |
| WO | 2010/16939 | A1 | 2/2010 |
| WO | 2011/037815 | A1 | 3/2011 |
| WO | WO-2011/025960 | A1 | 3/2011 |
| WO | WO-2011/112867 | A1 | 9/2011 |
| WO | 2012/064269 | A1 | 5/2012 |
| WO | 2014/108449 | A1 | 7/2014 |
| WO | WO-2018/011588 | A1 | 1/2018 |
| WO | 2019/053425 | A1 | 3/2019 |
| ZA | 8703195 | | 10/1987 |

OTHER PUBLICATIONS

RN920800-46-0, 2007, registry database compound.*
CAS RN 2155248-91-0. Chemcats entry date: Jan. 15, 2019. 1 page.
CAS RN 2274711-69-0. Chemcats entry date: Jan. 15, 2019. 1 page.

(56) References Cited

OTHER PUBLICATIONS

CAS RN 2278127-42-5. Chemcats entry date: Jan. 15, 2019. 1 page.
CAS RN 2287791-82-4. Chemcats entry date: Jan. 15, 2019. 1 page.
CAS RN 2289315-62-2. Chemcats entry date: Jan. 15, 2019. 1 page.
Brittain et al., Sympathomimetic bronchodilator drugs. Pharmacol Ther B. 1976;2(3):423-462.
Cioc et al., One-Pot Synthesis of N-Substituted beta-Amino Alcohols from Aldehydes and Isocyanides. Chemistry. 2015;21(21):7808-7813. Including supporting information.
Ning et al., A new, one-step synthesis of 1-heteroaryl-2-alkylaminoethanols. Tetrahedron Letters. 2010;51:843-845.
Allen et al., Studies on the inhibition of glucose metabolism in isolated fat cells by beta-adrenergic blocking agents. Biochem Pharmacol. Jun. 1969;18(6):1347-54.
Bercher et al., Wirkung fluorierter Phenyläthanolamine auf eine durch Katecholamine induzierte Hyperglykämie bei Ratten [The effect of fluoridated phenylethanolamines on hyperglycemia induced by catecholamines in the rat]. Acta Biol Med Ger. 1975;34(4):667-74.
Cooperberg et al., Terbutaline and the prevention of nocturnal hypoglycemia in type 1 diabetes. Diabetes Care. Dec. 2008;31(12):2271-2.
Satoh, Glycemic effects of solanine in rats. Jpn J Pharmacol. Dec. 1967;17(4):652-8.
Star et al., Glucocorticoid-associated maternal hyperglycemia: a randomized trial of insulin prophylaxis. J Matern Fetal Med. Sep.-Oct. 2000;9(5):273-7.
Chen et al., Syntheses of 2,5- and 2,6-difluoronorepinephrine, 2,5-difluoroepinephrine, and 2,6-difluorophenylephrine: effect of disubstitution with fluorine on adrenergic activity. J Med Chem. Nov. 26, 1993;36(24):3947-55.
Lu et al., Syntheses of (R)- and (S)-2- and 6-fluoronorepinephrine and (R)- and (S)-2- and 6-fluoroepinephrine: effect of stereochemistry on fluorine-induced adrenergic selectivities. J Med Chem. Apr. 20, 2000;43(8):1611-9.
Luthy et al., Lead-oriented synthesis: Investigation of organolithium-mediated routes to 3-D scaffolds and 3-D shape analysis of a virtual lead-like library. Bioorg Med Chem. Jun. 1, 2015;23(11):2680-94.
McCarty et al., Central Stimulants. a,a-Disubstituted 2-Piperidinemethanols and 1,1-Disubstituted Heptahydrooxazolo [3,4-a]pyridines. J Am Chem Soc. 1957;79:472-480.
Sanner, Stereoselective condensations of a'-lithio pyrrolidine amidines. Tetrahedron Letters. 1989;30(15):1909-1912.
Ye et al., Dual catalysis for enantioselective convergent synthesis of enantiopure vicinal amino alcohols. Nat Commun. Jan. 29, 2018;9(1):410, 9 pages.
Ye et al., One-Pot Cascade Hydration-Asymmetric Transfer Hydrogenation as a Practical Strategy to Construct Chiral beta-Adrenergic Receptor Blockers. ChemCatChem. Jun. 15, 2015;7(12):1801-1805.
Ahren et al., Adrenergic innervation of pancreatic islets and modulation of insulin secretion by the sympatho-adrenal system. Cell Tissue Res. 1981;216(1):15-30.
Alessi et al., Characterization of a 3-phosphoinositide-dependent protein kinase which phosphorylates and activates protein kinase Balpha. Curr Biol. Apr. 1, 1997;7(4):261-9.
Arch et al., Prospects for beta3-adrenoceptor agonists in the treatment of obesity and diabetes. International Journal of Obesity. 1996;20:191-199.
Baker et al., Chronic treatment with the beta(2)-adrenoceptor agonist prodrug BRL-47672 impairs rat skeletal muscle function by inducing a comprehensive shift to a faster muscle phenotype. J Pharmacol Exp Ther. Oct. 2006;319(1):439-46.
Barnes et al., Activation of GLUT1 by metabolic and osmotic stress: potential involvement of AMP-activated protein kinase (AMPK). J Cell Sci. Jun. 1, 2002;115(Pt 11):2433-42.
Baur et al., The identification of indacaterol as an ultralong-acting inhaled beta2-adrenoceptor agonist. J Med Chem. May 13, 2010;53(9):3675-84.

Beak et al., alpha.-Lithioamine synthetic equivalents: syntheses of diastereoisomers from the Boc-piperidines. J Org Chem. Apr. 1, 1990;55(9):2578-2580.
Bentzinger et al., Skeletal muscle-specific ablation of raptor, but not of rictor, causes metabolic changes and results in muscle dystrophy. Cell Metab. Nov. 2008;8(5):411-24.
Biel et al., Bronchodilators, N-substituted derivatives of 1-(3',4'-Dihydroxyphenyl)-2-aminoethanol (Arterenol). J Am Chem Soc. Jun. 1954;76:3149-53.
Brown et al., A mammalian protein targeted by G1-arresting rapamycin-receptor complex. Nature. Jun. 30, 1994;369(6483):756-8.
Bryant et al., Regulated transport of the glucose transporter GLUT4. Nat Rev Mol Cell Biol. Apr. 2002;(4):267-77.
Cannon et al., Brown adipose tissue: function and physiological significance. Physiol Rev. Jan. 2004;84(1):277-359.
Carayannopoulos et al., GLUT8 is a glucose transporter responsible for insulin-stimulated glucose uptake in the blastocyst. Proc Natl Acad Sci USA. Jun. 20, 2000;97(13):7313-8.
Castle et al., Attenuation of insulin resistance by chronic beta2-adrenergic agonist treatment possible muscle specific contributions. Life Sci. Jun. 22, 2001;69(5):599-611.
Chandler et al., Expression and localization of GLUT1 and GLUT12 in prostate carcinoma. Cancer. Apr. 15, 2003;97(8):2035-42.
Chariot et al., Effects of CRL 40827 and salbutamol on exocrine pancreatic secretion in rats. Eur J. Pharmacol. Jan. 27, 1988;146(1):17-25.
Chernogubova et al., Alpha1- and beta1-adrenoceptor signaling fully compensates for beta3-adrenoceptor deficiency in brown adipocyte norepinephrine-stimulated glucose uptake. Endocrinology. May 2005;146(5):2271-84.
Chernogubova et al., Norepinephrine increases glucose transport in brown adipocytes via beta3-adrenoceptors through a cAMP, PKA, and PI3-kinase-dependent pathway stimulating conventional and novel PKCs. Endocrinology. Jan. 2004;145(1):269-80.
Conde et al., beta-Adrenoceptor blocking activity of halogenated thienylethanolamine derivatives. J Med Chem. Jul. 1977;20(7):970-4.
Copp et al., TORC-specific phosphorylation of mammalian target of rapamycin (mTOR): phospho-Ser2481 is a marker for intact mTOR signaling complex 2. Cancer Res. Mar. 1, 2009;69(5):1821-7.
Cypress et al., Activation of Human Brown Adipose Tissue by a beta3-Adrenergic Receptor Agonist. Cell Metab. Jan. 2015. 21(1):33-38.
Dallner et al., Beta3-adrenergic receptors stimulate glucose uptake in brown adipocytes by two mechanisms independently of glucose transporter 4 translocation. Endocrinology. Dec. 2006;147(12):5730-9.
De Souza et al., Beta 3-adrenoceptor agonists as anti-diabetic and anti-obesity drugs in humans. Curr Pharm Des. Sep. 2001;7(14):1433-49.
Defronzo et al., Synergistic Interaction between Exercise and Insulin on Peripheral Glucose Uptake. J Clin Invest. Dec. 1981;68:1468-74.
Dehvari et al., beta(2)-Adrenoceptors increase translocation of GLUT4 via GPCR kinase sites in the receptor C-terminal tail. Br J Pharmacol. Mar. 2012;165(5):1442-56.
Drake et al., Trafficking of G protein-coupled receptors. Circ Res. Sep. 15, 2006;99(6):570-82.
Edmondson et al., Discovery of Vibegron: A Potent and Selective B3 Adrenergic Receptor Agonist for the Treatment of Overactive Bladder. J Med Chem. Jan. 28, 2016;59(2):609-23.
Elayan et al., Chronic beta2 adrenergic agonist, but not exercise, improves glucose handling in older type 2 diabetic mice. Cell Mol Neurobiol. Jul. 2012;32(5):871-7.
Engelhardt, Structure activity relationship in a series of new aminohalogen substituted phenyl-aminoethanols. Arzneimittelforschung. May 1972;22(5):869-76.
Evans et al., beta2-Adrenoceptor-mediated regulation of glucose uptake in skeletal muscle—ligand-directed signalling or a reflection of system complexity? Naunyn Schmiedebergs Arch Pharmacol. Sep. 2013;386(9):757-60.

(56) References Cited

OTHER PUBLICATIONS

Evron et al., GRK2: multiple roles beyond G protein-coupled receptor desensitization. Trends Pharmacol Sci. Mar. 2012;33(3):154-64.
Exton, Mechanisms of hormonal regulation of hepatic glucose metabolism. Diabetes Metab Rev. Jan. 1987;3(1):163-83.
Feldman et al., Active-Site Inhibitors of mTOR Target Rapamycin-Resistant Outputs of mTORC1 and mTORC2. PLoS Biol. Feb. 10, 2009;7(2):e38. 13 pages.
Fisher et al., BMS-187257, a Potent, Selective, and Novel Heterocyclic beta3 Adrenergic Receptor Agonist. Bioorganic & Medicinal Chemistry Letters. 1996;6(19):2253-8.
Garcia-Martinez et al., Ku-0063794 is a specific inhibitor of the mammalian target of rapamycin (mTOR). Biochem J. Jun. 12, 2009;421 (1):29-42.
Gaster et al., GLUT4 is reduced in slow muscle fibers of type 2 diabetic patients: is insulin resistance in type 2 diabetes a slow, type 1 fiber disease? Diabetes. Jun. 2001;50(6):1324-9.
Gavai et al., BMS-196085: a potent and selective full agonist of the human beta(3) adrenergic receptor. Bioorg Med Chem Lett. Dec. 3, 2001;11(23):3041-4.
Gawlik et al., Targeted disruption of Slc2a8 (GLUT8) reduces motility and mitochondrial potential of spermatozoa. Mol Membr Biol. Apr. 2008;25(3):224-35.
Gilman, G proteins: transducers of receptor-generated signals. Annu Rev Biochem. 1987;56:615-49.
Green et al., Use of Akt inhibitor and a drug-resistant mutant validates a critical role for protein kinase B/Akt in the insulin-dependent regulation of glucose and system A amino acid uptake. J Biol Chem. Oct. 10, 2008;283(41):27653-67.
Greife et al., Effects of the phenethanolamine clenbuterol on protein and lipid metabolism in growing rats. J Anim Physiol a Anim Nutr. 1989;61:19-27.
Gusovsky, Measurement of second messengers in signal transduction: cAMP and inositol phosphates. Curr Protoc Neurosci. May 2001;Chapter 7:Unit7.12.
Harrison et al., Activation of cell surface glucose transporters measured by photoaffinity labeling of insulin-sensitive 3T3-L1 adipocytes. J Biol Chem. Feb. 25, 1992;267(6):3783-8.
Harrison et al., Suppressed intrinsic catalytic activity of GLUT1 glucose transporters in insulin-sensitive 3T3-L1 adipocytes. Proc Natl Acad Sci U S A. Sep. 1, 1991;88(17):7839-43.
Hawkins et al., Signalling through Class I PI3Ks in mammalian cells. Biochem Soc Trans. Nov. 2006;34(Pt 5):647-62.
Hebert et al., Direct evidence for ATP modulation of sugar transport in human erythrocyte ghosts. J Biol Chem. Aug. 5, 1986;261(22):10093-9.
Hresko et al., mTOR.RICTOR is the Ser473 kinase for Akt/protein kinase B in 3T3-L1 adipocytes. J Biol Chem. Dec. 9, 2005;280(49):40406-16.
Huang et al., The GLUT4 glucose transporter. Cell Metab. Apr. 2007;5(4):237-52.
Huang, An in vitro assay for the kinase activity of mTOR complex 2. Methods Mol Biol. 2012;821:75-86.
Hutchinson et al., Agonist effects of zinterol at the mouse and human beta(3)-adrenoceptor. Naunyn Schmiedebergs Arch Pharmacol. May 2006;373(2):158-68.
Hutchinson et al., alpha1A-adrenoceptors activate glucose uptake in L6 muscle cells through a phospholipase C-, phosphatidylinositol-3 kinase-, and atypical protein kinase C-dependent pathway. Endocrinology. Feb. 2005;146(2):901-12.
Hutchinson et al., AMP-activated protein kinase activation by adrenoceptors in L6 skeletal muscle cells: mediation by alpha1-adrenoceptors causing glucose uptake. Diabetes. Mar. 2006;55(3):682-90.
Inokuma et al., Uncoupling protein 1 is necessary for norepinephrine-induced glucose utilization in brown adipose tissue. Diabetes. May 2005;54(5):1385-91.
Jones et al., G protein-coupled receptor kinases 2 and 5 are differentially expressed in rat skeletal muscle and remain unchanged following beta2-agonist administration. Exp Physiol. Mar. 2003;88(2):277-84.
Jozwiak et al., Comparative molecular field analysis of the binding of the stereoisomers of fenoterol and fenoterol derivatives to the beta2 adrenergic receptor. J Med Chem. Jun. 2007;50(12):2903-15.
Kaiser et al., Adrenergic agents. 1. Synthesis and potential beta-adrenergic agonist activity of some catecholamine analogs bearing a substituted amino functionality in the meta position. J Med Chem. Jan. 1974;17(1):49-57.
Kleiman et al., Developmentally spliced PKCbetaII provides a possible link between mTORC2 and Akt kinase to regulate 3T3-L1 adipocyte insulin-stimulated glucose transport. Biochem Biophys Res Commun. Oct. 23, 2009;388(3):554-9.
Koshy et al., Quantitative Measurement of GLUT4 Translocation to the Plasma Membrane by Flow Cytometry. Jove, J Vis Exp. www.jove.com. 3 pages, (2010).
Kovala et al., Protein kinase A regulation of cAMP phosphodiesterase expression in rat skeletal myoblasts. J Biol Chem. Mar. 25, 1994;269(12):8680-5.
Kumar et al., Fat cell-specific ablation of rictor in mice impairs insulin-regulated fat cell and whole-body glucose and lipid metabolism. Diabetes. Jun. 2010;59(6):1397-406.
Lacey et al., Selective stimulation of glucagon secretion by beta 2-adrenoceptors in isolated islets of Langerhans of the rat. Br J Pharmacol. Jul. 1991;103(3):1824-8.
Lamming et al., A Central role for mTOR in lipid homeostasis. Cell Metab. Oct. 1, 2013;18(4):465-9.
Laplante et al., mTOR signaling in growth control and disease. Cell. Apr. 13, 2012;149(2):274-93.
Largis et al., Antidiabetic and antiobesity effects of a highly selective ß3-adrenoceptor agonist (CL 316,243). Drug Development Research. Jun. 1994;32(2):69-76.
Lawrence et al., GLUT4 facilitates insulin stimulation and cAMP-mediated inhibition of glucose transport. Proc Natl Acad Sci U S A. Apr. 15, 1992;89(8):3493-7.
Lidell et al., Evidence for two types of brown adipose tissue in humans. Nat Med. May 2013;19(5):631-4.
Liggett et al., Characterization of beta-adrenergic receptors of human skeletal muscle obtained by needle biopsy. Am J Physiol. 1988;254:E795-8.
Liu et al., Biphasic effects of the beta-adrenoceptor agonist, BRL 37344, on glucose utilization in rat isolated skeletal muscle. Br J Pharmacol. Mar. 1996;117(6):1355-61.
Liu et al., Chronic norepinephrine infusion stimulates glucose uptake in white and brown adipose tissues. Am J Physiol. 1994;266:914-20.
MacAulay et al., Isoproterenol inhibits cyclic AMP-mediated but not insulin-mediated translocation of the GLUT4 glucose transporter isoform. Mol Cell Biochem. Dec. 7, 1994;141(1):27-33.
Macheda et al., Molecular and cellular regulation of glucose transporter (GLUT) proteins in cancer. J Cell Physiol. Mar. 2005;202(3):654-62.
Marette et al., Stimulation of glucose transport by insulin and norepinephrine in isolated rat brown adipocytes. Am J Physiol. Oct. 1989;257(4 Pt 1):C714-21.
Mathvink et al., Potent, selective 3-pyridylethanolamine beta3 adrenergic receptor agonists possessing a thiazole benzenesulfonamide pharmacophore. Bioorg Med Chem Lett. Sep. 4, 2000;10(17):1971-3.
Mills et al., Beta-blockers and glucose control. Drug Intell Clin Pharm. Apr. 1985;19(4):246-51.
Murata et al., Indinavir inhibits the glucose transporter isoform Glut4 at physiologic concentrations. AIDS. Apr. 12, 2002;16(6):859-63.
Nave et al., Mammalian target of rapamycin is a direct target for protein kinase B: identification of a convergence point for opposing effects of insulin and amino-acid deficiency on protein translation. Biochem J. Dec. 1, 1999;344 Pt 2:427-31.
Nedergaard et al., New powers of brown fat: fighting the metabolic syndrome. Cell Metab. Mar. 2, 2011;13(3):238-40.

(56) References Cited

OTHER PUBLICATIONS

Nedergaard et al., PPARgamma in the control of brown adipocyte differentiation. Biochim Biophys Acta. May 30, 2005;1740(2):293-304.
Nedergaard et al., Three years with adult human brown adipose tissue. Ann N.Y. Acad Sci. 2011;1212:E20-E36.
Nedergaard et al., Unexpected evidence for active brown adipose tissue in adult humans. Am J Physiol Endocrinol Metab. 2007;293:E444-E452.
Neve et al., Turnover of beta 1- and beta 2-adrenergic receptors after down-regulation or irreversible blockade. Mol Pharmacol. Aug. 1986;30(2):104-11.
Nevzorova et al., Characterization of the beta-adrenoceptor subtype involved in mediation of glucose transport in L6 cells. Br J Pharmacol. Sep. 2002;137(1):9-18.
Nevzorova et al., Multiple signalling pathways involved in beta2-adrenoceptor-mediated glucose uptake in rat skeletal muscle cells. Br J Pharmacol. Feb. 2006;147(4):446-54.
Ngala et al., beta2-adrenoceptor agonists can both stimulate and inhibit glucose uptake in mouse soleus muscle through ligand-directed signalling. Naunyn Schmiedebergs Arch Pharmacol. Sep. 2013;386(9):761-73.
Ngala et al., Beta2-adrenoceptors and non-beta-adrenoceptors mediate effects of BRL37344 and clenbuterol on glucose uptake in soleus muscle: studies using knockout mice. Br J Pharmacol. Dec. 2009;158(7):1676-82.
Ngala et al., Metabolic responses to BRL37344 and clenbuterol in soleus muscle and C2C12 cells via different atypical pharmacologies and beta2-adrenoceptor mechanisms. Br J Pharmacol. Oct. 2008;155(3):395-406.
Nobles et al., Distinct phosphorylation sites on the beta(2)-adrenergic receptor establish a barcode that encodes differential functions of beta-arrestin. Sci Signal. Aug. 9, 2011;4(185):ra51.
Nugent et al., Potentiation of glucose uptake in 3T3-L1 adipocytes by PPAR gamma agonists is maintained in cells expressing a PPAR gamma dominant-negative mutant: evidence for selectivity in the downstream responses to PPAR gamma activation. Mol Endocrinol. Oct. 2001;15(10):1729-38.
Palmada et al., SGK1 kinase upregulates GLUT1 activity and plasma membrane expression. Diabetes. Feb. 2006;55(2):421-7.
Pan et al., Effects of clenbuterol on insulin resistance in conscious obese Zucker rats. Am J Physiol Endocrinol Metab. Apr. 2001;280(4):E554-61.
Parmee et al., Discovery of L-755,507: a subnanomolar human beta 3 adrenergic receptor agonist. Bioorg Med Chem Lett. May 5, 1998;8(9):1107-12.
Phung et al., Pathological angiogenesis is induced by sustained Akt signaling and inhibited by rapamycin. Cancer Cell. Aug. 2006;10(2):159-70.
Plazinska et al., Molecular interactions between fenoterol stereoisomers and derivatives and the beta2-adrenoceptor binding site studied by docking and molecular dynamics simulations. J Mol Model. Nov. 2013;19(11):4919-30.
Ploug et al., Kinetics of glucose transport in rat muscle: effects of insulin and contractions. Am J Physiol. 1987;253:12-20.
Polak et al., Adipose-specific knockout of raptor results in lean mice with enhanced mitochondrial respiration. Cell Metab. Nov. 2008;8(5):399-410.
PubChem CID: CID=4225365, 2-(Cyclohexylmethylamino)-1-phenylethanol, 2-[(cyclohexylmethyl)amino]-1-phenylethanol; 2-(cyclohexylmethylamino)-1-phen HMS1755E04, 1 page, Dec. 1, 2018.
PubChem CID: CID=83307546, SCHEMBL19329935; AKOS023017379. 4-[2-(Cyclohexylmethylamino)-1-hydroxyethyl]phenol. Dec. 12, 2001.
PubChem, Compound CID: 60051619, SCHEMBL19329904, 1 page, Aug. 20, 2012.
PubChem, Compound CID: 89173082, SCHEMBL13799302, 1 page, Feb. 13, 2015.
Rao et al., Synthesis, antimicrobial and molecular docking studies of enantiomerically pure N-alkylated beta-amino alcohols from phenylpropanolamines. Bioorg Med Chem Lett. Jul. 2014;24(14):3057-63.
Reinicke et al., Cellular distribution of Glut-1 and Glut-5 in benign and malignant human prostate tissue. J Cell Biochem. Feb. 2012;113(2):553-62.
Rodnick et al., Interaction of insulin and exercise on glucose transport in muscle. Diabetes Care. Nov. 1992;15(11):1679-89.
Rovira et al., mTOR Inhibition: Reduced Insulin Secretion and Sensitivity in a Rat Model of Metabolic Syndrome. Transplant Direct. Jan. 22, 2016;2(2):e65, 9 pages.
Rowland et al., Mapping insulin/GLUT4 circuitry. Traffic. Jun. 2011;12(6):672-81.
Rydzewski, Real World Drug Discovery, a Chemist's Guide to Biotech and Pharmaceutical Research. Elsevier, Amsterdam. pp. 42-43, (2008).
Salvador et al., Inhibition by butoxamine, propranolol and MJ1999 of the glycogenolytic action of the catecholamines in the rat. Biochem Pharmacol. Oct. 1967;16(10):2037-41.
Santulli et al., Pinpointing beta adrenergic receptor in ageing pathophysiology: victim or executioner? Evidence from crime scenes. Immun Ageing. Mar. 15, 2013;10(1):10.
Sarabia et al., Glucose uptake in human and animal muscle cells in culture. Biochem Cell Biol. Feb. 1990;68(2):536-42.
Sarbassov et al., Prolonged rapamycin treatment inhibits mTORC2 assembly and Akt/PKB. Mol Cell. Apr. 21, 2006;22(2):159-68.
Sarbassov et al., Rictor, a novel binding partner of mTOR, defines a rapamycin-insensitive and raptor-independent pathway that regulates the cytoskeleton. Curr Biol. Jul. 27, 2004;14(14):1296-302.
Sekulic et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sennitt et al., The contribution of classical (beta1/2-) and atypical beta-adrenoceptors to the stimulation of human white adipocyte lipolysis and right atrial appendage contraction by novel beta3-adrenoceptor agonists of differing selectivities. J Pharmacol Exp Ther. Jun. 1998;285(3):1084-95.
Shah et al., The role of glucose transporters in brain disease: diabetes and Alzheimer's Disease. Int J Mol Sci. Oct. 3, 2012;13(10):12629-55.
Shan et al., Effects of GLUT4 expression on insulin resistance in patients with advanced liver cirrhosis. J Zhejiang Univ Sci B. Aug. 2011;12(8):677-82.
Shenoy et al., G-Protein Coupled Receptor—A Potential New Drug Target to Combat Diabetic Syndrome: An Overview. IJPSR. 2011;2(10):2490-2500.
Shibata et al., Cold exposure reverses inhibitory effects of fasting on peripheral glucose uptake in rats. Am J Physiol. Jul. 1989;257(1 Pt 2):R96-101.
Shimizu et al., Activation of brown adipose tissue thermogenesis in recovery from anesthetic hypothermia in rats. Am J Physiol. Aug. 1991;261(2 Pt 2):R301-4.
Simpson et al., The facilitative glucose transporter GLUT3: 20 years of distinction. Am J Physiol Endocrinol Metab. 2008;295:E242-E253.
Sobel et al., Abolition of crypticity of Arthrobacter pyridinolis toward glucose and alpha-glucosides by tricarboxylic acid cycle intermediates. J Bacteriol. Oct. 1973;116(1):271-8.
Spiller et al., A descriptive study of adverse events from clenbuterol misuse and abuse for weight loss and bodybuilding. Subst Abus. 2013;34(3):306-12.
Sprenger et al., Biophysical techniques for detection of cAMP and cGMP in living cells. Int J Mol Sci. Apr. 12, 2013;14(4):8025-46.
Stanford et al., Brown adipose tissue regulates glucose homeostasis and insulin sensitivity. J Clin Invest. Jan. 2013;123(1):215-23.
Taha et al., The insulin-dependent biosynthesis of GLUT1 and GLUT3 glucose transporters in L6 muscle cells is mediated by distinct pathways. Roles of p21ras and pp70 S6 kinase. J Biol Chem. Oct. 20, 1995;270(42):24678-81.
Tanis et al., Solvent and in situ catalyst preparation impacts upon Noyori reductions of aryl-chloromethyl ketones: application to

(56) References Cited

OTHER PUBLICATIONS syntheses of chiral 2-amino-1-aryl-ethanols. Tetrahedron: Asymmetry. Aug. 28, 2006;17(14):2154-82.
Tanis et al., The design and development of 2-aryl-2-hydroxy ethylamine substituted 1H,7H-pyrido[1,2,3-de]quinoxaline-6-carboxamides as inhibitors of human cytomegalovirus polymerase. Bioorg Med Chem Lett. Mar. 15, 2010;20(6):1994-2000.
Taverna et al., Reversible association of cytochalasin B with the human erythrocyte membrane. Inhibition of glucose transport and the stoichiometry of cytochalasin binding. Biochim Biophys Acta. Oct. 11, 1973;323(2):207-19.
Thong et al., Turning signals on and off: GLUT4 traffic in the insulin-signaling highway. Physiology (Bethesda). Aug. 2005;20:271-84.
Torgan et al., Exercise training and clenbuterol reduce insulin resistance of obese Zucker rats. Am J Physiol. Mar. 1993;264(3 Pt 1):E373-9.
Tritos et al., Clinical review 97: Syndromes of severe insulin resistance. J Clin Endocrinol Metab. Sep. 1998;83(9):3025-30.
Unger, Die Wirkung von butedrin auf den Blutzucker. The Effect of Butedrine on Blood Sugar. Zschr Inn Med. Jour Inn Med. Apr. 8, 1961;16(17):742-745.
Vardanega-Peicher et al., Time sequence of changes in the responsiveness of glycogen breakdown to adrenergic agonists in perfused liver of rats with insulin-induced hypoglycemia. Braz J Med Biol Res. Jul. 2000;33(7):805-13.
Violin et al., G-protein-coupled receptor kinase specificity for beta-arrestin recruitment to the beta2-adrenergic receptor revealed by fluorescence resonance energy transfer. J Biol Chem. Jul. 21, 2006;281(29):20577-88.
Watson-Wright et al., The Muscle Slice—A New Preparation for the Characterization of beta-Adrenergic Binding in Fast- and Slow-twitch Skeletal Muscle. Muscle & Nerve. 1986;9:416-22.
Woo et al., Stereochemistry of an agonist determines coupling preference of beta2-adrenoceptor to different G proteins in cardiomyocytes. Mol Pharmacol. Jan. 2009;75(1):158-65.
Yamamoto et al., Beta(2)-Adrenergic activation increases glycogen synthesis in L6 skeletal muscle cells through a signalling pathway independent of cyclic AMP. Diabetologia. Jan. 2007;50(1):158-67.
Zeng et al., Rapamycin derivatives reduce mTORC2 signaling and inhibit AKT activation in AML. Blood. Apr. 15, 2007;109(8):3509-12.
Zhu et al., Discovery of benzamides as potent human ß3 adrenergic receptor agonists. Bioorg Med Chem Lett. Jan. 1, 2016;26(1):55-9.
Ziegler et al., Endogenous epinephrine protects against obesity induced insulin resistance. Auton Neurosci. Jul. 5, 2011;162(1-2):32-4.
Ziegler et al., Epinephrine and the metabolic syndrome. Curr Hypertens Rep. Feb. 2012;14(1):1-7.
Zierath, In vitro studies of human skeletal muscle: hormonal and metabolic regulation of glucose transport. Acta Physiol Scand Suppl. 1995;626:1-96.
Zinzalla et al., Activation of mTORC2 by association with the ribosome. Cell. Mar. 4, 2011;144(5):757-68.
International Search Report and Written Opinion for Application No. PCT/GB2018/052594, dated Oct. 26, 2018, 11 pages.
Ashmore et al., Effects of Dichloroisoproterenol on Blood Sugar and Plasma Free Fatty Acids. Proceedings of the Society for Experimental Biology and Medicine. 1962;109:291-294.
Chait et al., Diabetes and atherosclerosis: is there a role for hyperglycemia? J Lipid Res. Apr. 2009;50 Suppl(Suppl):S335-9.
Bercher et al., Pharmakologische Eigenschaften fluorierter Phenylathanolamine [Pharmacologic properties of fluorinated phenylethanolamine]. Acta Biol Med Ger. 1974;33(3):335-41.

STN RN 582-40-1, Benzenemethanol, alpha-[[(1,1-dimethylethyl)amino]methyl]-3-fluoro-hydrobromide. 1 page, Nov. 16, 1984.
Tsuiki et al., Effect of the beta-adrenoceptor agonist flerobuterol on serotonin synthesis in the rat brain. Biochem Pharmacol. Mar. 15, 2000;59(6):673-9.
Baltzly et al., N-sec- and N-t-alkyl derivatives of methoxamine and related compounds. J Med Chem. Jul. 1968;11(4):833-44.
Chiarino et al., New Isoxazole Derivatives with a Potent and Selective beta2-Adrenergic Activity. II Farmaco. 1985;41:440-453.
Friz, Derivati All'Azoto Aminico Dell'1-(4'Piridil)-2-Aminoetanolo. II Farmaco. 1963;18:972-980.
Grandi et al., Synthesis and pharmacological investigation of New Arylethanolamines as Beta3-Adrenoceptor Ligands. Pharm Pharmacol Commun. 1999;5:561-564.
STN RN 1868397-08-3, Benzenemethanol, 4-fluoro-alpha-[[(1-methylbutyl)amino]methyl], 1 page, Feb. 17, 2016.
STN RN 1179721-98-2, Benzenemethanol, alpha-[[(1-ethylpropyl)amino]methyl]-2,6-difluoro. 17 pages, Sep. 3, 2009.
Lands, The Effect on Blood Pressure and Toxicity of 1-[3-Fluorophenyl)-2-Aminoethanol and Related Compounds. Journal of Pharmacology and Experimental Therapeutics. Dec. 1, 1952;106(4):440-443.
Besev et al., Diastereocontrol by a hydroxyl auxiliary in the synthesis of pyrrolidines via radical cyclization. Org Lett. Sep. 5, 2002:4(18):3023-5.
Mathvink et al., Discovery of a potent orally bioavailable beta(3) adrenergic receptor agonist, (R)-N-4-[2-[[2-hydroxy-2-(3-pyridinyl)ethyl]amino]ethyl]phenyl]-4-[4-[4-(trifluoromethyl)phenyl]thiazol-2-yl]benzenesulfonamide. J Med Chem. Oct. 19, 2000;43(21):3832-6.
Ookawa et al., Asymmetric Synthesis of Optically Active threo- and erythro-Pyrrolidinylbenzyl Alcohol by the Highly Stereospecific Arylation of (S)-Proline and the Subsequent Highly Diastereoselective Reduction of the alpha-Amino Ketone. J Chem Soc Perkin Trans 1. 1987;1465-1471.
U.S. Appl. No. 14/759,572, filed Jul. 7, 2015, U.S. Pat. No. 9,784,726, Issued.
U.S. Appl. No. 14/727,851, filed Oct. 9, 2017, U.S. Pat. No. 10,288,602, Issued.
U.S. Appl. No. 14/759,747, filed Apr. 8, 2015, U.S. Pat. No. 9,657,348, Issued.
U.S. Appl. No. 15/104,830, filed Jun. 15, 2016, U.S. Pat. No. 9,891,212, Issued.
U.S. Appl. No. 15/324,580, filed Jan. 6, 2017, 2017-0153225, Abandoned.
U.S. Appl. No. 16/082,750, filed Sep. 6, 2018, 2019-0119196, Published.
U.S. Appl. No. 16/317,009, filed Jan. 10, 2019, 2019-0314301, Abandoned.
U.S. Appl. No. 16/908,312, filed Jun. 22, 2020, 2020-0315993, Abandoned.
U.S. Appl. No. 17/320,774, filed May 14, 2021, 2021-0338603, Published.
U.S. Appl. No. 16/646,050, filed Mar. 10, 2020, U.S. Pat. No. 11,427,539, Issued.
U.S. Appl. No. 16/646,492, filed Mar. 11, 2020, 2020-0268687, Published.
U.S. Appl. No. 16/645,286 filed Mar. 6, 2020, U.S. Pat. No. 11,357,757, Issued.
U.S. Appl. No. 17/575,175, filed Jan. 13, 2022, 2022-0133703, Published.
U.S. Appl. No. 17/439,638, filed Sep. 15, 2021, 2022-0194920, Published.
U.S. Appl. No. 17/439,668, filed Sep. 15, 2021, 2022-0150004, Published.

* cited by examiner

FLUOROPHENYL BETA-HYDROXYETHYLAMINES AND THEIR USE IN THE TREATMENT OF HYPERGLYCAEMIA

CROSS-REFERENCE TO RELATED APPLICATIONS

This application is a U.S. national stage filing, under 35 U.S.C. § 371(c), of International Application No. PCT/GB2018/052594, filed on Sep. 13, 2018, which claims priority to United Kingdom Patent Application No. 1714734.9, filed on Sep. 13, 2017.

FIELD OF THE INVENTION

The present invention relates to novel compounds and compositions, and their use in the treatment of hyperglycaemia and disorders characterised by hyperglycaemia, such as type 2 diabetes. In particular, the invention relates to novel compounds, compositions and methods for the treatment of conditions such as type 2 diabetes through activation of the $\beta_2$-adrenergic receptor. Importantly, such compounds are thought to have a beneficial side-effect profile as they do not exert their effect through significant cAMP release.

BACKGROUND OF THE INVENTION

The listing or discussion of an apparently prior-published document in this specification should not necessarily be taken as an acknowledgement that the document is part of the state of the art or is common general knowledge.

Hyperglycaemia, or high blood sugar is a condition in which an excessive amount of glucose circulates in the blood plasma. If not treated, hyperglycaemia can be a serious problem, potentially developing into life-threatening conditions such as ketoacidosis. For example, chronic hyperglycemia may cause injury to the heart, and is strongly associated with heart attacks and death in subjects with no coronary heart disease or history of heart failure. There are various causes of hyperglycaemia, including diabetes and severe insulin resistance.

Severe insulin resistance (SIR) is a condition wherein the patent experiences very low levels of (or, in extreme cases, no significant) response to insulin. There are several syndromes characterized by SIR, including Rabson-Mendenhall syndrome, Donohue's syndrome (leprechaunism), Type A and Type B syndromes of insulin resistance, the HAIR-AN (hyperandrogenism, insulin resistance, and acanthosis *nigricans*) syndrome, pseudoacromegaly, and lipodystrophy. The majority of these conditions have genetic causes, such as mutations in the insulin receptor gene. The prevalence for Donohue's syndrome, Rabson-Mendenhall syndrome and Type A syndrome of insulin resistance, has been reported to vary from about 50 reported cases to 1 in 100,000. However, since some diseases are severe and extremely rare, it is likely that many patients do not get diagnosed before they die, particularly in less developed areas of the world. Thus, the exact number of patients with these syndromes is difficult to assess.

The current standard for hyperglycaemia treatment in patients having SIR is a controlled diet, supplemented with drugs affecting insulin receptor sensitivity, such as metformin, or insulin supplement. However, particularly for disorders caused by mutations in the insulin receptor gene, this treatment is not sufficiently effective and ultimately proves unsuccessful.

Diabetes comprises two distinct diseases, type 1 (or insulin-dependent diabetes) and type 2 (insulin-independent diabetes), both of which involve the malfunction of glucose homeostasis. Type 2 diabetes affects more than 400 million people in the world and the number is rising rapidly. Complications of type 2 diabetes include severe cardiovascular problems, kidney failure, peripheral neuropathy, blindness and, in the later stages of the disease, even loss of limbs and, ultimately death. Type 2 diabetes is characterized by insulin resistance in skeletal muscle and adipose tissue, and there is presently no definitive cure. Most treatments used today are focused on remedying dysfunctional insulin signalling or inhibiting glucose output from the liver but many of those treatments have several drawbacks and side effects. There is thus a great interest in identifying novel insulin-independent ways to treat type 2 diabetes.

In type 2 diabetes, the insulin-signalling pathway is blunted in peripheral tissues such as adipose tissue and skeletal muscle. Methods for treating type 2 diabetes typically include lifestyle changes, as well as insulin injections or oral medications to regulate glucose homeostasis. People with type 2 diabetes in the later stages of the disease develop 'beta-cell failure' i.e. the inability of the pancreas to release insulin in response to high blood glucose levels. In the later stages of the disease patients often require insulin injections in combination with oral medications to manage their diabetes. Further, most common drugs have side effects including downregulation or desensitization of the insulin pathway and/or the promotion of lipid incorporation in adipose tissue, liver and skeletal muscle. There is thus a great interest in identifying novel ways to treat metabolic diseases including type 2 diabetes that do not include these side effects.

Following a meal, increased blood glucose levels stimulate insulin release from the pancreas. Insulin mediates normalization of the blood glucose levels. Important effects of insulin on glucose metabolism include facilitation of glucose uptake into skeletal muscle and adipocytes, and an increase of glycogen storage in the liver. Skeletal muscle and adipocytes are responsible for insulin-mediated glucose uptake and utilization in the fed state, making them very important sites for glucose metabolism.

The signalling pathway downstream from the insulin receptor has been difficult to understand in detail. In brief, control of glucose uptake by insulin involves activation of the insulin receptor (IR), the insulin receptor substrate (IRS), the phosphoinositide 3-kinase (PI3K) and thus stimulation of phosphatidylinositol (3,4,5)-triphosphate (PIP3), the mammalian target of rapamycin (also called the mechanistic target of rapamycin, mTOR), Akt/PKB (Akt) and TBC1 D4 (AS160), leading to translocation of the glucose transporter 4 (GLUT4) to the plasma membrane. Akt activation is considered necessary for GLUT4 translocation.

It should be noted that skeletal muscles constitute a major part of the body weight of mammals and have a vital role in the regulation of systemic glucose metabolism, being responsible for up to 85% of whole-body glucose disposal. Glucose uptake in skeletal muscles is regulated by several intra- and extracellular signals. Insulin is the most well studied mediator but others also exist. For example, AMP activated kinase (AMPK) functions as an energy sensor in the cell, which can increase glucose uptake and fatty acid oxidation. Due to the great influence skeletal muscles have on glucose homeostasis it is plausible that additional mechanisms exist. In the light of the increased prevalence of type 2 diabetes, it is of great interest to find and characterize novel insulin-independent mechanisms to increase glucose uptake in muscle cells.

Blood glucose levels may be regulated by both insulin and catecholamines, but they are released in the body in response to different stimuli. Whereas insulin is released in response to the rise in blood sugar levels (e.g. after a meal), epinephrine and norepinephrine are released in response to various internal and external stimuli, such as exercise, emotions and stress, and also for maintaining tissue homeostasis. Insulin is an anabolic hormone that stimulates many processes involved in growth including glucose uptake, glycogen and triglyceride formation, whereas catecholamines are mainly catabolic.

Although insulin and catecholamines normally have opposing effects, it has been shown that they have similar actions on glucose uptake in skeletal muscle (Nevzorova et al., *Br. J. Pharmacol*, 137, 9, (2002)). In particular, it has been reported that catecholamines stimulate glucose uptake via adrenergic receptors (Nevzorova et al., *Br. J. Pharmacol*, 147, 446, (2006); Hutchinson, Bengtsson *Endocrinology* 146, 901, (2005)) to supply muscle cells with an energy-rich substrate. Thus it is likely that in mammals, including humans, the adrenergic and the insulin systems can work independently to regulate the energy needs of skeletal muscle in different situations. Since insulin also stimulates many anabolic processes, including some that promote undesired effects such as stimulation of lipid incorporation into tissues, leading to e.g. obesity, it would be beneficial to be able to stimulate glucose uptake by other means; for example, by stimulation of the adrenergic receptors (ARs).

All ARs are G protein-coupled receptors (GPCRs) located in the cell membrane and characterized by an extracellular N-terminus, followed by seven transmembrane α-helices (TM-1 to TM-7) connected by three intracellular (IL-1 to IL-3) and three extracellular loops (EL-1 to EL-3), and finally an intracellular C-terminus. There are three different classes of ARs, with distinct expression patterns and pharmacological profiles: $\alpha_1$-, $\alpha_2$- and β-ARs. The $\alpha_1$-ARs comprise the $\alpha_{1A}$, $\alpha_{1B}$ and $\alpha_{1D}$ subtypes while $\alpha_2$-ARs are divided into $\alpha_{2A}$, $\alpha_{2B}$ and $\alpha_{2C}$. The β-ARs are also divided into the subtypes $\beta_1$, $\beta_2$, and $\beta_3$, of which $\beta_2$-AR is the major isoform in skeletal muscle cells. ARs are G protein coupled receptors (GPCRs) that signal through classical secondary messengers such as cyclic adenosine monophosphate (cAMP) and phospholipase C (PLC).

Many effects occurring downstream of ARs in skeletal muscles have been attributed to classical secondary messenger signalling, such as increase in cAMP levels, PLC activity and calcium levels. Stimulation involving the classical secondary messengers has many effects in different tissues. For example, it increases heart rate, blood flow, airflow in lungs and release of glucose from the liver, which all can be detrimental or be considered unwanted side effects if stimulation of ARs should be considered as a type 2 diabetes treatment. Adverse effects of classical AR agonists are, for example, tachycardia, palpitation, tremor, sweats, agitation and increased glucose levels in the blood (glucose output from the liver). It would thus be beneficial to be able to activate ARs without activating these classical secondary messengers, such as cAMP, to increase glucose uptake in peripheral tissues without stimulating the unwanted side effects.

Glucose uptake is mainly stimulated via facilitative glucose transporters (GLUT) that mediate glucose uptake into most cells. GLUTs are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied isoforms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in, for example, the brain, kidney, and liver. GLUT4 is the major isoform involved in insulin stimulated glucose uptake. The mechanism whereby insulin signalling increases glucose uptake is mainly via GLUT4 translocation from intracellular storage to the plasma membrane. It is known that GLUT4 translocation is induced by stimulation of the $\beta_2$-adrenergic receptor.

Thus, a possible treatment of a condition involving dysregulation of glucose homeostasis or glucose uptake in a mammal, such as type 2 diabetes, would involve the activation of the $\beta_2$-adrenergic receptor leading to GLUT4 translocation to the plasma membrane and promotion of glucose uptake into skeletal muscle leading to normalization of whole body glucose homeostasis. In addition, it would be advantageous if the treatment does not involve signalling through cAMP as this would lead to a favourable side-effect profile.

The vasodilator 4-(2-(butylamino)-1-hydroxyethyl)phenol, which has been used in the treatment of peripheral vascular disorders, has been found to initially increase blood sugar and has been contraindicated in diabetes and pre-diabetes (see Unger, H., *Zeitschrift for die Gesamte Innere Medizin und Ihre Grenzgebiete*, 16, 742 (1961)).

DESCRIPTION OF THE INVENTION

We have now surprisingly found that certain fluoro substituted β-hydroxyethylamines acting as agonists at the $\beta_2$-adrenergic receptor increase glucose uptake in skeletal muscle.

In addition, we have found that this effect is not mediated through significant cAMP release, such that many of the commonly described side effects seen with traditional $\beta_2$-adrenergic agonists (e.g. tachycardia, palpitation, tremor, sweats, agitation, and the like) can be reduced.

The use of such compounds in medicine represents a promising strategy for the treatment of conditions characterized by high blood sugar levels (i.e. hyperglycaemia), such as type 2 diabetes.

Compounds of the Invention

In a first aspect of the invention, there is provided a compound of formula I

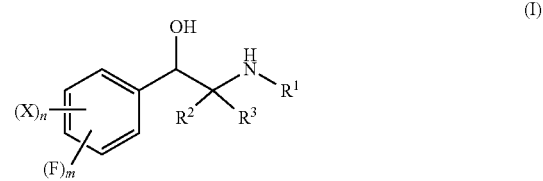

or a pharmaceutically acceptable salt thereof, wherein:

$R^1$ represents $C_{4-12}$ alkyl optionally substituted by one or more halo;

$R^2$ and $R^3$ each independently represent H or $C_{1-3}$ alkyl optionally substituted by one or more halo;

or $R^2$ and $R^3$ may be linked together to form, together with the carbon atom to which they are attached, a 3- to 6-membered ring, which ring optionally is substituted by one or more groups independently selected from halo and $C_1$ alkyl optionally substituted by one or more halo;

each X independently represents Cl, Br, $R^a$, —CN, —$N_3$, —$N(R^b)R^c$, —$NO_2$, —$ONO_2$, —$OR^d$, —$S(O)_pR^e$ or —$S(O)_qN(R^f)R^g$—;

$R^a$ represents $C_{1-6}$ alkyl optionally substituted by one or more groups independently selected from G;

each $R^b$, $R^c$, $R^d$, $R^e$, $R^f$ and $R^g$ independently represents H or $C_{1-6}$ alkyl optionally substituted by one or more groups independently selected from G;

or alternatively any of $R^b$ and $R^c$ and/or $R^f$ and $R^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

G represents halo, —CN, —$N(R^{a1})R^{b1}$, —$OR^1$, —$S(O)_pR^{d1}$, —$S(O)_qN(R^{e1})R^{f1}$ or =O;

each $R^{a1}$, $R^{b1}$, $R^{c1}$, $R^{d1}$, $R^{e1}$ and $R^{11}$ independently represents H or $C_{1-6}$ alkyl optionally substituted by one or more halo;

or alternatively any of $R^{a1}$ and $R^{b1}$ and/or $R^{e1}$ and $R^{11}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl optionally substituted by one or more halo, and =O;

m represents 1 to 5;

n represents 0 to 4;

with the proviso that the sum of m and n is equal to, or less than, 5;

each p independently represents 0, 1 or 2; and each q independently represents 1 or 2;

which compounds (including pharmaceutically acceptable salts) may be referred to herein as the "compounds of the invention".

For the avoidance of doubt, the skilled person will understand that references herein to compounds of particular aspects of the invention (such as the first aspect of the invention, e.g. compounds of formula I) will include references to all embodiments and particular features thereof, which embodiments and particular features may be taken in combination to form further embodiments.

Unless indicated otherwise, all technical and scientific terms used herein have the same meaning as commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalenedisulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the first aspect of the invention may exist as solids, and thus the scope of the invention includes all amorphous, crystalline and part crystalline forms thereof, and may also exist as oils. Where compounds of the first aspect of the invention exist in crystalline and part crystalline forms, such forms may include solvates, which are included in the scope of the invention. Compounds of the first aspect of the invention may also exist in solution.

Compounds of the first aspect of the invention may contain double bonds and may thus exist as E (entgegen) and Z (zusammen) geometric isomers about each individual double bond. All such isomers and mixtures thereof are included within the scope of the invention.

Compounds of the first aspect of the invention may also exhibit tautomerism. All tautomeric forms and mixtures thereof are included within the scope of the invention.

Compounds of the first aspect of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired optical isomers may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, references to halo and/or halogen groups will each independently refer to fluoro, chloro, bromo and iodo (for example, fluoro (F) and chloro (Cl)).

Unless otherwise specified, $C_{1-z}$ alkyl groups (where z is the upper limit of the range) defined herein may be straight-chain or, when there is a sufficient number (i.e. a minimum of three) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group). Particular alkyl groups that may be mentioned include saturated alkyl groups.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (e.g. oxygen, nitrogen and sulphur).

For the avoidance of doubt, references to polycyclic (e.g. bicyclic or tricyclic) groups (e.g. when employed in the context of cycloalkyl groups) will refer to ring systems wherein at least two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, and may also refer to groups in which two non-adjacent atoms are linked by an alkylene group, which later groups may be referred to as bridged.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more X groups are present, those X groups may be the same or different. Similarly, where two or more X groups are present and each represent halo, the halo groups in question may be the same or different. Likewise, when more than one $R^a$ is present and each independently represents $C_{1-6}$ alkyl substituted by one or more G group, the identities of each G are in no way interdependent.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

In particular embodiments of the first aspect of the invention, $R^1$ represents $C_{4-10}$ alkyl optionally substituted by one or more halo, such as $C_{4-8}$ alkyl optionally substituted by one or more halo.

In particular embodiments of the first aspect of the invention, $R^1$ represents $C_{4-10}$ alkyl optionally substituted by one or more F, such as $C_{4-8}$ alkyl optionally substituted by one or more F.

In more particular embodiments, $R^1$ represents $C_{4-10}$ alkyl, such as $C_{4-8}$ alkyl.

In further embodiments, $R^1$ represents $C_{4-7}$ alkyl (e.g. $C_{4-5}$ alkyl). For example, $R^1$ may represent $C_4$ alkyl (e.g. linear $C_4$ alkyl) or $C_5$ alkyl (e.g. branched $C_5$ alkyl).

In certain embodiments, where $R^1$ represents $C_{4-12}$ alkyl (e.g. $C_{4-7}$ alkyl, such as $C_{4-5}$ alkyl) the carbon bound to the essential —NH— group is unbranched, e.g. represented by a —CH$_2$— moiety.

In alternative embodiments, where $R^1$ represents $C_{4-12}$ alkyl (e.g. $C_{4-7}$ alkyl, such as $C_{4-5}$ alkyl) the carbon bound to the essential —NH— group is branched, e.g. represented by a —CH(CH$_3$)— moiety.

Particular $R^1$ groups that may be mentioned include those in which the alkyl group (e.g. the $C_{4-10}$ alkyl, such as $C_{4-8}$ alkyl) is linear (e.g. n-butyl, n-hexyl or n-octyl).

Certain further $R^1$ groups that may be mentioned include those in which the alkyl group (e.g. the $C_{4-10}$ alkyl, such as $C_{4-8}$ alkyl or, particularly, $C_{4-6}$ alkyl) is linear (e.g. n-butyl, n-hexyl or n-octyl, such as n-butyl), branched (e.g. t-butyl, neopentyl or 2-methyl-pentanyl), or cyclic/part-cyclic (e.g. methyl cyclobutyl or methyl cyclopropyl).

Yet more particular $R^1$ groups that may be mentioned include those in which the alkyl group represents $C_{4-12}$ alkyl (e.g. $C_{4-7}$ alkyl, such as $C_{4-5}$ alkyl) wherein the carbon bound to the essential —NH— group is substituted by one substituent, e.g. represented by a —CH(R$^4$)— moiety, wherein $R^4$ represents $C_{1-2}$ alkyl (e.g. methyl), e.g. wherein $R^1$ represents 2-pentyl.

In certain embodiments, $R^1$ represents n-butyl, tert-butyl or 2-pentyl.

In certain embodiments, $R^1$ represents 2-pentyl.

In further embodiments that may be mentioned, $R^1$ represents n-butyl, tert-butyl, 2-pentyl, 2-methyl-pent-2-yl, 1-methyl cyclobutyl, 1-methyl cyclopropyl or neopentyl.

In particular embodiments, $R^1$ does not represent tert-butyl.

For the avoidance of doubt, in certain embodiments $R^1$ represents tert-butyl.

In particular embodiments, $R^1$ represents a group of structure (i.e. substructure)

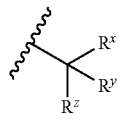

wherein:

$R^x$, $R^y$ and $R^z$ each independently represent H or $C_{1-11}$ alkyl (e.g. $C_1$ alkyl) optionally substituted by one or more F;

or alternatively $R^x$ and $R^z$ be linked together to form, together with the carbon atom to which they are attached, a 4- to 6-membered ring, which ring is optionally substituted by one or more F.

As used herein, the skilled person will understand that bonds terminating with ⟁ represents the point of attachment (e.g. to the essential N atom in compounds of formula I, including all embodiments thereof).

For the avoidance of doubt, the skilled person will understand that, where $R^1$ is represented by the substructure bearing $R^x$, $R^y$ and $R^z$ groups, the sum total of carbons presented in the $R^x$, $R^y$ and $R^z$ groups, together with the carbon to which they are attached, may not exceed those present in the corresponding $R^1$ groups, as defined herein (including all embodiments thereof).

For the avoidance of doubt, groups forming part of structures representing $R^1$ (e.g. $R^x$, $R^y$ and $R^z$, and the carbon to which they are attached) may be optionally substituted as defined herein for $R^1$.

In further particular embodiments, $R^1$ may represent

wherein $R^x$, $R^y$ and $R^z$ each independently represent H or $C_{1-11}$ alkyl, as appropriate.

In more particular embodiments, $R^1$ may represent

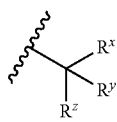

wherein $R^x$ and $R^z$ each independently represent H or $C_{1-11}$ alkyl, as appropriate (e.g. n-propyl). In particular embodiments, when $R^x$ and $R^z$ are not H, they may be the same.

In alternative embodiments, when $R^x$ and $R^z$ are not H, they may be different (e.g. $R^x$ may be propyl and $R^z$ methyl, i.e. $R^1$ may be 2-pentyl).

In such instances, the skilled person will recognize that the carbon to which $R^x$ and $R^z$ is a stereocentre and therefore $R^1$ may be depicted as

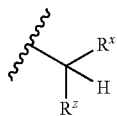

The skilled person will understand that such a stereocentre may be referred to as being in either the (R) or (S) configuration, depending on whether $R^x$ or $R^z$ is assigned a higher priority (according to the Cahn-Ingold-Prelog system, as understood by those skilled in the art).

In particular such embodiments, $R^x$ and $R^z$ may each independently represent $C_{1-11}$ alkyl, wherein $R^x$ is a larger alkyl group (i.e. has a greater number of carbons atoms forming said alkyl group) than $R^z$. For example, in such embodiments $R^z$ may represent $C_{1-2}$ alkyl and $R^x$ may represent $C_{3-10}$ alkyl.

In particular such embodiments, $R^1$ is a group of structure

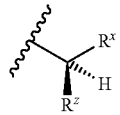

such as wherein $R^z$ may represent $C_{1-2}$ alkyl and $R^x$ may represent $C_{3-8}$ alkyl.

In particular such embodiments:
$R^z$ represents methyl; and/or (e.g. and)
$R^x$ represents n-propyl.

In alternative such embodiments, $R^1$ is a group of structure

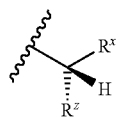

such as wherein $R^z$ may represent $C_{1-2}$ alkyl and $R^x$ may represent $C_{3-8}$ alkyl.

In particular such alternative embodiments:
$R^z$ represents methyl; and/or (e.g. and)
$R^x$ represents n-propyl.

In further alternative embodiments, $R^1$ may represent

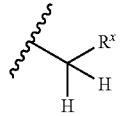

wherein $R^x$ represents H or $C_{3-9}$ alkyl, such as n-propyl (i.e. $R^1$ may be n-butyl).

The skilled person will understand that the prefixes "n-", "sec-" and "tert-" when applied to alkyl groups indicate the terms "normal", "secondary" and "tertiary". The term "normal" indicates a linear alkyl group where the point of attachment of the group to the rest of a molecule is through a carbon atom at the end of the carbon chain and thus that that carbon atom is bound to one other carbon atom. The term "secondary" indicates that the point of attachment of the rest of the molecule to the alkyl group is through a carbon atom adjacent to the end of the carbon chain and thus that that carbon is itself bound to two other carbon atoms. The term "tertiary" indicates that the point of attachment of the alkyl group to the rest of a molecule is through a carbon atom that is bound to three other carbon atoms.

In particular embodiments of the first aspect of the invention, each $R^2$ and $R^3$ independently represents H or $C_{1-2}$ alkyl (e.g. methyl).

In further embodiments of the first aspect of the invention, each $R^2$ and $R^3$ independently represents H, methyl or ethyl (e.g. methyl).

In more particular embodiments, $R^2$ represents H and $R^3$ represents H or methyl.

In yet more particular embodiments, $R^2$ and $R^3$ each represent H.

In certain embodiments, m represents 1, 2 or 3. For example, m may represent 1 or 2.

In certain embodiments of the compounds of the invention, when m represents 3, the F atoms are located in the 2-, 3- and 4-positions or the 3-, 4-, 5 positions.

In certain embodiments of the compounds of the invention, when m represents 2, the F atoms are located in the 2- and 4-positions, or the 3- and 4-positions, or the 3- and 5-positions (e.g. the 3- and 4-positions).

In further embodiments, when m represents 2, the F atoms are located in the 2- and 3-positions, 2- and 4-positions, or the 3- and 4-positions, or the 3- and 5-positions.

In certain embodiments of the compounds of the invention, when m represents 1, the F atom is located the 3- or 4-position (e.g. the 3-position).

For example, the skilled person will understand that, in certain embodiments, when m represents 2, the F atoms are located in the 3- and 4-positions, and when m represents 1, the F atom is located the 3- or 4-position (e.g. the 3-position).

In further embodiments, when m represents 1, the F atom is located the 2-, 3- or 4-position (e.g. the 3-position).

In certain embodiments of the compounds of the invention, wherein n represents 0, 1, 2 or 3, each X independently represents Cl, Br, $R^a$, —CN, —$N_3$, —N($R^b$)$R^c$, —$NO_2$ or —$OR^d$, wherein $R^a$ represents $C_{1-4}$ alkyl optionally substituted by one or more F, and wherein $R^b$, $R^c$ and $R^d$ each independently represent H or $C_{1-4}$ alkyl optionally substituted by one or more F.

For example, each X may independently represent Cl, Br, $R^a$, —CN, —$N_3$, —N($R^b$)$R^c$, —$NO_2$ or —$OR^d$, wherein $R^a$ represents $C_{1-4}$ alkyl optionally substituted by one or more F, and $R^b$, $R^c$ and $R^d$ each independently represent H or $C_{1-4}$ alkyl optionally substituted by one or more F or =O.

In further embodiments, each X may independently represent Cl, Br, $R^a$, —CN, —$N_3$, —N($R^b$)$R^c$, —$NO_2$ or —$OR^d$, wherein $R^a$ represents $C_{1-4}$ alkyl optionally substituted by one or more F, and $R^b$ and $R^c$ each independently represent H or $C_{1-4}$ alkyl optionally substituted by =O, and $R^d$ represents H or $C_{1-4}$ alkyl optionally substituted by one or more F.

In more particular embodiments, each X independently represents Cl, $R^a$, —N($R^b$)$R^c$, —CN or —OH, wherein $R^a$ represents $C_{1-4}$ alkyl (e.g. $C_{1-2}$ alkyl) optionally substituted by one or more F (for example $R^a$ represents —$CH_3$, —$CHF_2$ or —$CF_3$ (e.g. —$CF_3$)), and $R^b$ and $R^c$ each independently represent H or $C_{1-4}$ alkyl optionally substituted by =O (for example $R^c$ represents —C(O)$CH_3$).

In yet more particular embodiments, each X independently represents Cl, $R^a$, —N($R^b$)$R^c$ or —OH, wherein $R^a$ represents $C_{1-2}$ alkyl optionally substituted by one or more F (for example $R^a$ represents —$CHF_2$ or —$CF_3$ (e.g. —$CF_3$)), and $R^b$ and $R^c$ each independently represent H or $C_{1-4}$ alkyl optionally substituted by =O (for example $R^c$ represents —C(O)$CH_3$).

In further particular embodiments, each X independently represents Cl, $R^a$, —$NH_2$, —NHC(O)$CH_3$, —$CF_3$ or —OH, wherein $R^a$ represents $C_{1-2}$ alkyl optionally substituted by one or more F.

In yet further particular embodiments, each X independently represent Cl, —$NH_2$, —NHC(O)$CH_3$, —$CF_3$ or —OH. In a further embodiment, each X independently represents —$NH_2$, —NHC(O)$CH_3$ or —OH, such as —$NH_2$ or —NHC(O)$CH_3$ (e.g. —$NH_2$).

In some embodiments of the compounds of the invention, n represents 0, 1 or 2 (for example 1 or 2, e.g. 1).

In certain embodiments of the compounds of the invention, n represents 0, 1 or 2 (e.g. 0 or 1).

In particular embodiments of the compounds of the invention, n represents 1.

In alternative embodiments of the compounds of the invention, n represents 0.

In certain embodiments, wherein n represents 2, each X independently represents Cl, —$NH_2$, —NHC(O)$CH_3$, —$CF_3$ or —OH. In further certain embodiments, wherein n represents 2, each X independently represents —$NH_2$, —NHC(O)$CH_3$ or —OH. In such embodiments, the X groups may be located in the 2- and 3-positions, or the 2- and 4-positions or 3- and 5-positions (e.g. 2- and 3-positions) of the essential benzene ring.

In certain embodiments, wherein n represents 1, X represents Cl, $R^a$, —$NH_2$, —NHC(O)$CH_3$ or —OH wherein $R^a$ represents $C_{1-2}$ alkyl optionally substituted by one or more F (e.g. $CF_3$). In further certain embodiments, wherein n represents 1, X represents Cl, —$NH_2$, —NHC(O)$CH_3$ or —OH. In particular embodiments, wherein n represents 1, X represents —$NH_2$, —NHC(O)$CH_3$ or —OH. In such embodiments, the X group may be located in the 3-, 4- or 5-position of the essential benzene ring. In further such embodiments, the X group may also (or instead) be located in the 2-position of the essential benzene ring.

In certain embodiments, wherein n represents 1, X represents —$NH_2$ or —NHC(O)$CH_3$ (e.g. —$NH_2$). In such embodiments, the X group may be located in the 3- or 4-positions of the essential benzene ring. In further such embodiments, the X group may be located in the 2- or 3-position (e.g. the two position) of the essential benzene ring.

In certain embodiments, wherein n represents 1, X represents —OH. In such embodiments, the X group may be located in the 3-, 4- or 5-position of the essential benzene ring. In further such embodiments, the X group may be located in the 2- or 3-position (e.g. the two position) of the essential benzene ring.

In certain embodiments that may be mentioned, when n represents 2 or more (i.e. more than one X substituent is present), no more than one X may represent a group selected from —N($R^b$)$R^c$ and —$OR^d$ (particularly where $R^b$, $R^c$ and $R^d$ represent H).

In further embodiments:
m represents 1 or 2 (e.g. 1);
n represents 1;
X represents —$NH_2$, —NHC(O)$CH_3$ or —OH;
particularly where the F atoms are located in the 2-, 3-, 4- or 5-positions of the essential benzene ring; and
particularly where the X group is in the 3-, 4- and 5-positions of the essential benzene ring.

In particular embodiments that may be mentioned, the sum of m and n does not exceed 2.

In further embodiments, there is provided a compound of formula I, or a pharmaceutically acceptable salt thereof, wherein the essential benzene ring is unsubstituted in the 2-, 3-, 5- and 6-positions. For example, in certain embodiments the essential benzene ring is unsubstituted in the 5- and 6-positions.

In particular embodiments of the first aspect of the invention:
m represents 1;
the F atom is located in the 3- or 4-position (e.g. the 3-position) of the essential benzene ring; and
n represents 0.

In particular embodiments of the first aspect of the invention:

m represents 1;

the F atom is located in the 3-position of the essential benzene ring; and n represents 1;

X represents —NH$_2$, —NHC(O)CH$_3$ or —OH; and the X group is in the 4- or 5-positions of the essential benzene ring.

In particular embodiments of the first aspect of the invention:

m represents 1;

the F atom is located in the 4-position of the essential benzene ring; and n represents 1;

X represents —NH$_2$, —NHC(O)CH$_3$ or —OH; and the X group is in the 3-position of the essential benzene ring.

In particular embodiments of the first aspect of the invention:

m represents 2;

the F atoms are located in the 3- and 5-positions of the essential benzene ring; and n represents 0.

In particular embodiments of the first aspect of the invention:

m represents 2;

the F atoms are located in the 3- and 4-positions of the essential benzene ring; and n represents 0.

In particular embodiments of the first aspect of the invention:

m represents 2;

the F atoms are located in the 2- and 4-position of the essential benzene ring;

n represents 1;

X represents —NH$_2$, —NHC(O)CH$_3$ or —OH; and the X group is in the 3-position of the essential benzene ring.

For example, in a particular embodiment of the first aspect of the invention:

R$^1$ represents n-butyl;

R$^2$ and R$^3$ represent H;

m represents 1;

the F atom is located in the 4-position of the essential benzene ring;

n represents 1; and

X represents —NH$_2$ and is in the 3-position on the phenyl group to which it is attached.

Similarly, in a particular embodiment:

R$^1$ represents tert-butyl;

R$^2$ and R$^3$ represent H;

m represents 1; and the F atom is located in the 3-position of the essential benzene ring.

For the avoidance of doubt, when R$^1$ represents n-butyl, R$^2$ and R$^3$ represent H, m represents 1 and the F atom is in the 4-position of the essential benzene ring, and n represents 1, X represents —NH$_2$ and is in the 3-position on the essential benzene ring, the compound of formula I may be depicted as:

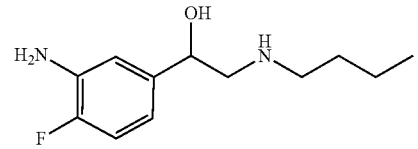 [SMILES: CCCCNCC(O)c1ccc(F)c(N)c1]

In further particular embodiments of the compounds of the invention, the compound of formula I is a compound of formula IA

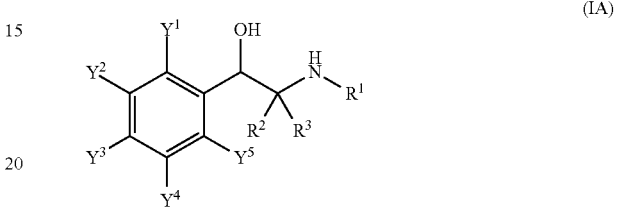

wherein R$^1$, R$^2$ and R$^3$ are as defined herein (for the avoidance of doubt, including all embodiments thereof), and Y$^1$, Y$^2$, Y$^3$, Y$^4$ and Y$^5$ each independently represent H, F or X, wherein X is as defined herein (for the avoidance of doubt, including all embodiments thereof), with the proviso that at least one of Y$^1$ to Y$^5$ represents F.

In certain embodiments, there is provided a compound of formula IA, wherein:

Y$^1$ and Y$^5$ each independently represent H or F; and

Y$^2$, Y$^3$ and Y$^4$ each independently represent H, F, R$^a$, —CN, —N$_3$, —N(R$^b$)R$^c$, —NO$_2$ or —OR$^d$, wherein R$^a$ represents C$_{1-4}$ alkyl optionally substituted by one or more F, and wherein R$^b$, R$^c$ and R$^d$ each independently represent H or C$_{1-4}$ alkyl optionally substituted by one or more F or =O, with the proviso that at least one of Y$^1$ to Y$^5$ represents F.

In particular embodiments, there is provided a compound of formula IA, wherein Y$^1$ and Y$^3$ represent F (e.g. wherein Y$^2$ represents X, such as —NH$_2$ or —NHC(O)CH$_3$, and Y$^4$ and Y$^5$ represent H).

In further embodiments, there is provided a compound of formula IA, wherein Y$^2$ represents F (e.g. wherein Y$^3$ represents X, such as —NH$_2$, and Y$^1$, Y$^4$ and Y$^5$ represent H, or wherein Y$^1$, Y$^3$, Y$^4$ and Y$^5$ represent H).

In further embodiments, there is provided a compound of formula IA, wherein either Y$^2$, Y$^3$, Y$^2$ and Y$^4$, or Y$^2$ and Y$^3$ represents F, and the remainder of Y$^1$ to Y$^5$ represents H.

In certain embodiments, there is provided a compound of formula IA, wherein one or both (e.g. one) of Y$^2$ or Y$^3$ represents a group selected from Cl, F and —OH (e.g. Cl or F, such as F), and the remainder of Y$^1$ to Y$^5$ represents H.

In particular embodiments:

Y$^1$ and Y$^5$ each represent H or F; and

Y$^2$, Y$^3$ and Y$^4$ each independently represent H, F, R$^a$, —CN, —N(R$^b$)R$^c$, or —OH, wherein R$^a$ represents C$_{1-2}$ alkyl optionally substituted by one or more F (for example, R$^a$ may represent —CH$_3$, —CF$_3$ or —CHF$_2$), and R$^b$ and R$^c$ each independently represent H or C$_{1-4}$ alkyl optionally substituted by =O (for example, R$^c$ may represent —C(O)CH$_3$), with the proviso that one or two of Y$^1$ to Y$^5$ represents F.

In further particular embodiments:
$Y^1$ and $Y^5$ each represent H; and
$Y^2$, $Y^3$ and $Y^4$ each independently represent H, F, —N($R^b$)$R^c$, —CN or —OH, wherein $R^b$ and
$R^c$ each independently represent H or $C_{1-4}$ alkyl optionally substituted by =O (for example,
$R^c$ may represent —C(O)CH$_3$),
with the proviso that one or two of $Y^2$, $Y^3$ and $Y^4$ represent F.

In more particular embodiments:
$Y^1$ and $Y^5$ each independently represent H or F; and $Y^2$, $Y^3$ and $Y^4$ each independently represent H, F, —NH$_2$, —NHC(O)CH$_3$ or —OH, with the proviso that one or two of $Y^2$, $Y^3$ and $Y^4$ represent F.

In alternative embodiments:
$Y^1$ represents H or F;
$Y^2$, $Y^3$ and $Y^4$ each independently represent F, $R^a$, —CN, —N$_3$, —N($R^b$)$R^c$, —NO$_2$ or —O$R^d$; wherein $R^a$ represents $C_{1-4}$ alkyl optionally substituted by one or more F, wherein $R^b$, $R^c$ and $R^d$ each independently represents H or $C_{1-4}$ alkyl optionally substituted by one or more F or =O; and
$Y^5$ represents H,
with the proviso that one of $Y^1$ to $Y^4$ represents F.

In further alternative embodiments:
$Y^1$ represents H or F;
$Y^2$, $Y^3$ and $Y^4$ each independently represent H, F, Cl, —N($R^b$)$R^c$ or —OH, wherein $R^b$ and $R^c$ each independently represent H or $C_{1-4}$ alkyl optionally substituted by =O.
$Y^5$ represents H,
with the proviso that one of $Y^1$ to $Y^4$ represents F.

In yet more particular embodiments:
$Y^1$ represents H or F;
$Y^2$, $Y^3$ and $Y^4$ each independently represent H, F, —NH$_2$, —NHC(O)CH$_3$ or —OH; and
$Y^5$ represents H,
with the proviso that one of $Y^1$ to $Y^4$ represents F.

In yet more particular embodiments:
$Y^1$, $Y^2$ and $Y^5$ each represent H; and
$Y^3$ and $Y^4$ each independently represent H, F, —NH$_2$, —NHC(O)CH$_3$ or —OH, with the proviso that one of $Y^1$ to $Y^4$ represents F.

In yet more particular embodiments:
$Y^1$, $Y^2$, $Y^3$ and $Y^5$ represents H; and
$Y^4$ represents F.

In yet more particular embodiments:
$Y^1$, $Y^2$, $Y^4$ and $Y^5$ represents H; and
$Y^3$ represents F.

In alternative embodiments:
$Y^1$, $Y^3$, $Y^4$ and $Y^5$ represents H; and
$Y^2$ represents F.

In more alternative embodiments:
$Y^1$ and $Y^5$ each represent H;
$Y^2$ and $Y^4$ each independently represent —NH$_2$, —NHC(O)CH$_3$ or —OH and
$Y^3$ represents F.

In yet more alternative embodiments:
$Y^1$ and $Y^5$ each represent H;
$Y^2$ and $Y^4$ each independently represent H or F; and
$Y^3$ represents —NH$_2$, —NHC(O)CH$_3$ or —OH.

In certain embodiments:
$Y^1$ and $Y^3$ each represent F; and
$Y^2$ represents —NH$_2$ or —NHC(O)CH$_3$; and
$Y^4$ and $Y^5$ each represent H.

In further certain embodiments:
$Y^1$, $Y^3$ and $Y^5$ represent H; and
$Y^2$ and $Y^4$ each represent F.

In alternative certain embodiments:
$Y^1$, $Y^4$ and $Y^5$ represent H; and
$Y^2$ and $Y^3$ each represent F.

The skilled person will understand that particular X groups (and the positions and number thereof, such as may correspond to $Y^1$ to $Y^5$ groups in compounds of formula IA) that may be mentioned include those present in the examples provided herein.

Similarly, the skilled person will understand that particular $R^1$, $R^2$ and $R^3$ groups that may be mentioned include those present in the examples provided herein.

For example, in a particular embodiment of the first aspect of the invention:
$R^1$ represents n-butyl or cyclopropylmethyl;
$R^2$ and $R^3$ represent H;
m represents 1;
n represent 0; and
the F atom is in the 4-position on the phenyl group to which it is attached (i.e. in a compound of formula IA, $Y^1$, $Y^2$, $Y^4$ and $Y^5$ represent H and $Y^3$ represents —F).

In an alternative example of a particular embodiment of the first aspect of the invention:
$R^1$ represents n-butyl or cyclopropylmethyl;
$R^2$ and $R^3$ represent H;
m represents 1;
n represent 0; and
the F atom is in the 3-position on the phenyl group to which it is attached (i.e. in a compound of formula IA, $Y^1$, $Y^3$, $Y^4$ and $Y^5$ represent H and $Y^2$ represents —F).

In a further example of a particular embodiment of the first aspect of the invention:
$R^1$ represents t-butyl;
$R^2$ and $R^3$ represent H;
m represents 1;
n represent 0; and
the F atom is in the 3-position on the phenyl group to which it is attached (i.e. in a compound of formula IA, $Y^1$, $Y^3$, $Y^4$ and $Y^5$ represent H and $Y^2$ represents —F).

Particular compounds of the first aspect of the invention that may be mentioned include the compounds of the examples provided herein, and pharmaceutically acceptable salts thereof. Thus, compounds of formula I that may be mentioned include:
2-(butylamino)-1-(3,5-difluorophenyl)ethan-1-ol
2-(butylamino)-1-(3,4-difluorophenyl)ethan-1-ol
1-(4-amino-3,5-difluorophenyl)-2-(butylamino)ethan-1-ol
N-(3-(2-(butylamino)-1-hydroxyethyl)-2,6-difluorophenyl) acetamide
1-(3-amino-2,4-difluorophenyl)-2-(butylamino)ethan-1-ol
1-(4-amino-3,5-difluorophenyl)-2-(butylamino)ethan-1-ol
and pharmaceutically acceptable salts thereof.

More particular compounds of formula I include:
2-(butylamino)-1-(3,5-difluorophenyl)ethan-1-ol
2-(butylamino)-1-(3,4-difluorophenyl)ethan-1-ol
and pharmaceutically acceptable salts thereof.

Certain particular compounds of formula I include:
1-(4-amino-3,5-difluorophenyl)-2-(butylamino)ethan-1-ol
N-(3-(2-(butylamino)-1-hydroxyethyl)-2,6-difluorophenyl) acetamide
1-(3-amino-2,4-difluorophenyl)-2-(butylamino)ethan-1-ol
1-(4-amino-3,5-difluorophenyl)-2-(butyl amino)ethan-1-ol
and pharmaceutically acceptable salts thereof.

Certain compounds of formula I that may be mentioned include:
2-(Butylamino)-1-(4-fluorophenyl)ethan-1-ol
2-(Butylamino)-1-(4-fluorophenyl)ethan-1-ol
2-(Butylamino)-1-(3-fluorophenyl)ethan-1-ol
2-(tert-Butylamino)-1-(3-fluorophenyl)ethan-1-ol 1-(4-Fluorophenyl)-2-((pentan-2-yl)amino)ethan-1-ol
and pharmaceutically acceptable salts thereof.

Further compounds of formula I that may be mentioned include:
1-(3-Fluorophenyl)-2-((2-methylpentan-2-yl)amino)ethan-1-ol
2-(tert-Butylamino)-1-(2,3-difluorophenyl)ethan-1-ol
2-(Butylamino)-1-(2,3-difluorophenyl)ethan-1-ol
2-(tert-Butylamino)-1-(2-fluorophenyl)ethan-1-ol
2-(Butylamino)-1-(2-fluorophenyl)ethan-1-ol
2-(2-(tert-Butylamino)-1-hydroxyethyl)-5-fluorophenol
2-(2-(Butylamino)-1-hydroxyethyl)-5-fluorophenol
1-(3-fluorophenyl)-2-((1-methylcyclobutyl)amino)ethan-1-ol
1-(3-fluorophenyl)-2-((1-methylcyclopropyl)amino)ethan-1-ol
5-(2-(tert-Butylamino)-1-hydroxyethyl)-2-fluorophenol
5-(2-(Butylamino)-1-hydroxyethyl)-2-fluorophenol
3-(2-(tert-Butylamino)-1-hydroxyethyl)-2-fluorophenol
3-(2-(Butylamino)-1-hydroxyethyl)-2-fluorophenol
1-(3-Amino-2-fluorophenyl)-2-(tert-butylamino)ethan-1-ol
1-(3-Amino-2-fluorophenyl)-2-(butylamino)ethan-1-ol
1-(3-Fluorophenyl)-2-(neopentylamino)ethan-1-ol
1-(3-fluorophenyl)-2-((1-(trifluoromethyl)cyclopropyl)amino)ethan-1-ol
1-(3-amino-2,4-difluorophenyl)-2-(tert-butylamino)ethan-1-ol
2-(tert-butylamino)-1-(3-fluoro-2-methylphenyl)ethan-1-ol
and pharmaceutically acceptable salts thereof.

As described herein, compounds of the first aspect of the invention may also contain one or more asymmetric carbon atoms and may therefore exhibit optical and/or diastereoisomerism. Moreover, it has been found that certain such optical and/or diastereoisomers may show increased utility in the treatment of hyperglycaemia or disorders characterized by hyperglycaemia (such as type 2 diabetes), as described herein.

In a particular embodiment of the first aspect of the invention, the compound of formula I is such that the carbon substituted with the essential —OH group is in the (R) configuration, as understood by those skilled in the art.

Thus, in a particular embodiment, the compound of formula I is a compound of formula IB

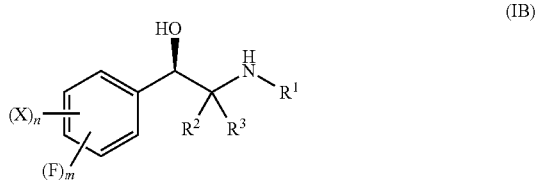

(IB)

wherein n, X, $R^1$, $R^2$ and $R^3$ are as described herein (i.e. as described in the first aspect of the invention, including all embodiments and particular features, and combinations thereof).

In particular embodiments, there is provided a compound of formula IB wherein:
m represents 1;
n represents 0;
$R^1$ represents $C_{4-8}$ alkyl (e.g. $C_4$ alkyl, such as n-butyl); and/or (e.g. and)
$R^2$ and $R^3$ both represent H.

In more particular embodiments, there is provided a compound of formula IB wherein:

n represents 1 and the F atom is in the 4-position of the phenyl group;
$R^1$ represents $C_{4-8}$ alkyl (e.g. $C_4$ alkyl, such as n-butyl); and
$R^2$ and $R^3$ both represent H.

In particular embodiments that may be mentioned, the essential —OH group in compounds of formula I is in the (R) configuration.

In a yet more particular embodiment, the compound of formula I (or the compound of formula IA or IB) is a compound of formula IC

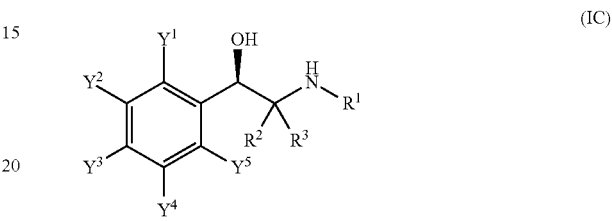

(IC)

wherein $Y^1$, $Y^2$, $Y^3$, $Y^4$, $Y^5$, $R^1$, $R^2$ and $R^3$ are as described herein (i.e. as described in the first aspect of the invention, including all embodiments and particular features, and combinations thereof).

For example, there is provided a compound of formula IC wherein:
$Y^1$, $Y^4$ and $Y^5$ each represent H;
one of $Y^2$ and $Y^3$ represents F and the other represents H;
$R^1$ represents $C_{4-5}$ alkyl; and/or
$R^2$ and $R^3$ both represent H.

As described herein, particular compounds of the first aspect of the invention that may be mentioned include the compounds of the examples provided herein, and pharmaceutically acceptable salts thereof. Thus, compounds of formula IB or IC that may be mentioned include:
(R)-2-(Butylamino)-1-(4-fluorophenyl)ethan-1-ol
(R)-2-(Butylamino)-1-(3-fluorophenyl)ethan-1-ol
(R)-2-(tert-Butylamino)-1-(3-fluorophenyl)ethan-1-ol
(R)-1-(4-fluorophenyl)-2-(((R)-pentan-2-yl)amino)ethan-1-ol
(R)-1-(4-fluorophenyl)-2-(((S)-pentan-2-yl)amino)ethan-1-ol
(R)-1-(3-fluorophenyl)-2-(((R)-pentan-2-yl)amino)ethan-1-ol
(R)-1-(3-fluorophenyl)-2-(((S)-pentan-2-yl)amino)ethan-1-ol
and pharmaceutically acceptable salts thereof.

More particular compounds of formula I (e.g. compounds of formula IB or IC) include:
(R)-2-(Butylamino)-1-(4-fluorophenyl)ethan-1-ol
(R)-2-(Butylamino)-1-(3-fluorophenyl)ethan-1-ol
(R)-2-(tert-Butylamino)-1-(3-fluorophenyl)ethan-1-ol
and pharmaceutically acceptable salts thereof.

Certain particular compounds of formula I include:
(R)-1-(4-fluorophenyl)-2-(((R)-pentan-2-yl)amino)ethan-1-ol
(R)-1-(4-fluorophenyl)-2-(((S)-pentan-2-yl)amino)ethan-1-ol
(R)-1-(3-fluorophenyl)-2-(((R)-pentan-2-yl)amino)ethan-1-ol
(R)-1-(3-fluorophenyl)-2-(((S)-pentan-2-yl)amino)ethan-1-ol
and pharmaceutically acceptable salts thereof.

Further compounds of formula I (e.g. compounds of formula IB or IC) that may be mentioned include:
(R)-1-(3-Fluorophenyl)-2-((2-methylpentan-2-yl)amino) ethan-1-ol
(R)-2-(tert-Butylamino)-1-(2,3-difluorophenyl)ethan-1-ol
(R)-2-(Butylamino)-1-(2,3-difluorophenyl)ethan-1-ol
(R)-2-(tert-Butylamino)-1-(2-fluorophenyl)ethan-1-ol
(R)-2-(Butylamino)-1-(2-fluorophenyl)ethan-1-ol
(R)-2-(2-(tert-Butylamino)-1-hydroxyethyl)-5-fluorophenol
(R)-2-(2-(Butylamino)-1-hydroxyethyl)-5-fluorophenol
(R)-1-(3-fluorophenyl)-2-((1-methylcyclobutyl)amino) ethan-1-ol
(R)-1-(3-fluorophenyl)-2-((1-methylcyclopropyl)amino) ethan-1-ol
(R)-5-(2-(tert-Butylamino)-1-hydroxyethyl)-2-fluorophenol
(R)-5-(2-(Butylamino)-1-hydroxyethyl)-2-fluorophenol
(R)-3-(2-(tert-Butylamino)-1-hydroxyethyl)-2-fluorophenol
(R)-3-(2-(Butylamino)-1-hydroxyethyl)-2-fluorophenol
(R)-1-(3-Amino-2-fluorophenyl)-2-(tert-butylamino)ethan-1-ol
(R)-1-(3-Amino-2-fluorophenyl)-2-(butylamino)ethan-1-ol
(R)-1-(3-Fluorophenyl)-2-(neopentylamino)ethan-1-ol
(R)-1-(3-fluorophenyl)-2-((1-(trifluoromethyl)cyclopropyl) amino)ethan-1-ol
(R)-1-(3-amino-2,4-difluorophenyl)-2-(tert-butylamino) ethan-1-ol
(R)-2-(tert-butylamino)-1-(3-fluoro-2-methylphenyl)ethan-1-ol
and pharmaceutically acceptable salts thereof.

In certain embodiments that may be mentioned, the compound of the invention is not a compound selected from the list consisting of:
(R)-2-(tert-butylamino)-1-(3-fluorophenyl)ethan-1-ol; and
(R)-1-(4-fluorophenyl)-2-((-pentan-2-yl)amino)ethan-1-ol.

In further embodiments that may be mentioned, the compound of the invention is not a compound selected from the list consisting of:
(R)-2-(tert-butylamino)-1-(3-fluorophenyl)ethan-1-ol; and
(R)-1-(4-fluorophenyl)-2-((-pentan-2-yl)amino)ethan-1-ol, and pharmaceutically acceptable salts thereof.

The skilled person will understand that references to a specific steroisomer of a compound of formula I (e.g. in the case of compounds of formula I, where the carbon substituted by the essential —OH group is in the (R) configuration, as represented by compounds of formula IB and formula IC) will refer to the specific stereoisomer being present in the substantial absence of the corresponding opposite stereoisomer (e.g. in the case of compounds of formula I, where the carbon substituted by the essential —OH group is in the (S) configuration).

For example, references to a compound of formula IC being present in the substantial absence of the corresponding opposite steroisomer (i.e. in the (S) configuration) will refer to the substantial absence of the corresponding compound as depicted below.

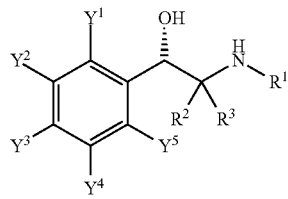

As used herein, references to the substantial absence of the other stereoisomers (e.g. the corresponding opposite stereoisomer) will refer to the desired stereoisomer (e.g. in the case of compounds of formula I, where the carbon substituted by the essential —OH group is in the (R) configuration) being present at a purity of at least 80% (e.g. at least 90%, such as at least 95%) relative to the other stereoisomers (e.g. in the case of compounds of formula I, where the carbon substituted by the essential —OH group is in the (S) configuration). Alternatively, in such instances, compounds may be indicated to be present in the substantial absence of the compound in the other configuration (i.e. (S) configuration), which may indicate that the compound in the relevant configuration is present in an enantiomeric excess (e.e.) or diastereomeric excess (d.e.), as appropriate, of at least 90% (such as at least 95%, at least 98% or, particularly, at least 99%, for example at least 99.9%).

For the avoidance of doubt, compounds referred to as having a specific stereochemistry at a defined position (e.g. in the case of compounds of formula I, the carbon substituted by the essential —OH group being in the (R) configuration) may also have stereochemistry at one or more other positions, and so may exist as mixtures of enantiomers or diastereoisomers in relation to the stereochemistry at those positions.

Medical Uses

As indicated herein, the compounds of the invention, and therefore compositions and kits comprising the same, are useful as pharmaceuticals.

Thus, according to a second aspect of the invention there is provided a compound of the first aspect of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof) and pharmaceutically acceptable salts thereof.

As indicated herein, the compounds of the invention may be of particular use in treating hyperglycaemia or a disorder characterized by hyperglycaemia.

Thus, in a third aspect of the invention, there is provided a compound of the first aspect of the invention, as hereinbefore defined, for use in the treatment of hyperglycaemia or a disorder characterized by hyperglycaemia.

In an alternative third aspect of the invention, there is provided the use of a compound of formula I, or a pharmaceutically acceptable salt thereof, in the manufacture of a medicament for use in the treatment of hyperglycaemia or a disorder characterized by hyperglycaemia.

In a further alternative third aspect of the invention, there is provided a method of treating hyperglycaemia or a disorder characterized by hyperglycaemia comprising administering to a patient in need thereof a therapeutically effective amount of a compound of formula I, or a pharmaceutically acceptable salt thereof.

For the avoidance of doubt, the term "hyperglycaemia" as used herein will be understood by those skilled in the art to refer to a condition wherein an excessive amount of glucose circulates in blood plasma of the subject experiencing the same. In particular, it may refer to a subject (e.g a human subject) having blood glucose levels higher than about 10.0 mmol/L (such as higher than about 11.1 mmol/L, e.g. higher than about 15 mmol/L), although it may also refer to a subject (e.g a human subject) having blood glucose levels higher than about 7 mmol/L for an extended period of time (e.g. for greater than 24 hours, such as for greater than 48 hours).

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of type 2 diabetes, the term may refer to achieving a reduction of blood glucose levels. In particular embodiments, in the case of treating hyperglycaemia or conditions characterised by hyperglycaemia, the term may refer to achieving a reduction of blood glucose levels (for example, to or below about 10.0 mmol/mL (e.g. to levels in the range of from about 4.0 mmol/L to about 10.0 mmol/L), such as to or below about 7.5 mmol/mL (e.g. to levels in the range of from about 4.0 mmol/L to about 7.5 mmol/L) or to or below about 6 mmol/mL (e.g. to levels in the range of from about 4.0 mmol/L to about 6.0 mmol/L)).

As used herein, references to patients will refer to a living subject being treated, including mammalian (e.g. human) patients. Thus, in particular embodiments of the first aspect of the invention, the treatment is in a mammal (e.g. a human).

As used herein, the term therapeutically effective amount will refer to an amount of a compound that confers a therapeutic effect on the treated patient. The effect may be objective (i.e. measurable by some test or marker) or subjective (i.e. the subject gives an indication of and/or feels an effect).

Although compounds of the first aspect of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the first aspect of the invention are included within the scope of the invention.

For the avoidance of doubt, the compounds of the first aspect of the invention are useful because they possess pharmacological activity, and/or are metabolised in the body following oral or parenteral administration to form compounds that possess pharmacological activity. In particular, as described herein, compounds of the first aspect of the invention are useful in the treatment of hyperglycaemia or disorders characterized by hyperglycaemia (such as type 2 diabetes), which terms will be readily understood by one of skill in the art (as described herein).

In a particular embodiment, the treatment is of a disorder (which may also be referred to as a condition or disease) characterised by hyperglycaemia.

In particular embodiments, compounds of the invention (i.e. compounds of formula I, including all embodiments thereof) are for use in the treatment of type 2 diabetes (or useful in the manufacture of a medicament for such treatment, or useful in a method for such treatment, as described herein).

In particular embodiments of the first aspect of the invention, the disorder is type 2 diabetes, such as type 2 diabetes of a sub-type selected from the list consisting of maturity-onset diabetes in the young (MODY), ketosis-prone diabetes in adults, latent autoimmune diabetes of adults (LADA), and gestational diabetes.

In further particular embodiments, the treatment of type 2 diabetes is in a non-obese patient.

For the avoidance of doubt, the skilled person will understand that patients with a Body Mass Index (BMI) of greater than 30 are considered to be obese.

In particular embodiments, the treatment may be of hyperglycaemia in a patient who is at risk of developing type 2 diabetes, which condition may be defined as pre-diabetes. Thus, compounds of the invention may be useful in the prevention of type 2 diabetes (e.g. in a patient having pre-diabetes).

As used herein, the term prevention (and, similarly, preventing) includes references to the prophylaxis of the disease or disorder (and vice-versa). As such, references to prevention may also be references to prophylaxis, and vice versa. In particular, the term may refer to achieving a reduction in the likelihood of the patient (or healthy subject) developing the condition (for example, at least a 10% reduction, such as at least a 20%, 30% or 40% reduction, e.g. at least a 50% reduction).

In more particular embodiments, the type 2 diabetes is characterised by the patient displaying severe insulin resistance (SIR).

In further embodiments, the treatment may be of hyperglycaemia in a patient having type 1 diabetes. Thus, compounds of the invention may be useful in the treatment of hyperglycaemia in type 1 diabetes.

The skilled person will understand that compounds of the invention may be useful in treating hyperglycaemia in patients having impaired insulin production, such as in patients having cystic fibrosis. Thus, in further embodiments, the disorder characterized by hyperglycaemia is cystic fibrosis-related diabetes.

In particular embodiments that may be mentioned, the disorder characterised by hyperglycaemia is (or is characterized by) severe insulin resistance (SIR), which may be understood by those in the art to refer to disorders wherein typically the subject has normal, or in some cases increased, insulin production but significantly reduced insulin sensitivity. In particular instances, such patients may be non-obese (e.g. being of a healthy weight). Thus, in particular embodiments, such treatments are performed in patients who are not defined as being obese (e.g. in patients who are defined as being of a healthy weight).

For example, SIR may be identified in a patient based in said patient having fasting insulin >150 pmol/L and/or a peak insulin on glucose tolerance testing of >1,500 pmol/L, particularly in individuals with a BMI <30 kg/m$^2$ (which patient may otherwise have normal glucose tolerance).

More particularly, SIR may be characterised by the patient having no significant response to the presence of insulin, which may result from a defect (e.g. a genetic defect) in the function of the insulin receptor.

Particular disorders that may be characterised by SIR include: Rabson-Mendenhall syndrome, Donohue's syndrome (leprechaunism), Type A and Type B syndromes of insulin resistance, the HAIR-AN (hyperandrogenism, insulin resistance, and acanthosis *nigricans*) syndromes, pseudoacromegaly, and lipodystrophy.

More particular disorders that may be characterised by SIR include Donohue's syndrome and Type A syndrome of insulin resistance and, yet more particularly, Rabson-Mendenhall syndrome.

The skilled person will understand that treatment with compounds of the first aspect of the invention may further comprise (i.e. be combined with) further (i.e. additional/ other) treatment(s) for the same condition. In particular, treatment with compounds of the invention may be combined with other means for the treatment of type 2 diabetes, such as treatment with one or more other therapeutic agent that is useful in the treatment of type 2 diabetes as known to those skilled in the art, such as therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that:
 (i) are capable of reducing blood sugar levels; and/or
 (ii) are insulin sensitizers; and/or
 (iii) enhance insulin release,
 all of which are described herein below.

In alternative embodiments, compounds of the first aspect of the invention (i.e. compounds of the invention) may be useful in the treatment of a non-alcoholic fatty liver disease (NAFLD).

Non-alcoholic fatty liver disease (NAFLD) is defined by excessive fat accumulation in the form of triglycerides (steatosis) in the liver (designated as an accumulation of greater than 5% of hepatocytes histologically). It is the most common liver disorder in developed countries (for example, affecting around 30% of US adults) and most patients are asymptomatic. If left untreated, the condition may progressively worsen and may ultimately lead to cirrhosis of the liver. NAFLD is particularly prevalent in obese patients, with around 80% thought to have the disease.

A sub-group of NAFLD patients (for example, between 2 and 5% of US adults) exhibit liver cell injury and inflammation in addition to excessive fat accumulation. This condition, designated as non-alcoholic steatohepatitis (NASH), is virtually indistinguishable histologically from alcoholic steatohepatitis. While the simple steatosis seen in NAFLD does not directly correlate with increased short-term morbidity or mortality, progression of this condition to NASH dramatically increases the risks of cirrhosis, liver failure and hepatocellular carcinoma. Indeed, NASH is now considered to be one of the main causes of cirrhosis (including cryptogenic cirrhosis) in the developed world.

The exact cause of NASH has yet to be elucidated, and it is almost certainly not the same in every patient. It is most closely related to insulin resistance, obesity, and the metabolic syndrome (which includes diseases related to diabetes mellitus type 2, insulin resistance, central (truncal) obesity, hyperlipidaemia, low high-density lipoprotein (HDL) cholesterol, hypertriglyceridemia, and hypertension). However, not all patients with these conditions have NASH, and not all patients with NASH suffer from one of these conditions. Nevertheless, given that NASH is a potentially fatal condition, leading to cirrhosis, liver failure and hepatocellular carcinoma, there exists a clear need for an effective treatment.

In particular embodiments, compounds of the invention (i.e. compounds of formula I, including all embodiments thereof) are for use in the treatment of a non-alcoholic fatty liver disease (or useful in the manufacture of a medicament for such treatment, or useful in a method for such treatment, as described herein).

The process by which the triglyceride fat accumulates in liver cells is called steatosis (i.e. hepatic steatosis). The skilled person will understand that the term "steatosis" encompasses the abnormal retention of fat (i.e. lipids) within a cell. Thus, in particular embodiments of the first aspect of the invention, the treatment or prevention is of a fatty liver disease which is characterized by steatosis.

During steatosis, excess lipids accumulate in vesicles that displace the cytoplasm of the cell. Over time, the vesicles can grow large enough to distort the nucleus, and the condition is known as macrovesicular steatosis. Otherwise, the condition may be referred to as microvesicular steatosis. Steatosis is largely harmless in mild cases; however, large accumulations of fat in the liver can cause significant health issues. Risk factors associated with steatosis include diabetes mellitus, protein malnutrition, hypertension, obesity, anoxia, sleep apnea and the presence of toxins within the cell.

As described herein, fatty liver disease is most commonly associated with alcohol or a metabolic syndrome (for example, diabetes, hypertension, obesity or dyslipidemia). Therefore, depending on the underlying cause, fatty liver disease may be diagnosed as alcohol-related fatty liver disease or non-alcoholic fatty liver disease (NAFLD).

Particular diseases or conditions that are associated with fatty liver disease that are not related to alcohol include metabolic conditions such as diabetes, hypertension, obesity, dyslipidemia, abetalipoproteinemia, glycogen storage diseases, Weber-Christian disease, acute fatty liver of pregnancy, and lipodystrophy. Other non-alcohol related factors related to fatty liver diseases include malnutrition, total parenteral nutrition, severe weight loss, refeeding syndrome, jejunoileal bypass, gastric bypass, polycystic ovary syndrome and diverticulosis.

The compounds of the invention have been found to be particularly useful in the treatment or prevention of NAFLD, which may be referred to as a fatty liver disease which is not alcohol related. A fatty liver disease which is "not alcohol related" may be diagnosed wherein alcohol consumption of the patient is not considered to be a main causative factor. A typical threshold for diagnosing a fatty liver disease as "not alcohol related" is a daily consumption of less than 20 g for female subjects and less than 30 g for male subjects.

If left untreated, subjects suffering from fatty liver disease may begin to experience inflammation of the liver (hepatitis). It has been postulated that one of the possible causes of this inflammation may be lipid peroxidative damage to the membranes of the liver cells. Inflammation of a fatty liver can lead to a number of serious conditions and it is therefore desirable to treat or prevent fatty liver disease before inflammation occurs. Thus, in particular embodiments of the first aspect of the invention, the treatment or prevention is of a NAFLD which is associated with inflammation.

Non-alcoholic steatohepatitis (NASH) is the most aggressive form of NAFLD, and is a condition in which excessive fat accumulation (steatosis) is accompanied by inflammation of the liver. If advanced, NASH can lead to the development of scar tissue in the liver (fibrosis) and, eventually, cirrhosis. As described above, the compounds of the invention have been found to be useful in the treatment or prevention of NAFLD, particularly when accompanied by inflammation of the liver. It follows that the compounds of the invention are also useful in the treatment or prevention of NASH. Therefore, in a further embodiment of the first aspect of the invention, the treatment or prevention is of non-alcoholic steatohepatitis (NASH).

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of a fatty liver disease, as described herein, such as treatment with one or more other therapeutic agent that is useful in the treatment of a fatty liver disease as known to those skilled in the art; for example, therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that are capable of reducing the level of fat (e.g. triglycerides) in the liver.

References to treatment of a fatty liver disease may refer to achieving a therapeutically significant reduction of fat (e.g. triglycerides levels) in liver cells (such as a reduction of at least 5% by weight, e.g. a reduction of at least 10%, or at least 20% or even 25%).

Pharmaceutical Compositions

As described herein, compounds of the first aspect of the invention (i.e. compounds of the invention) are useful as pharmaceuticals. Such compounds may be administered alone or may be administered by way of known pharmaceutical compositions/formulations.

In a fourth aspect of the invention, there is provided a pharmaceutical composition comprising a compound as defined in the second or third aspect of the invention, and optionally one or more pharmaceutically acceptable adjuvant, diluent and/or carrier.

The skilled person will understand that references herein to compounds of the first aspect of the invention being for particular uses (and, similarly, to uses and methods of use relating to compounds of the invention) may also apply to pharmaceutical compositions comprising compounds of the invention as described herein.

In a fifth aspect of the invention, there is provided a pharmaceutical composition for use in the treatment of hyperglycaemia or a disorder characterized by hyperglycaemia (as defined herein, such as type 2 diabetes) comprising a compound as defined in the first aspect of the invention, and optionally one or more pharmaceutically acceptable adjuvant, diluent and/or carrier.

In an alternative fifth aspect of the invention, there is provided a pharmaceutical composition for use in the treatment or prevention of a non-alcoholic fatty liver disease, as defined herein.

The skilled person will understand that compounds of the first aspect of the invention may act systemically and/or locally (i.e. at a particular site).

The skilled person will understand that compounds and compositions as described in the first to fifth aspects of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form. Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments of the fourth and fifth aspects of the invention, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The skilled person will understand that compounds of the invention, and pharmaceutically-acceptable salts thereof, may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 10 mg, 20 mg, 30 mg or 40 mg twice daily, or 10 µg, 20 µg, 30 µg or 40 µg twice daily).

In any event, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

As described herein above, the skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of hyperglycaemia or a disorder characterized by hyperglycaemia (as defined herein, such as type 2 diabetes), such as treatment with one or more other therapeutic agent that is useful in the treatment of hyperglycaemia or a disorder characterized by hyperglycaemia (as defined herein, such as type 2 diabetes).

In particular embodiments of the fourth and fifth aspects of the invention, the pharmaceutical composition may further comprise one or more additional (i.e. other) therapeutic agent.

In more particular embodiments, the one or more additional therapeutic agent is an agent for the treatment of type 2 diabetes as known to those skilled in the art, such as metformin, sulfonylureas (e.g. carbutamide, acetohexamide, chlorpropamide, tolbutamide. glipizide (glucotrol), gliclazide, glibenclamide, glyburide (Micronase), glibornuride, gliquidone, glisoxepide, glyclopyramide, glimepiride (Amaryl), glimiprime, JB253 or JB558), thiazolidinediones (e.g. pioglitazone, rosiglitazone (Avandia), lobeglitazone (Duvie) and troglitazone (Rezulin)), dipeptidyl peptidase-4 inhibitors (e.g. sitagliptin, vildagliptin, saxagliptin, linagliptin, anagliptin, teneligliptin, alogliptin, trelagliptin, gemigliptin, dutogliptin and omarigliptin), SGLT2 inhibitors (e.g. dapagliflozin, empagliflozin, canagliflozin, ipragliflozin, tofogliflozin, sergliflozin etabonate, remogliflozin etabonate, and ertugliflozin), and glucagon-like peptide-1 (GLP-1) analogues.

The skilled person will understand that combinations of therapeutic agents may also described as a combination product and/or provided as a kit-of-parts.

In a sixth aspect of the invention, there is provided a combination product comprising:

(A) a compound as defined in the first aspect of the invention; and (B) one or more additional therapeutic agent, wherein each of components (A) and (B) is formulated in admixture, optionally with one or more a pharmaceutically-acceptable adjuvant, diluent or carrier.

In a seventh aspect of the invention, there is provided a kit-of-parts comprising:

(a) a compound as defined in the first aspect of the invention, (or a pharmaceutical composition comprising the same) or a pharmaceutical composition as defined in the fourth or fifth aspect of the invention; and (b) one or more other therapeutic agent, optionally in admixture with one or more pharmaceutically-acceptable adjuvant, diluent or carrier, which components (a) and (b) are each provided in a form that is suitable for administration in conjunction with the other.

In particular embodiments (e.g. of the sixth and seventh aspects of the invention), the additional therapeutic agent is a therapeutic agent that is useful for the treatment of hyperglycaemia or a disorder characterized by hyperglycaemia (e.g. type 2 diabetes), as known to those skilled in the art (such as those described herein).

For example, in particular embodiments of the fourth to seventh aspects of the invention, the additional therapeutic agent is an agent that:

(i) is capable of reducing blood sugar levels; and/or (ii) is an insulin sensitizer; and/or (iii) is able to enhance insulin release, which agents will be readily identified by those skilled in the art and include, in particular, such therapeutic agents that are commercially available (e.g. agents that the subject of a marketing authorization in one or more territory, such as a European or US marketing authorization).

The skilled person will understand that references to therapeutic agents capable of reducing blood glucose levels may refer to compounds capable of reducing levels of blood by at least 10% (such as at least 20%, at least 30% or at least 40%, for example at least 50%, at least 60%, at least 70% or at least 80%, e.g. at least 90%) when compared to the blood glucose levels prior to treatment with the relevant compound.

In alternative embodiments of the sixth and seventh aspects of the invention, the additional therapeutic agent is an agent for the treatment or prevention of a non-alcoholic fatty liver disease (such as NASH), which agents will be readily identified by those skilled in the art and include, in particular, such therapeutic agents that are commercially available (e.g. agents that the subject of a marketing authorization in one or more territory, such as a European or US marketing authorization).

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of hyperglycaemia or a disorder characterized by hyperglycaemia (e.g. type 2 diabetes), and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds as defined in the first aspect of the invention (i.e. compounds of the invention) may be prepared in accordance with techniques that are well known to those skilled in the art, such as those described in the examples provided hereinafter.

For example, there is provided a process for the preparation of a compound of formula I, or a pharmaceutically acceptable salt thereof, as defined in the first aspect of the invention (which may be utilised in the preparation of, for example, a compound as defined in the second aspect of the invention), which process comprises:

(i) reaction of a compound of formula II

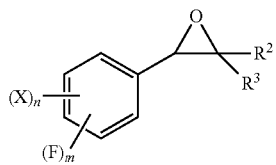

(II)

wherein $X^1$, $X^2$, $X^3$, $X^4$, $R^2$ and $R^3$ are as defined hereinabove, with a compound of formula $$H_2N-R^1 \quad (III)$$

wherein $R^1$ is as defined hereinabove, optionally in the presence of a suitable solvent known to those skilled in the art;

(iia) reaction of a compound of formula IV

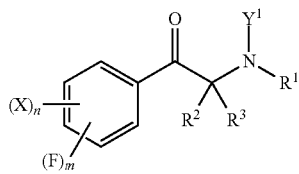

(IV)

wherein m, n, X, $R^1$, $R^2$ and $R^3$ are as defined hereinabove and $Y^1$ represents H or $PG^1$ wherein $PG^1$ is a suitable protecting group as known to those skilled in the art (e.g. —C(O)OtBu or —SO$_2$CH$_3$) with a suitable reduction agent as known to those skilled in the art (such as NaBH$_4$ or LiAlH$_4$, or a suitable chiral reducing agent), or by hydrogenation in the presence of a suitable catalyst (such as a chiral catalyst or additive);

(iib) for compounds of formula IB (and, similarly, compounds of formula IC) reaction of a compound of formula IV as defined herein above but wherein $Y^1$ represents $PG^1$ wherein $PG^1$ is a suitable protecting group as known to those skilled in the art (e.g. —C(O)OtBu) in the presence of a suitable catalyst (such as a complex between (1S, 2S)-(+)-N-(4-toluenesulphonyl)-1,2-diphenylethylene diamine and [Ru(cymene)Cl$_2$]$_2$)) in the presence of hydrogen or a suitable hydrogen donor (such as formic acid) and optionally in the presence of a base (e.g. Et$_3$N) and in the presence of a suitable solvent (such as CH$_2$Cl$_2$);

(iii) for compounds wherein at least one X is present and represents —OH, deprotection of a compound of formula V

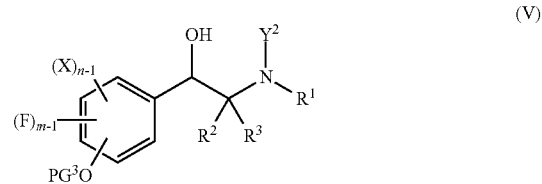

(V)

wherein m, n, $R^1$, $R^2$ and $R^3$ are as defined hereinabove, $Y^2$ represents H or $PG^2$, wherein $PG^2$ represents a suitable protecting group as known to those skilled in the art, and $PG^3$ represents a suitable protecting group as known to those skilled in the art (e.g. benzyl or alkyl, such as methyl) under conditions known to those skilled in the art (for example: in the case of benzyl, in the presence of hydrogen and a suitable catalyst or a suitable acid; in the case of alkyl, such as methyl, in the presence of BBr$_3$, HBr or alkyl sulfides);

(iv) for compounds wherein at least one X is present and represents NH$_2$ or NHC(O)CH$_3$, deprotection of a compound of formula VI

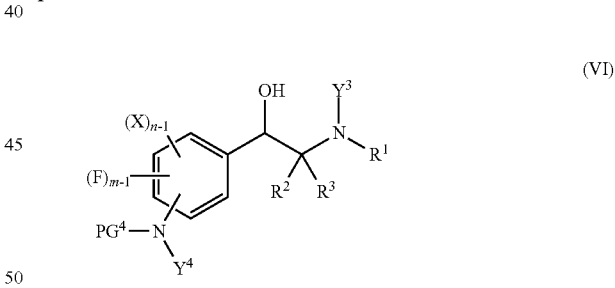

(VI)

wherein m, n, X, $R^1$, $R^2$ and $R^3$ are as defined hereinabove, $Y^3$ represents H or $PG^5$, wherein $PG^5$ represents a suitable protecting group as known to those skilled in the art, $Y^4$ represents H, C(O)CH$_3$ or $PG^6$, wherein $PG^6$ represents a suitable protecting group as known to those skilled in the art, and $PG^4$ represents a suitable protecting group as known to those skilled in the art (e.g. carbamate protecting groups (such as tert-butyloxycarbonyl (Boc), fluorenylmethyloxycarbonyl (Fmoc) and carboxybenzyl (Cbz) and amide protecting groups (such as acetyl and benzoyl)) under conditions known to those skilled in the art (for example in the case of Boc, in the presence of a suitable acid (e.g. trifluoroacetic acid or HCl). $PG^4$, $PG^5$ (if present) and $PG^6$ (if present) may each represent the same protecting group, and therefore may be deprotected under a single set of conditions;

(v) for compounds wherein at least one X is present and represents NH₂, reduction of a compound of formula VII

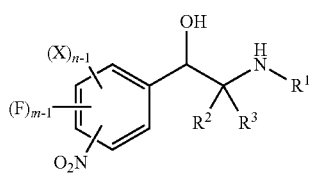

(VII)

wherein m, n, X, R¹, R² and R³ are as defined hereinabove, under conditions known to those skilled in the art (for example, by hydrogenation, such as hydrogenation using hydrogen gas and a suitable catalyst as known to those skilled in the art, (e.g. Pd—C, PtO₂, Raney-Nickel), Fe or Zn in acidic media (e.g. AcOH), borohydrides together with a suitable catalyst (e.g. NaBH₄ and Raney-Nickel), or agents such as SnC₂, TiCl₃, SmI₂, and the like. Those skilled in the art will understand that certain functional groups, such as the essential —OH and/or the —NHR¹ groups) may need to be protected (and deprotected) one or more times during the reaction, which protections (and deprotections) may be performed using techniques known to those skilled in the art.

Compounds of formulae II, III, IV, V VI and VII are either commercially available, are known in the literature, or may be obtained either by analogy with the processes described herein, or by conventional synthetic procedures, in accordance with standard techniques, from available starting materials (e.g. appropriately substituted benzaldehydes, styrenes or phenacyl bromides (or phenacylchloride, and the like) using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Science of Synthesis*", Volumes 9-17 (Hetarenes and Related Ring Systems), Georg Thieme Verlag, 2006.

The substituents X, R¹, R² and R³, as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Such compounds may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I or IA).

The skilled person will understand that compounds of formula I having specific stereochemistry (such as compounds of formula IB and IC) may be provided by reacting suitable starting materials having the required stereochemistry in processes as described herein.

For example, compounds of formula IB and IC may be provided by reacting compounds having the required stereochemistry in processes as described in step (i) or step (iii) in the processes described herein above.

Further, the skilled person will understand that suitable starting materials having the required stereochemistry (such as suitable compounds of formula II and V wherein the carbon substituted with the essential oxygen is the (R) configuration, as required for the preparation of compounds of formula IB and IC) may be prepared by analogy with the process described in step (iib) herein above.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds as described herein (in particular, compounds as defined in the first and, therefore, second and third aspects of the invention) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, such compounds may have the advantage that they are more efficacious and/or exhibit advantageous properties in vivo.

Without wishing to be bound by theory, compounds as described herein are thought to be potent agonists of the β₂-adrenergic receptor, which allows for increased glucose uptake in skeletal muscle cells.

In addition, compounds as described herein are thought to be agonists of the β₂-adrenergic receptor without (or with only a minimal effect in) inducing cAMP production. It is thought that this allows for the increased glucose uptake in skeletal muscle cells with lower levels of side effects than would result from other treatments. Further, combining compounds as described herein with therapeutic agents that are able to decrease blood glucose levels is thought to provide an effective combination therapy.

Furthermore, compounds of the invention may be particularly resistant to metabolism (e.g. first-past metabolism), i.e. the process by which pharmaceutical agents are biotransformed to aid excretion.

EXAMPLES

The present invention is illustrated by way of the following examples.

Chemicals and reagents were obtained from commercial suppliers and were used as received unless otherwise stated.

All reactions involving moisture sensitive reagents were performed in oven or flame dried glassware under a positive pressure of nitrogen or argon.

Abbreviations

Abbreviations as used herein will be known to those skilled in the art. In particular, the following abbreviations may be used herein.

AcOH acetic acid
aq aqueous
atm atmosphere
Boc$_2$O di-tert-butyldicarbonate
DIPEA N,N-diisopropylethylamine
DMAP 4-dimethylaminopyridine
DMF dimethylformamide
DMSO dimethylsulfoxide
eq equivalent
EtOAc ethyl acetate
HPLC high-performance liquid chromatography
iPrOH isopropanol
MeCN acetonitrile
MeOH methanol
Pd—C palladium on carbon
rt room temperature
sat saturated
TFA trifluoroacetic acid
THF tetrahydrofuran Example Compounds In the event that there is a discrepancy between nomenclature and the structure of compounds as depicted graphically, it is the latter that presides (unless contradicted by any experimental details that may be given and/or unless it is clear from the context).

Example 1:
2-(Butylamino)-1-(3,5-difluorophenyl)ethan-1-ol

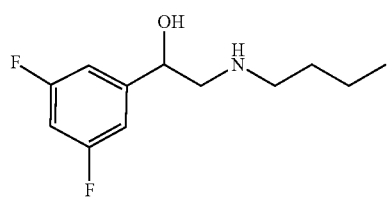 [SMILES: CCCCNCC(O)c1cc(F)cc(F)c1]

(a) 2-(3,5-Difluorophenyl)oxirane

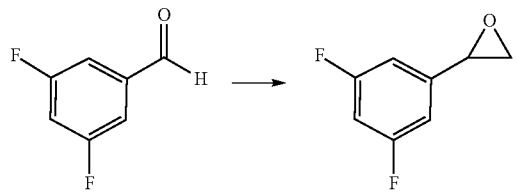 [SMILES: O=Cc1cc(F)cc(F)c1 ; Fc1cc(F)cc(C2CO2)c1]

A solution of trimethylsulfonium iodide (413 mg, 2.02 mmol) in DMSO (6 mL) was added dropwise to an ice-cooled suspension of NaH (2.1 mmol, prepared from 84 mg 60% NaH in mineral oil by washing with Et$_2$O) in THF (6 mL). The ice-cooled mixture was stirred for 30 min and a solution of 3,5-difluorobenzaldehyde (250 mg, 1.76 mmol) in THF (2.45 mL) was slowly added. The mixture was stirred for 20 min, the cooling bath removed and stirring was continued at rt for 2 h. The mixture was poured onto ice and extracted with Et$_2$O. The combined extracts were washed with water, brine, dried (Na$_2$SO$_4$) and concentrated to give the sub-title compound (257 mg, 1.65 mmol, 94%) which was used in the next step without any further purification.

(b) 2-(Butylamino)-1-(3,5-difluorophenyl)ethan-1-ol

A mixture of 2-(3,5-difluorophenyl)oxirane (100 mg, 0.64 mmol), n-butylamine (158 µL, 1.60 mmol) and MeOH (1 mL) was stirred at reflux for 6 h. The mixture was concentrated and the residue purified by chromatography to give the title compound (98 mg, 0.43 mmol, 67%).

$^1$H NMR (300 MHz, CDCl$_3$): δ 6.97-6.84 (m, 2H), 6.69 (tt, J=8.8, 2.4 Hz, 1H), 4.64 (dd, J=8.7, 3.6 Hz, 1H), 2.92 (dd, J=12.0, 3.6 Hz, 1H), 2.72-2.55 (m, 3H), 1.52-1.27 (m, 4H), 0.92 (t, J=7.2 Hz, 3H).

Example 2:
2-(Butylamino)-1-(3,4-difluorophenyl)ethan-1-ol

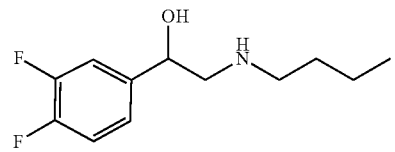 [SMILES: CCCCNCC(O)c1ccc(F)c(F)c1]

(a) 2-(Benzyl(butyl)amino)-1-(3,4-difluorophenyl)ethan-1-ol

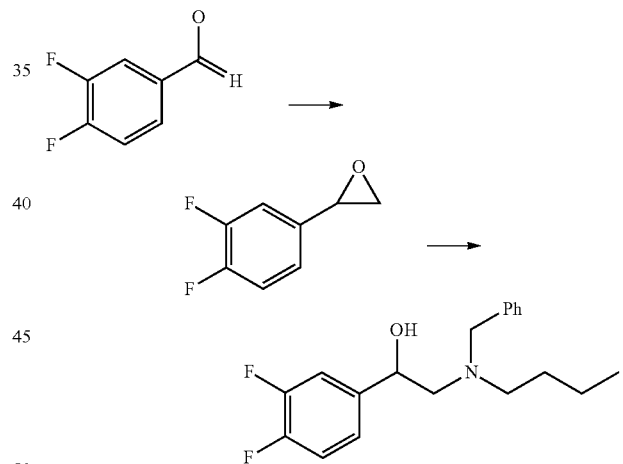

The sub-title compound was prepared in accordance with the procedure in Example 1, Steps (a) and (b) from 3,4-difluorobenzaldehyde and N-benzylbutylamine.

(b) 2-(Butylamino)-1-(3,4-difluorophenyl)ethan-1-ol

A mixture of 2-(benzyl(butyl)amino)-1-(3,4-difluorophenyl)ethan-1-ol (70 mg, 0.22 mmol), 10% Pd—C(23.3 mg, 0.022 mmol) and AcOH (2 mL) was hydrogenated at 6.5 atm at rt for 2 h, filtered through Celite and concentrated. NaHCO$_3$ (aq, sat) was added to the residue, which was extracted with Et$_2$O. The combined extracts were washed with water, brine, dried (Na$_2$SO$_4$), concentrated and purified by chromatography to give the title compound (30 mg, 0.13 mmol, 60%).

$^1$H NMR (400 MHz, CDCl$_3$): δ 7.24-7.19 (m, 1H), 7.15-7.04 (m, 2H), 4.67 (dd, J=9.2, 3.5 Hz, 1H), 2.89 (dd,

J=12.2, 3.6 Hz, 1H), 2.86-2.69 (br s, 2H overlapping), 2.74-2.58 (m, 3H), 1.54-1.42 (m, 2H), 1.35 (h, J=7.2 Hz, 2H), 0.92 (t, J=7.3 Hz, 3H)

Example 3: (R)-2-(Butylamino)-1-(4-fluorophenyl)ethan-1-ol

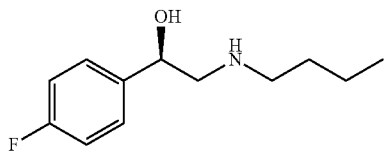

(a) tert-Butyl butyl(2-(4-fluorophenyl)-2-oxoethyl)carbamate

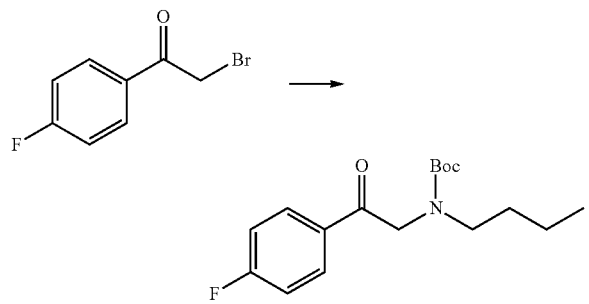

A solution of 4-fluorophenacyl bromide (300 mg, 1.38 mmol) in CH$_2$Cl$_2$ (4 mL) was added over 10 min to a mixture of n-butylamine (205 μL, 2.07 mmol), DIPEA (239 μL, 1.38 mmol) and CH$_2$Cl$_2$ (1 mL) at 0° C. The mixture was stirred at rt for 2 h, Boc$_2$O (3.4 mL, 15 mmol) was added and the mixture was stirred at rt for 2 h. The mixture was washed with H$_2$O and brine, dried over Na$_2$SO$_4$ and filtered. The filtrate was concentrated and purified by chromatography to give the sub-title compound (270 mg, 0.87 mmol, 63%).

(b) tert-Butyl (R)-butyl(2-(4-fluorophenyl)-2-hydroxyethyl)carbamate

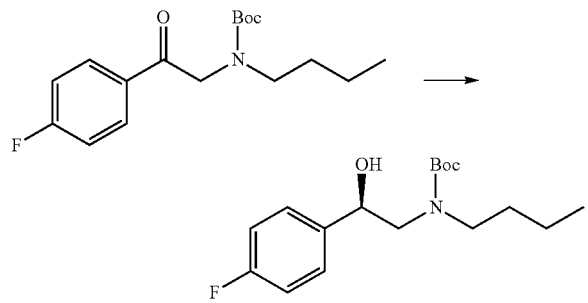

(S,S)—N-(p-Toluenesulfonyl)-1,2-diphenylethanediamine(chloro)(p-cymene)ruthenium(II) (16.4 mg, 0.026 mmol) (prepared as described in as described in Kawamato, A. M. and Wills, M., J. Chem. Soc. Perkin 1, 1916 (2001)) was added to a mixture of tert-butyl butyl(2-(4-fluorophenyl)-2-oxoethyl)carbamate (200 mg, 0.65 mmol) in formic acid/Et$_3$N (5:2, 2 mL). The mixture was stirred at rt for 64 h and H$_2$O (15 mL) and CH$_2$Cl$_2$ (15 mL) was added. The layers were separated and the aq layer extracted with CH$_2$Cl$_2$. The combined organic phases were washed with H$_2$O, brine, dried over Na$_2$SO$_4$ and concentrated. The residue was purified by chromatography to give the sub-title compound (164 mg, 0.53 mmol, 82%).

(c) (R)-2-(Butylamino)-1-(4-fluorophenyl)ethan-1-ol

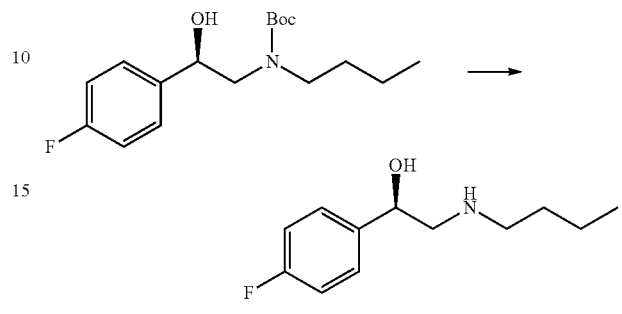

A solution of NaOH (421 mg, 10.5 mmol) in water (1.5 mL) was added to a solution of tert-butyl (R)-butyl(2-(4-fluorophenyl)-2-hydroxyethyl)carbamate (164 mg, 0.53 mmol) in EtOH (1.5 mL). The mixture was heated at 120° C. in a sealed vial for 16 h. After cooling, the pH was adjusted to 6 with HCl (1 M, aq) and the mixture extracted with EtOAc. The combined extracts were dried (Na$_2$SO$_4$), concentrated and purified by chromatography to give the title compound (64 mg, 0.30 mmol, 58%).

$^1$H NMR (400 MHz, CDCl$_3$): δ 7.41-7.36 (m, 2H), 7.04-6.98 (m, 2H), 5.40 (dd, J=10.5, 2.6 Hz, 1H), 3.19 (dd, J=12.5, 2.6 Hz, 1H), 3.09 (dd, J=12.5, 10.5 Hz, 1H), 3.06-3.01 (m, 2H), 1.90-1.82 (m, 2H), 1.45-1.36 (m, 2H), 0.91 (t, J=7.4 Hz, 3H).

Example 4: (R)-2-(Butylamino)-1-(3-fluorophenyl)ethan-1-ol

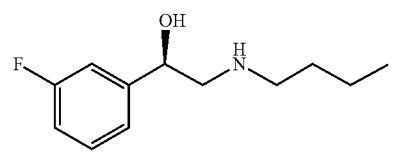

The title compound was prepared in accordance with the procedure in Example 3 from 3-fluorophenacyl bromide.

$^1$H NMR (400 MHz, CDCl$_3$): δ 7.33-7.26 (m, 1H), 7.14-7.11 (m, 2H), 6.98-6.93 (m, 1H), 7.00-6.82 (br s, 3H), 4.93 (dd, J=9.9, 3.1 Hz, 1H), 2.99 (dd, J=12.3, 3.1 Hz, 1H), 2.88-2.72 (m, 3H), 1.98 (s, 3H), 1.63-1.56 (m, 2H), 1.40-1.31 (m, 2H), 0.91 (t, J=7.3 Hz, 3H).

Example 5: (R)-2-(tert-Butylamino)-1-(3-fluorophenyl)ethan-1-ol

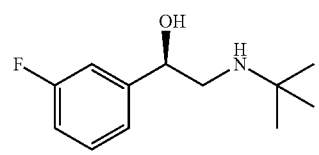

(a) (R)-2-bromo-1-(3-fluorophenyl)ethan-1-ol

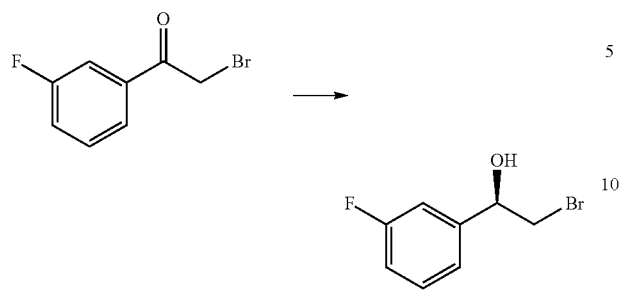

Borane (1 M in THF, 0.68 mL, 0.68 mmol) was added dropwise to a mixture of (R)-2-methyl-CBS-oxazaborolidine (1 M in toluene, 0.85 mL, 0.85 mmol) and THF (0.8 mL) at rt. The mixture was stirred 15 min at rt and a solution of 3-fluorophenacyl bromide (185 mg, 0.85 mmol) in THF (1.9 mL) was added dropwise (0.09 mL/min). After 6 h at rt, MeOH (10 mL) was added. The mixture was stirred for 30 min and concentrated. Purification by chromatography gave the sub-title compound (150 mg, 0.68 mmol, 80%).

(b) (R)-2-(3-fluorophenyl)oxirane

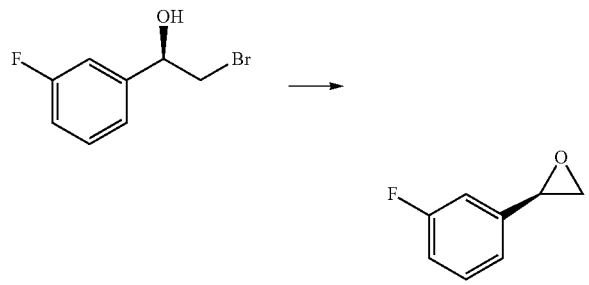

$K_2CO_3$ (137 mg, 0.99 mol) was added to a mixture of (R)-2-bromo-1-(3-fluorophenyl)ethan-1-ol (145 mg, 0.66 mmol) in MeOH (6.8 mL) at rt. The mixture was stirred for 30 min, filtered and concentrated. The residue was extracted with $CH_2Cl_2$. The combined extracts were concentrated to give the sub-title compound (70 mg, 0.51 mmol, 77%), which was used in the next step without further purification.

(c) (R)-2-(tert-butylamino)-1-(3-fluorophenyl)ethan-1-ol

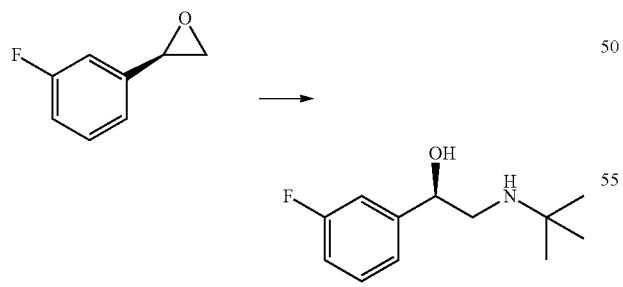

A mixture of (R)-2-(3-fluorophenyl)oxirane (30 mg, 0.22 mmol), tert-butylamine (66 mg, 0.90 mmol) and MeOH (0.2 mL) was stirred at reflux for 16 h, cooled and concentrated and dissolved in a $Et_2O$. $Et_2O$/pentane (1:3) was added and the solution was kept at −20° C. overnight. The solid formed was collected to give the title compound (25 mg, 0.12 mmol, 54%).

$^1$H NMR (400 MHz, $CDCl_3$): δ 7.33-7.26 (m, 1H), 7.14-7.09 (m, 2H), 6.98-6.93 (m, 1H), 4.57 (dd, J=8.4, 3.6 Hz, 1H), 2.92 (dd, J=12.0, 4.0 Hz, 1H), 2.55 (dd, J=12.0, 8.4 Hz, 1H), 1.10 (s, 9H).

Example 6: 1-(4-Amino-3,5-difluorophenyl)-2-(butylamino)ethan-1-ol

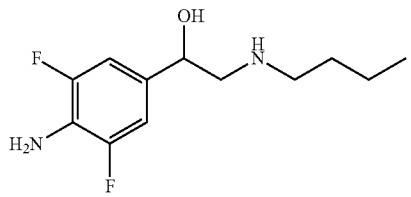 [SMILES: CCCCNCC(O)c1cc(F)c(N)c(F)c1]

(a) 1-(4-Amino-3,5-difluorophenyl)ethan-1-one

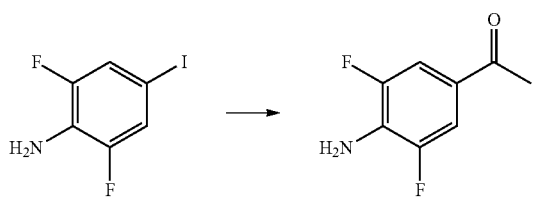

$PdCl_2(MeCN)_2$ (102 mg, 0.39 mmol) was added to a mixture of 3,6-difluoro-4-iodoaniline (2.00 g, 7.84 mmol), ZnO (830 mg, 10.2 mol), tetrabutylammonium bromide (3.79 g, 11.8 mmol), $Et_3N$ (0.37 mL, 2.67 mmol) and DMSO (20 mL) at rt. The mixture was stirred at 100° C. in ambient atmosphere for 16 h. Another portion of $Et_3N$ (0.37 mL, 2.67 mmol) was added and the heating was continued for 3 h. The mixture was allowed to cool, diluted with $Et_2O$ and washed with $H_2O$. The phases were separated and the aq layer was extracted with $Et_2O$. The combined organic phases were washed with brine, dried over $Na_2SO_4$ and concentrated. The residue was purified by chromatography to give the sub-title compound (270 mg, 1.58 mmol, 20%)

(b) 1-(4-Amino-3,5-difluorophenyl)-2-bromoethan-1-one

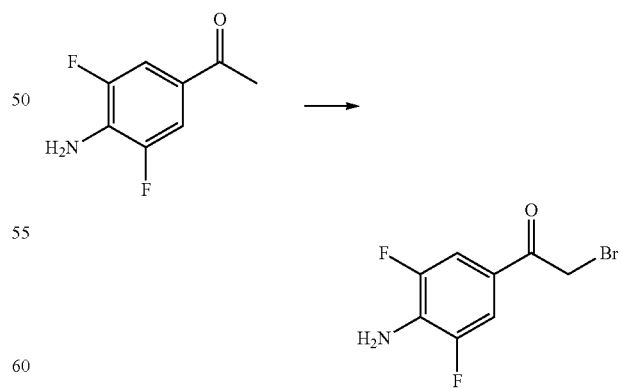

A mixture of bromine (0.16 mL, 3.15 mmol) and $CHCl_3$ (10 mL) was added over 30 min to a mixture of 1-(4-amino-3,5-difluorophenyl)ethan-1-one (270 mg, 1.58 mmol) and $CHCl_3$ (15 mL) at reflux. After 15 min at reflux, the mixture was allowed to cool and concentrated. The residue was dissolved in THF (6 mL) and cooled in an ice-bath. A solution of diethylphosphite (0.22 mL, 1.74 mmol) and Et₃N (0.24 mL, 1.74 mmol) in THF (9 mL) was slowly added. The mixture was slowly allowed to reach rt, stirred at rt for 17 h and concentrated. Ice/water was added to the residue and the mixture was extracted with EtOAc. The combined extracts were washed with brine, dried over Na₂SO₄ and concentrated. The residue was purified by chromatography to give the sub-title compound (250 mg, 1.00 mmol, 63%).

(c) 1-(4-Amino-3,5-difluorophenyl)-2-(butylamino) ethan-1-one hydrochloride

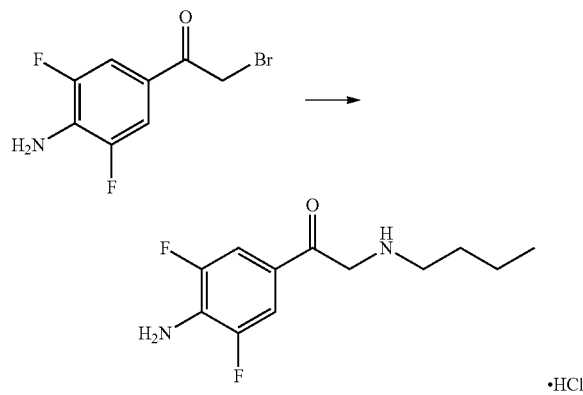

DIPEA (83 μL, 0.48 mmol) followed by n-butylamine (47 μL, 0.48 mmol) were added to a solution of 1-(4-amino-3,5-difluorophenyl)-2-bromoethan-1-one (100 mg, 0.40 mmol) in CHCl₃ (1 mL) at rt. The mixture was heated at 75° C. for 1 h and allowed to cool to 40-50° C. when HCl (1 M in Et₂O, 560 μL, 0.56 mmol) was added. The mixture was cooled to rt and the solid collected to give the sub-title compound (44 mg, 0.16 mmol, 40%), which was used in the next step without further purification.

(d) 1-(4-Amino-3,5-difluorophenyl)-2-(butylamino) ethan-1-ol

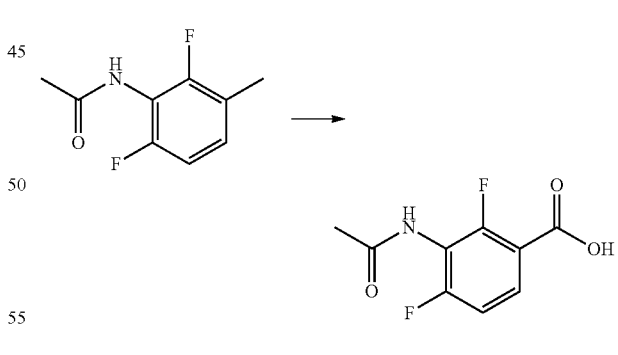

NaOH (1 M, ~0.15 mL) was added to a mixture of 1-(4-amino-3,5-difluorophenyl)-2-(butylamino)ethan-1-one hydrochloride (40 mg, 0.14 mmol), MeOH (0.2 mL) and H₂O (0.3 mL) to adjust the pH to 9. A solution of NaBH₄ (10.9 mg, 0.29 mmol) in H₂O was added dropwise and the mixture was stirred at rt for 2 h. The mixture was concentrated to remove the MeOH. Water was added and the mixture was extracted with CH₂Cl₂. The combined extracts were washed with brine, dried over Na₂SO₄ and concentrated. The residue was dissolved in Et₂O (1 mL). Pentane (5 mL) was added and the solid was collected to give the sub-title compound (20 mg, 0.082 mmol, 57%)

¹H NMR (400 MHz, CDCl₃): δ 6.89-6.80 (m, 2H), 4.54 (dd, J=8.8, 3.4 Hz, 1H), 3.75-3.60 (br s, 2H), 2.84 (dd, J=12.1, 3.4 Hz, 1H), 2.70-2.57 (m, 3H), 2.73-2.03 (br s, 2H, overlapping), 1.51-1.41 (m, 2H), 1.40-1.29 (m, 2H), 0.92 (t, J=7.4 Hz, 3H).

Example 7: 1-(3-Amino-2,4-difluorophenyl)-2-(butylamino)ethan-1-ol

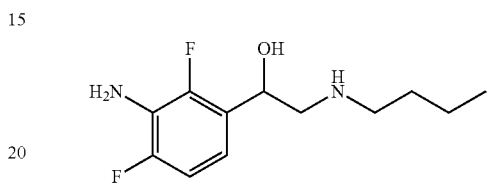

(a) N-(2,6-Difluoro-3-methylphenyl)acetamide

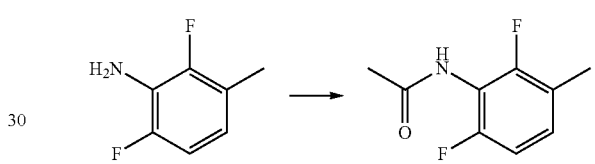

A mixture of 2,6-difluoro-3-methylaniline (4 g, 27.9 mmol) and acetic anhydride (5.3 mL) was heated at 60° C. for 2 h. Water was added and the mixture was extracted with CH₂Cl₂. The combined extracts were washed with brine, dried over Na₂SO₄ and concentrated. Purification by chromatography gave the sub-title compound (5.1 g, 27.5 mmol, 99%).

(b) 3-Acetamido-2,4-difluorobenzoic acid

KMnO₄ (10.7 g, 67.7 mmol) was added cautiously to a mixture of N-(2,6-difluoro-3-methylphenyl)acetamide (2.5 g, 13.5 mmol), pyridine (20 mL) and H₂O (70 mL) at 70° C. The mixture was heated at reflux for 10 h, filtered while hot through a pad of Celite and the pad was washed with hot H₂O. The filtrates were cooled to rt, concentrated and carefully acidified with HCl (aq, 6 M). The mixture was cooled in an ice-bath and filtered. The solids were washed with cold H₂O, dried and purified by chromatography to give the sub-title compound (2.1 g, 9.76 mmol, 72%).

(c) N-(3-(2-Bromoacetyl)-2,6-difluorophenyl)acetamide

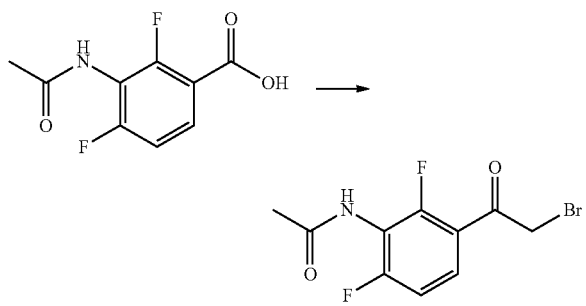

A mixture of 3-acetamido-2,4-difluorobenzoic acid (1.1 g, 5.11 mmol), SOCl$_2$ (8 mL) and CH$_2$Cl$_2$ (20 mL) was stirred at rt for 2 h, concentrated and dried in vacuo. The residue was dissolved in CH$_2$Cl$_2$ (60 mL) and trimethylsilyl diazomethane (5.1 mL, 10.2 mmol) was added dropwise at 0° C. The mixture was allowed to come to rt over 4 h and cooled to 0° C. HBr (33% in AcOH, 2.8 mL) was added dropwise. The mixture was allowed to come to rt over 2.5 h, diluted with CH$_2$Cl$_2$ and washed NaHCO$_3$ (aq, sat) and NH$_4$Cl (aq, sat) and dried over MgSO$_4$ and concentrated to give a quantitative yield of the sub-title compound, which was used in the next step without further purification.

(d) 1-(3-Amino-2,4-difluorophenyl)-2-bromoethan-1-one

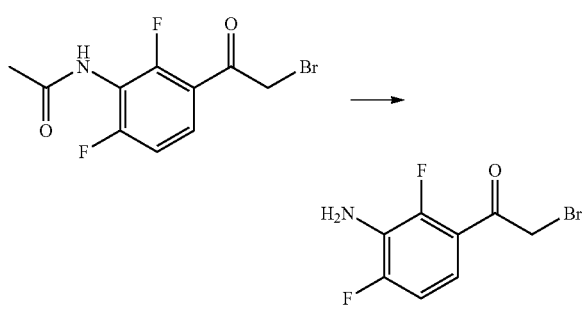

HBr (aq, 48%, 0.05 mL) was added to N-(3-(2-bromoacetyl)-2,6-difluorophenyl)acetamide (70 mg, 0.24 mmol) at rt. The mixture was heated to 100° C. and stirred at that temperature for 40 min, cooled and poured into H$_2$O. The mixture was extracted with EtOAc and the combined extracts were washed with H$_2$O, NaHCO$_3$ (aq, sat), brine and dried over MgSO$_4$. Concentration gave the sub-title compound (50 mg, 0.20 mmol, 83%).

(e) 2,6-Difluoro-3-(oxiran-2-yl)aniline

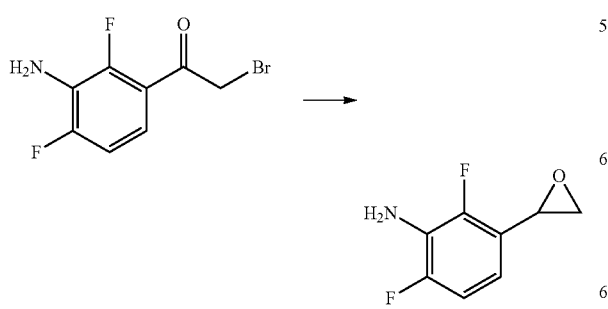

NaBH$_4$ (3.78 mg, 0.10 mmol) was added to a mixture of 1-(3-mino-2,4-difluorophenyl)-2-bromoethan-1-one (50 mg, 0.20 mmol) at 0° C. The cooling bath was removed and the mixture was stirred at rt for 1 h. MeOH (1 mL) and K$_2$CO$_3$ (41.5 mg, 0.30 mmol) were added and the mixture was stirred at rt for 3 h and concentrated. Water was added to the residue and the mixture was extracted with CH$_2$Cl$_2$ and the combined extracts were washed with H$_2$O, brine, dried over MgSO$_4$ and filtered through neutral alumina. Concentration gave the sub-title compound (20 mg, 0.12 mmol, 58%).

(f) 1-(3-Amino-2,4-difluorophenyl)-2-(butylamino)ethan-1-ol

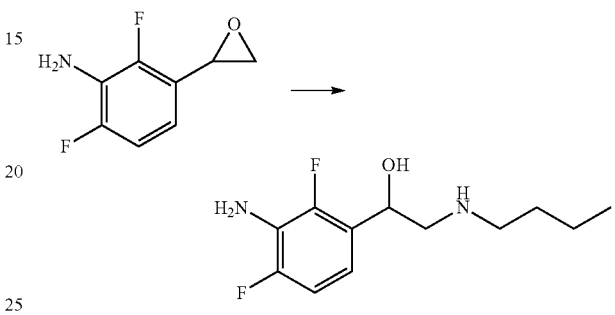

A mixture of 2,6-difluoro-3-(oxiran-2-yl)aniline (30 mg, 0.18 mmol), n-butylamine (12.8 mg, 0.18 mmol) and EtOH (0.9 mL) was stirred at 50° C. for 18 h. The mixture was concentrated and the residue purified by chromatography to give the title compound (22 mg, 0.09 mmol, 51%).

$^1$H NMR (400 MHz, CDCl$_3$): δ 6.90-6.72 (m, 2H), 4.97 (dd, J=8.8, 3.6 Hz, 1H), 3.70 (s, 2H), 2.94 (dd, J=13.0, 3.6 Hz, 1H), 2.72-2.58 (m, 3H), 1.52-1.30 (m, 4H), 0.92 (t, J=7.2 Hz, 3H).

Example 8: N-(3-(2-(Butylamino)-1-hydroxyethyl)-2,6-difluorophenyl)acetamide

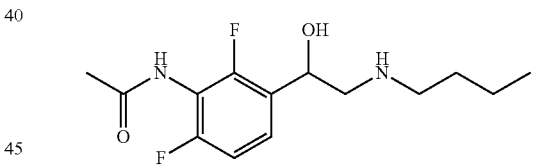

The title compound was prepared from N-(3-(2-bromoacetyl)-2,6-difluorophenyl)-acetamide (see Example 7, Step (c)) in accordance with the procedures in Example 7, Steps (e) and (f).

$^1$H NMR (400 MHz, THF-d$_8$): δ 8.69 (br s, 1H), 7.41 (q, J=8.2 Hz, 1H), 6.92 (t, J=8.8 Hz, 1H), 4.93 (dd, J=8.6, 3.2 Hz, 1H), 2.76 (ddd, J=8.4, 4.8, 3.6 Hz 1H), 2.66-2.56 (m, 3H), 2.04 (s, 3H), 1.48-1.29 (m, 4H), 0.90 (t, J=7.2 Hz, 3H).

Example 9: 1-(4-Amino-3,5-difluorophenyl)-2-(butylamino)ethan-1-ol

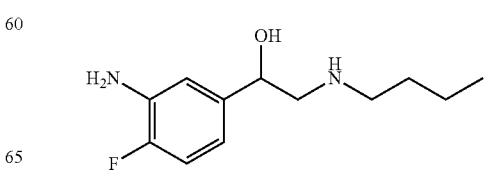

(a) 3-Amino-2-fluoroacetophenone

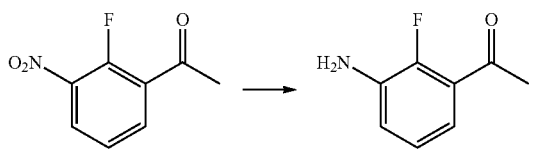

Fe powder (595 mg, 10.6 mmol) followed by NH₄Cl (570 mg, 10.6 mmol) in H₂O (1.2 mL) were added to a solution of 2-fluoro-3-nitroacetophenone at 55° C. The mixture was heated at reflux for 2.5 h, cooled to rt and filtered through Celite. NaHCO₃ (aq, sat) was added to the filtrate, which then was extracted with EtOAc. The combined extracts were washed with brine, dried over MgSO₄ and concentrated. The residue was extracted with hexane and the extract concentrated. The residue was extracted with hexane/Et₂O (10:1) and the extract concentrated to give the sub-title compound (350 mg, 2.28 mmol, 84%).

(b) N-(3-Acetyl-2-fluorophenyl)acetamide

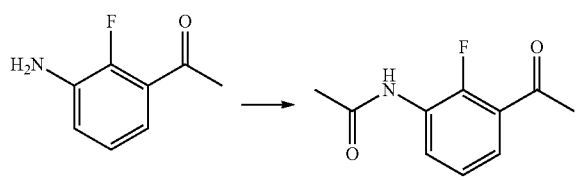

The sub-title compound was prepared in accordance with the procedure in Example 7, Step (a) from 3-amino-2-fluoroacetophenone.

(c) N-(3-(2-Bromoacetyl)-2,6-difluorophenyl)acetamide

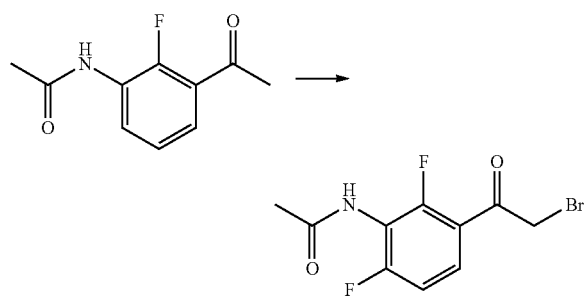

CuBr (652 mg, 2.92 mmol) was added to a solution of N-(3-acetyl-2-fluorophenyl)-acetamide (380 mg, 1.95 mmol) in EtOAc (4.8 mL) at rt. The mixture was heated at reflux for 20 h, allowed to cool and extracted with EtOAc. The combined extracts were washed with brine, dried over MgSO₄, filtered through neutral alumina and concentrated. The residue was purified by chromatography to give the sub-title compound (135 mg, 0.49 mmol, 25%).

(d) 1-(4-Amino-3,5-difluorophenyl)-2-(butylamino)ethan-1-ol

The title compound was prepared from N-(3-(2-bromoacetyl)-2,6-difluorophenyl)-acetamide in accordance with the procedures in Example 7, Steps (d), (e) and (f).

¹H NMR (400 MHz, CDCl₃): δ 6.93 (dd, J=11.0, 8.2 Hz, 1H), 6.82 (dd, J=8.6, 2.2 Hz, 1H), 6.67-6.64 (m, 1H), 4.58 (dd, J=9.0, 3.8 Hz, 1H), 3.71 (s, 2H), 2.86 (dd, J=12.0, 3.6 Hz, 1H), 2.70-2.60 (m, 3H), 1.51-1.30 (m, 4H), 0.92 (t, J=7.4 Hz, 3H).

Examples 10 and 11: (R)-1-(4-Fluorophenyl)-2-(((R)-pentan-2-yl)amino)ethan-1-ol and (R)-1-(4-Fluorophenyl)-2-(((S)-pentan-2-yl)amino)ethan-1-ol

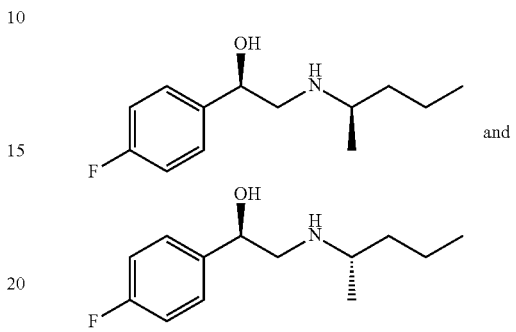

(a) tert-Butyl (2-(4-fluorophenyl)-2-oxoethyl)(pentan-2-yl)carbamate

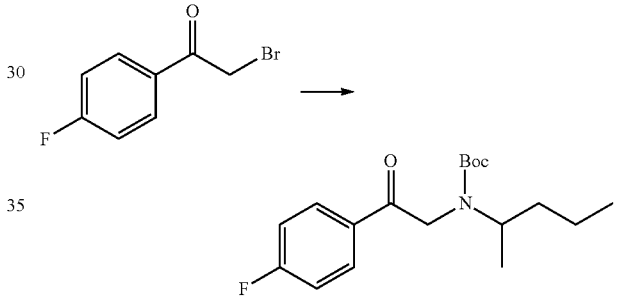

A solution of 4-fluorophenacyl bromide (500 mg, 2.31 mmol) in CH₂Cl₂ (6.6 mL) was added over 10 min to a solution of 2-aminopentane (301 mg, 3.46 mmol) and DIPEA (298 mg, 2.31 mmol) in CH₂Cl₂ (1.6 mL) at 0° C. The cooling bath was removed and the mixture was stirred at rt for 2 h. A solution of Boc₂O (1.26 g, 5.76 mmol) in CH₂Cl₂ (6 mL) was added and the mixture was stirred at rt for 2 h, washed with H₂O, brine and dried over Na₂SO₄. Concentration and purification by chromatography gave the sub-title compound (520 mg, 1.61 mmol, 70%).

(b) (R)-1-(4-Fluorophenyl)-2-(((R)-pentan-2-yl)amino)ethan-1-ol and (R)-1-(4-Fluorophenyl)-2-(((S)-pentan-2-yl)amino)ethan-1-ol The title compounds were obtained using the procedure in Example 3, Step (b) followed by chromatographic separation and hydrolysis of the individual Boc-protected intermediates in accordance with the procedure in Example 3, step (c).

¹H NMR (400 MHz, CDCl₃): δ 7.34 (dd, J=8.4, 5.6 Hz, 2H), 7.03 (t, J=8.4 Hz, 2H), 4.61 (dd, J=9.4, 3.4 Hz, 1H), 2.91 (dd, J=12.0, 3.6 Hz, 1H), 2.69-2.59 (m, 2H), 1.47-1.28 (m, 4H), 1.06 (d, J=6.0 Hz, 3H), 0.91 (t, J=6.8 Hz, 3H).
and
7.42 (dd, J=8.4, 5.6 Hz, 2H), 7.03 (t, J=8.8 Hz, 2H), 5.40 (dd, J=10.4, 2.4 Hz, 1H), 3.28-3.21 (m, 2H), 2.99 (t, J=11.2 Hz, 1H), 1.94-1.85 (m, 1H), 1.72-1.63 (m, 1H), 1.51-1.34 (m, 5H), 0.91 (t, J=7.4 Hz, 3H).

Examples 12 and 13: (R)-1-(3-fluorophenyl)-2-(((R)-pentan-2-yl)amino)ethan-1-ol and (R)-1-(3-fluorophenyl)-2-(((S)-pentan-2-yl)amino)ethan-1-ol

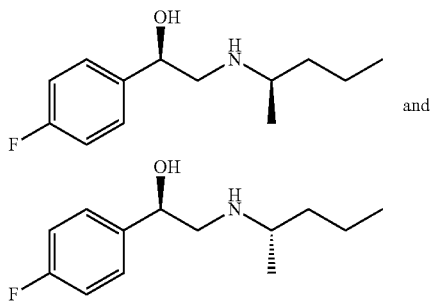
and

The title compounds were prepared in accordance with Examples 10 and 11 from 3-fluorophenacyl bromide.

$^1$H NMR (400 MHz, CDCl$_3$): δ 7.33-7.26 (m, 1H), 7.14-7.09 (m, 2H), 7.00-6.90 (m, 1H), 4.66 (dd, J=8.8, 3.6 Hz, 1H), 2.97-2.92 (m, 1H), 2.72-2.62 (m, 3H), 1.47-1.26 (m, 4H), 1.07 (dd, J=6.4, 1.2 Hz, 3H), 0.93-0.89 (m, 3H). and 7.33-7.27 (m, 1H), 7.21-7.18 (m, 2H), 7.00-6.96 (m, 1H), 5.40 (dd, J=10.4, 2.4 Hz, 1H), 3.31-3.20 (m, 2H), 2.98 (t, J=11.4, Hz, 1H), 1.93-1.85 (m, 1H), 1.72-1.62 (m, 1H), 1.50-1.33 (m, 5H), 0.91 (t, J=7.4 Hz, 3H).

Example 14: (R)-1-(3-Fluorophenyl)-2-((2-methylpentan-2-yl)amino) ethan-1-ol

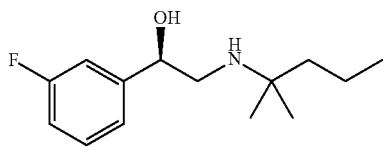 [SMILES: CCCC(C)(C)NC[C@H](O)c1cccc(F)c1]

A mixture of (R)-2-(3-fluorophenyl)oxirane (40 mg, 0.29 mmol), 2-methylpentan-2-amine hydrochloride (80 mg, 0.58 mmol), DIPEA (0.1 mL, 0.58 mmol) and MeOH (0.3 mL) was stirred at reflux for 16 h, cooled and concentrated. The residue was purified by chromatography and crystallization from Et$_2$O/hexane (1:4) to give the title compound (10 mg, 0.042 mmol, 14%).

$^1$H NMR (400 MHz, CDCl$_3$): δ 7.32-7.27 (m, 1H), 7.19-7.09 (m, 2H), 6.98-6.93 (m, 1H), 4.85 (dd, J=9.2, 3.2 Hz, 1H), 4.07 (br s, 1H), 2.99 (dd, J=11.8, 3.4 Hz, 1H), 2.66 (dd, J=12.2, 9.4 Hz, 1H), 1.48-1.27 (m, 4H), 1.18 (d, J=3.6 Hz, 6H), 0.91 (t, J=7.2 Hz, 3H).

Example 15: (R)-2-(tert-Butylamino)-1-(2,3-difluorophenyl)ethan-1-ol

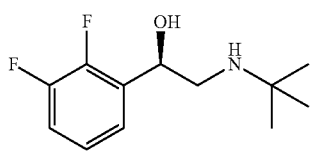 [SMILES: CC(C)(C)NC[C@H](O)c1cccc(F)c1F]

(a) 2-Bromo-1-(2,3-difluorophenyl)ethan-1-one

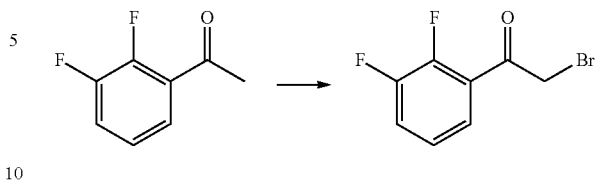

Trimethylphenylammonium tribromide (1.59 g, 4.22 mmol) was added in portions to a stirred solution of 2,3-difluoroacetophenone (0.60 g, 3.84 mmol) in CH$_2$Cl$_2$ (10 mL) at rt. The mixture was stirred at rt overnight, diluted with CH$_2$Cl$_2$ and poured into water. The layers were separated and the aq phase was extracted with CH$_2$Cl$_2$. The combined extracts were dried (Na$_2$SO$_4$), filtered and concentrated. The residue was purified by chromatography to give the sub-title compound (0.80 g, 3.40 mmol, 89%).

(b) 2-Chloro-1-(2,3-difluorophenyl)ethan-1-one

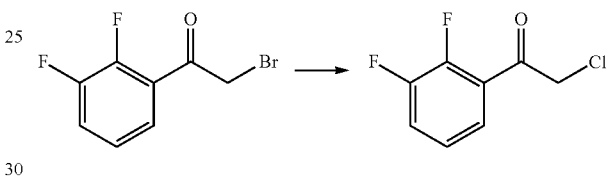

NaCl (aq., sat, 4 mL) was added to a solution of 2-bromo-1-(2,3-difluorophenyl)ethan-1-one (600 mg, 2.55 mmol) in THF (10 mL) at rt. The mixture was heated in a sealed tube at 70° C. for 16 h and allowed to cool. The mixture was diluted with EtOAc (100 mL) and brine and the layers separated. The aq phase was extracted with EtOAc and the combined organic phases dried (Na$_2$SO$_4$), filtered and concentrated. The residue was purified by chromatography to give the sub-title compound (350 mg, 1.84 mmol, 72%).

(c) (R)-2-Chloro-1-(2,3-difluorophenyl)ethan-1-ol

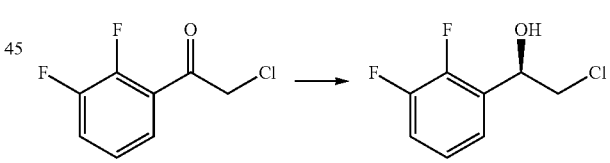

RhClCp*[(1S,2S)-p-TsNCH(C$_6$H$_5$)CH(C$_6$H$_5$(CeH) NH$_2$]/HCl.Et$_3$N (20.4 mg, 26 pmol), prepared from dichloro(pentamethylcyclopentadienyl)rhodium (III) dimer, (1S,2S)-(+)—N-(4-toluene-sulphonyl)-1,2-diphenylethylene diamine and Et$_3$N as described in WO 2008/054155, was added to a mixture of 2-chloro-1-(2,3-difluorophenyl)ethan-1-one (500 mg, 2.62 mmol) in THF (10 mL). Formic acid/Et$_3$N (5:2, 1 mL) was added and the mixture was stirred at rt for 80 min. The mixture was diluted with EtOAc, washed twice with H$_2$O, dried (Na$_2$SO$_4$), filtered and concentrated. The residue was purified by chromatography to give the sub-title compound (420 mg, 2.18 mmol, 83%, ee=88%).

(d) (R)-2-(2,3-Difluorophenyl)oxirane

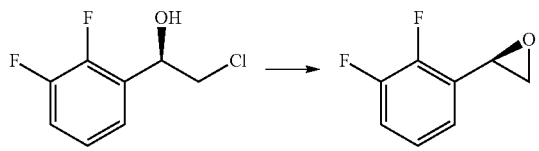 [SMILES: O[C@@H](CCl)c1cccc(F)c1F ; Fc1cccc([C@@H]2CO2)c1F]

NaOH (aq, 1 M, 5.9 mL, 5.9 mmol) was added dropwise to a solution of (R)-2-chloro-1-(2,3-difluorophenyl)ethan-1-ol (380 mg, 1.97 mmol) in iPrOH (4 mL) at 0° C. The mixture was diluted with Et₂O and the layers separated. The aq phase was extracted with Et₂O and the combined organic phases dried (Na₂SO₄), filtered and carefully concentrated. The product is volatile and the material was a ~1:1 mixture of the sub-title compound and iPrOH, and was used in the next step without further purification.

(e) (R)-2-(tert-Butylamino)-1-(2,3-difluorophenyl)ethan-1-ol

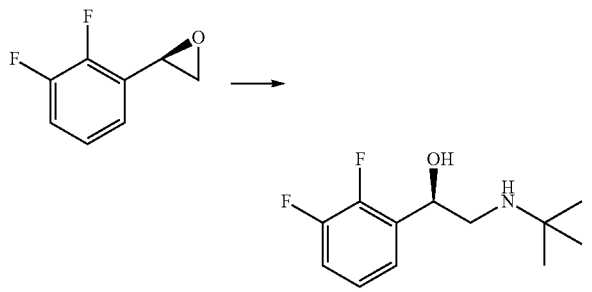

A mixture of (R)-2-(2,3-difluorophenyl)oxirane (200 mg, 1.28 mmol, containing iPrOH) and tert-butylamine (0.30 mL, 2.8 mmol) was stirred at 70° C. for 16 h, cooled and concentrated. The residue was treated with Et₂O/pentane (3+10 mL) at −20° C. and the solids collected and washed with cold Et₂O/pentane to give the title compound (135 mg, 0.59 mmol, 46%, ee=88%).

1H NMR (400 MHz, CDCl₃): δ 7.35-7.28 (m, 1H), 7.12-7.00 (m, 2H), 4.91 (dd, J=8.4, 3.7 Hz, 1H), 3.00 (ddd, J=12.0, 3.7, 1.1 Hz, 1H), 3.0-2.0 (br s 2H), 2.55 (ddd, J=12.1, 8.4, 0.7 Hz, 1H), 1.11 (s, 9H).

Example 16: (R)-2-(Butylamino)-1-(2,3-difluorophenyl)ethan-1-ol

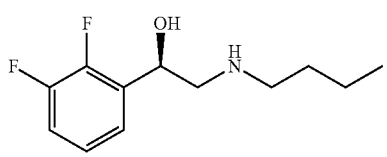 [SMILES: CCCCNC[C@H](O)c1cccc(F)c1F]

A mixture of (R)-2-(2,3-difluorophenyl)oxirane (200 mg, 1.28 mmol, containing iPrOH) and n-butylamine (2.5 mL, 25.6 mmol) was heated under microwave irradiation at 100° C. for 1 h The residue was concentrated and purified by chromatography to give the title compound (220 mg, 0.96 mmol, 75%).

¹H NMR (400 MHz, CDCl₃): δ 7.34-7.27 (m, 1H), 7.12-7.00 (m, 2H), 5.01 (dd, J=8.8, 3.5 Hz, 1H), 3.03-2.92 (m, 1H), 2.90-2.40 (br s, 2H), 2.74-2.57 (m, 3H), 1.54-1.41 (m, 2H), 1.41-1.27 (m, 2H), 0.91 (t, J=7.3 Hz, 3H).

Example 17: (R)-2-(tert-Butylamino)-1-(2-fluorophenyl)ethan-1-ol

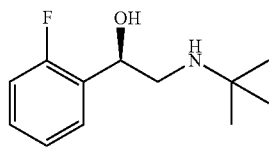

The title compound was prepared in accordance with the procedure in Example 15, Step (f), from (R)-2-(2-fluorophenyl)oxirane and tert-butylamine.

¹H NMR (300 MHz, CDCl₃): δ 7.56 (m, 1H), 7.19-7.28 (m, 1H), 7.16 (m, 1H), 6.97-7.05 (ddd, J=10.5, 8.1, 1.3 Hz, 1H), 4.92 (dd, J=8.5, 3.8 Hz, 1H), 3.00 (ddd, J=11.9, 3.8, 0.9 Hz, 1H), 2.57 (dd, J=11.7, 8.5 Hz, 1H), 1.85-2.57 (bs, 2H), 1.12 (s, 9H)

Example 18: (R)-2-(Butylamino)-1-(2-fluorophenyl)ethan-1-ol

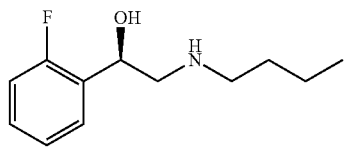

The title compound was prepared in accordance with the procedure in Example 16 from (R)-2-(2-fluorophenyl)oxirane and n-butylamine.

¹H NMR (300 MHz, CDCl₃): δ 7.60-7.51 (m, 1H), 7.29-7.20 (m, 1H), 7.19-7.12 (m, 1H), 7.00 (ddd, J=10.6, 8.1, 1.3 Hz, 1H), 5.02 (dd, J=8.8, 3.6 Hz, 1H), 2.99 (ddd, J=12.2, 3.6, 1.1 Hz, 1H), 2.80-2.54 (m, 3H), 2.52-2.09 (bs, 2H), 1.54-1.42 (m, 2H), 1.42-1.30 (m, 2H), 0.92 (t, J=7.2 Hz, 3H).

Example 19: (R)-2-(2-(tert-Butylamino)-1-hydroxyethyl)-5-fluorophenol acetate

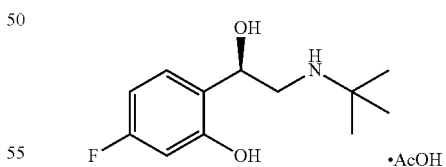

(a) 1-(2-(Benzyloxy)-4-fluorophenyl)ethan-1-one

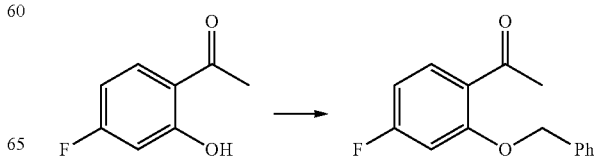

A mixture of 4-fluoro-2-hydroxyacetophenone (319 mg, 2.07 mmol), benzylbromide (0.29 mL, 2.48 mmol), K₂CO₃ (572 mg, 4.14 mmol) and acetone (12 mL) was stirred at rt for 24 h and filtered. The filtrate was concentrated and the residue purified by chromatography to give the sub-title compound (501 mg, 2.05 mmol, 99%).

(b) 1-(2-(Benzyloxy)-4-fluorophenyl)-2-bromoethan-1-one

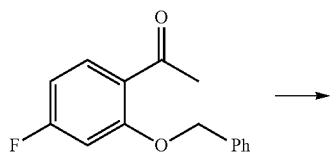

Bromine (0.12 mL, 2.30 mmol) was added in portions to a mixture of 1-(2-(benzyloxy)-4-fluorophenyl)ethan-1-one (562 mg, 2.30 mmol) in Et₂O (20 mL) at rt. After 30 min another portion of bromine (0.06 mL, 1.15 mmol) was added and the mixture stirred at rt for 90 min. The mixture was concentrated and THF (5 mL) was added. The mixture was cooled in an ice-bath and a mixture of diethylphosphite (0.30 mL, 2.30 mmol) and Et₃N (0.32 mL, 2.30 mmol) was added. The ice-bath was removed and the mixture stirred at rt for 60 min. Ice was added to the mixture, which was left to stir overnight. The mixture was diluted with CH₂Cl₂ and the phases separated. The aq phase was extracted with CH₂Cl₂ and the combined organic phases dried (Na₂SO₄), filtered and concentrated. The residue was purified by chromatography to give the sub-title compound (700 mg, 2.17 mmol, 94%).

(c) (R)-1-(2-(Benzyloxy)-4-fluorophenyl)-2-bromoethan-1-ol

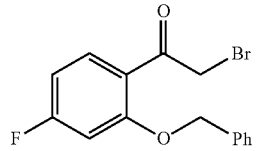

The sub-title compound was prepared from 1-(2-(benzyloxy)-4-fluorophenyl)-2-bromoethan-1-one in accordance with the procedure in Example 5, Step (a).

(d) (R)-2-(2-(Benzyloxy)-4-fluorophenyl)oxirane

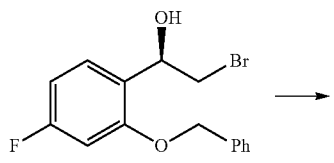

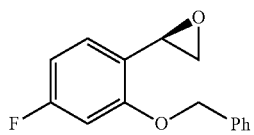

The sub-title compound was prepared from (R)-1-(2-(benzyloxy)-4-fluorophenyl)-2-bromoethan-1-ol in accordance with the procedure in Example 5, Step (b).

(e) (R)-1-(2-(Benzyloxy)-4-fluorophenyl)-2-(tert-butylamino)ethan-1-ol

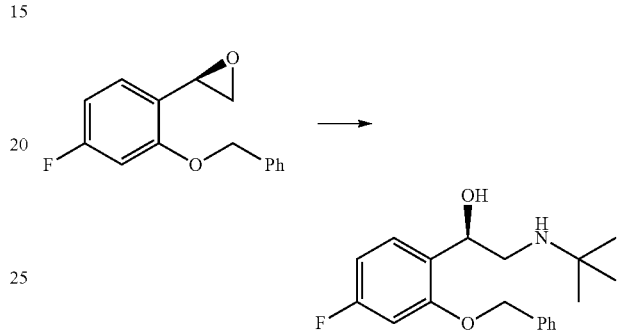

A mixture of (R)-2-(2-(benzyloxy)-4-fluorophenyl)oxirane (190 mg, 0.78 mmol), n-butyl-amine (0.180 mL, 1.71 mmol) and MeOH (0.6 mL) was stirred at 70° C. for 3 h. The mixture was concentrated and the residue purified by chromatography to give the sub-title compound (135 mg, 0.42 mmol, 55%).

(f) (R)-2-(2-(tert-Butylamino)-1-hydroxyethyl)-5-fluorophenol acetate

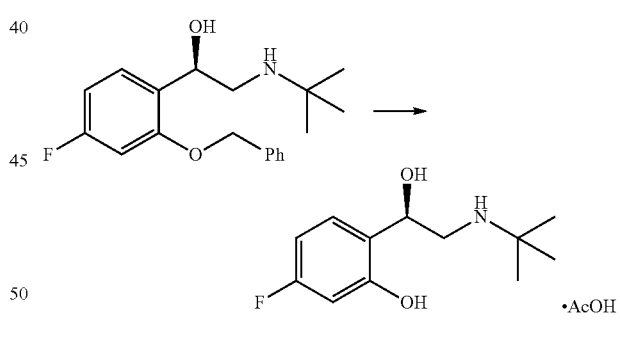

A mixture of (R)-1-(2-(benzyloxy)-4-fluorophenyl)-2-(tert-butylamino)ethan-1-ol (157 mg, 0.49 mmol), Pd—C (10%, 52.6 mg, 0.05 mmol) and AcOH (4 mL) was hydrogenated at 6 bar for 2 h. The mixture was filtered through Celite, concentrated and purified by chromatography. The material was dissolved in AcOH (1%) in MeOH and Et₂O was added. The mixture was kept at −20° C. for 2 d and the solids were collected and washed with Et₂O to give the title compound (60 mg, 0.21 mmol, 42%).

¹H NMR (400 MHz, D₂O): δ 7.40 (dd, J=8.6, 6.7 Hz, 1H), 6.84-6.65 (m, 2H), 5.21 (dd, J=9.4, 3.2 Hz, 1H), 3.37 (dd, J=12.8, 3.2 Hz, 1H), 3.25 (dd, J=12.7, 9.4 Hz, 1H), 1.94 (s, OH), 1.41 (s, 9H).

Example 20: (R)-2-(2-(Butylamino)-1-hydroxy-ethyl)-5-fluorophenol acetate

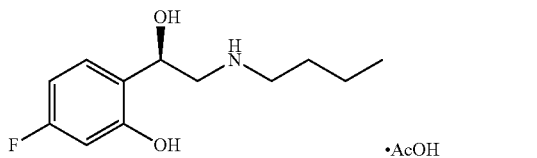 [SMILES: "·AcOH" ; CCCCNC[C@H](O)c1ccc(F)cc1O]

(a) (R)-(1-(2-(Benzyloxy)-4-fluorophenyl)-2-bromoethoxy)triethylsilane

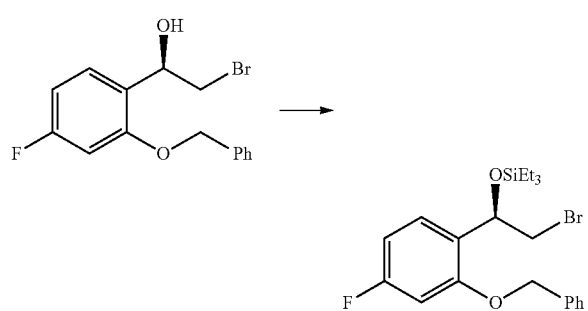

Chlorotriethylsilane (0.12 mL, 0.73 mmol) was added in one portion to a mixture of (R)-1-(2-(benzyloxy)-4-fluorophenyl)-2-bromoethan-1-ol (215 mg, 0.66 mmol) (See Example 19, Step (c)), imidazole (58.5 mg (0.86 mmol) and DMF (5 mL) at 5° C. The temperature was allowed to reach 15° C. and the mixture was stirred at that temperature for 1 h. The mixture was diluted with petroleum ether, washed three times with H₂O, dried (Na₂SO₄), filtered and concentrated to give the sub-title compound (270 mg, 0.61 mmol, 93%).

(b) (R)—N-(2-(2-(benzyloxy)-4-fluorophenyl)-2-((triethylsilyl)oxy)ethyl) butan-1-amine

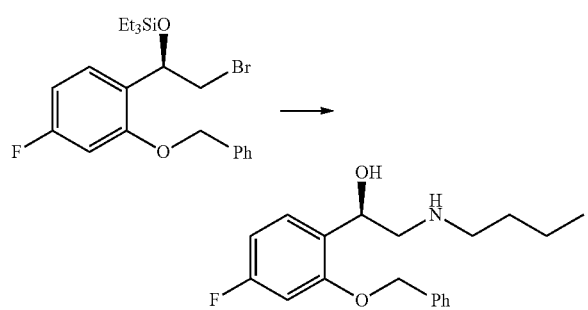

A mixture of (R)-(1-(2-(benzyloxy)-4-fluorophenyl)-2-bromoethoxy)triethylsilane (270 mg, 0.61 mmol), n-butylamine (0.30 mL, 3.07 mmol) and dioxane (2 mL) was heated at 80° C. for 16 h. Another portion of n-butylamine (0.30 mL, 3.07 mmol) was added and the mixture was heated at 105° C. for 48 h. The mixture was allowed to cool and H₂O and Et₂O was added. The organic layer was collected and washed three times with NH₄Cl (aq, sat), NaHCO₃ (aq, sat) and brine, dried (Na₂SO₄), filtered and concentrated. The residue was dissolved in THF (3 mL) and tributylammoniumfluoride (1 M in THF, 0.74 mL, 0.74 mmol) was added dropwise at 5° C. The mixture was stirred at 50° C. for 20 min, allowed to cool and H₂O and Et₂O was added. The organic layer was collected and washed with H₂O (aq, sat) and brine, dried (Na₂SO₄), filtered and concentrated. The residue was purified by chromatography to give the sub-title compound (94 mg, 0.30 mmol, 48%).

(c) (R)-2-(2-(Butylamino)-1-hydroxyethyl)-5-fluorophenol acetate

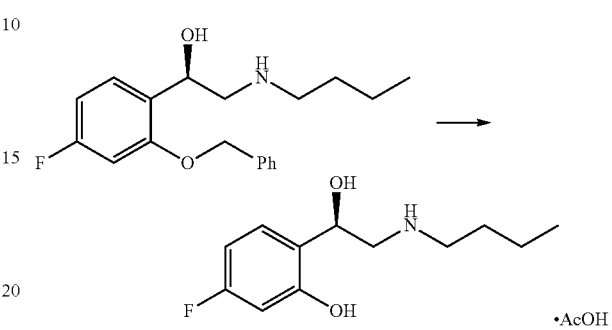

The title compound was prepared from (R)-1-(2-(benzyloxy)-4-fluorophenyl)-2-(butylamino)ethan-1-ol in accordance with the procedure in Example 19 Step (f).

¹H NMR (400 MHz, D₂O): δ 7.40 (dd, J=8.6, 6.7 Hz, 1H), 6.80-6.68 (m, 2H), 5.26 (dd, J=8.7, 3.9 Hz, 1H), 3.38 (dd, J=13.0, 4.0 Hz, 1H), 3.32 (dd, J=12.9, 8.7 Hz, 1H), 3.17-3.09 (m, 2H), 1.94 (s, 3H), 1.71 (tt, J=7.9, 6.5 Hz, 2H), 1.41 (h, J=7.4 Hz, 2H), 0.95 (t, J=7.4 Hz, 3H).

Example 21: (R)-1-(3-fluorophenyl)-2-((1-methylcyclobutyl)amino) ethan-1-ol

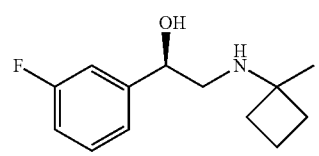 [SMILES: CC1(NC[C@H](O)c2cccc(F)c2)CCC1]

A mixture of (R)-2-(2-fluorophenyl)oxirane (130 mg, 0.94 mmol), (1-metylcyclobutyl)amine hydrochloride (298 mg, 2.45 mmol), DIPEA (0.33 mL, 1.88 mmol) and iPrOH (0.5 mL) was stirred at 70° C. for 3 h, cooled and poured into NaHCO₃ (aq., sat). The mixture was extracted with EtOAc and the combined extracts were dried (Na₂CO₃) and concentrated. The residue was purified by chromatography to give the title compound (60 mg, 0.27 mmol, 29%).

¹H NMR (400 MHz, CDCl₃): δ 7.30 (td, J=8.1, 5.9 Hz, 1H), 7.15-7.09 (m, 2H), 6.99-6.92 (m, 1H), 4.66 (dd, J=8.7, 3.6 Hz, 1H), 2.90 (dd, J=12.1, 3.7 Hz, 1H), 2.56 (dd, J=12.1, 8.7 Hz, 1H), 2.5-2.0 (br s, 2H), 2.03-1.90 (m, 2H), 1.87-1.69 (m, 4H), 1.28 (s, 3H).

Example 22: (R)-1-(3-fluorophenyl)-2-((1-methylcyclopropyl)amino) ethan-1-ol

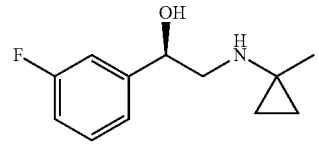

The title compound was prepared according to Example 21 from (R)-2-(2-fluorophenyl)-oxirane and (1-metylcyclopropyl)amine hydrochloride.

¹H NMR (300 MHz, CDCl₃): δ 77.35-7.27 (m, 1H), 7.17-7.06 (m, 2H), 6.95 (td, J=8.5, 2.6 Hz, 1H), 4.60 (dd, J=8.7, 3.6 Hz, 1H), 3.08 (dd, J=12.1, 3.7 Hz, 1H), 2.67 (dd, J=12.1, 8.7 Hz, 1H), 2.6-2.0 (br s, 2H), 1.25 (s, 3H), 0.70-0.53 (m, 2H), 0.48-0.33 (m, 2H).

Example 23: (R)-5-(2-(tert-Butylamino)-1-hydroxyethyl)-2-fluorophenol acetate

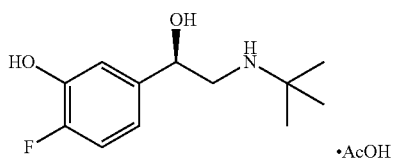 [SMILES: "·AcOH" ; CC(C)(C)NC[C@H](O)c1ccc(F)c(O)c1]

¹H NMR (400 MHz, D₂O): δ 7.25-7.14 (m, 1H), 7.12-7.01 (m, 1H), 7.01-6.89 (m, 1H), 4.92 (dd, J=3.2, 9.8 Hz, 1H), 3.33-3.14 (m, 2H), 1.92 (s, 3H), 1.40 (s, 9H).

Example 24: (R)-5-(2-(Butylamino)-1-hydroxyethyl)-2-fluorophenol acetate

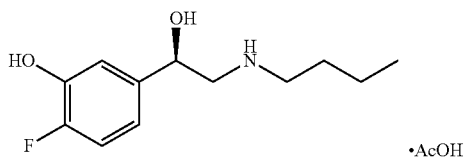 [SMILES: "·AcOH" ; CCCCNC[C@H](O)c1ccc(F)c(O)c1]

¹H NMR (400 MHz, D₂O): δ 7.25-7.13 (m, 1H), 7.10-7.01 (m, 1H), 6.98-6.89 (m, 1H), 4.98 (dd, J=4.0, 9.0 Hz, 1H), 3.37-3.20 (m, 2H), 3.19-3.03 (m, 2H), 1.92 (s, 3H), 1.75-1.61 (m, 2H), 1.47-1.31 (m, 2H), 0.93 (t, J=7.4 Hz, 3H)

Example 25: (R)-3-(2-(tert-Butylamino)-1-hydroxyethyl)-2-fluorophenol

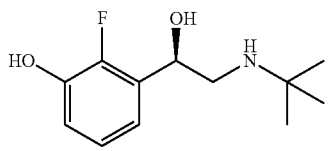 [SMILES: CC(C)(C)NC[C@H](O)c1cccc(O)c1F]

(a) 1-(3-(Benzyloxy)-2-fluorophenyl)ethan-1-one

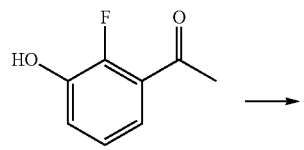

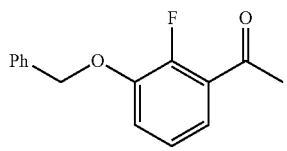

The sub-title compound was prepared from 4-fluoro-2-hydroxyacetophenone and benzylbromide in accordance with the procedure in Example 20, Step (a).

(b) 1-(3-(Benzyloxy)-2-fluorophenyl)-2-bromoethan-1-one

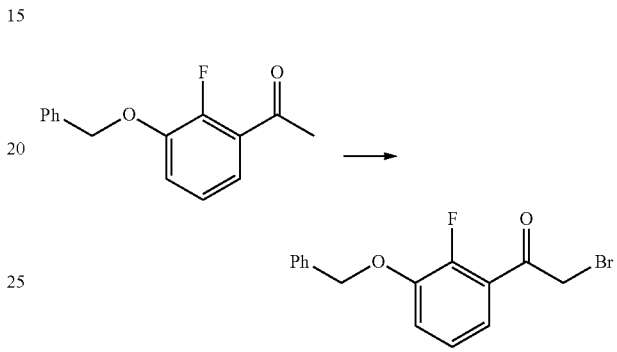

A mixture of bromine (0.13 mL, 2.45 mmol) and Et₂O (2 mL) was added dropwise to a mixture of 1-(3-(benzyloxy)-2-fluorophenyl)ethan-1-one (599 mg, 2.45 mmol) and Et₂O (18 mL) at rt. After 10 min the mixture was washed with NaHSO₄ (aq., sat) and brine and dried over Na₂SO₄ and concentrated. The residue was purified by chromatography to give the sub-title compound (600 mg, 1.86 mmol, 76%).

(c) (R)-1-(3-(Benzyloxy)-2-fluorophenyl)-2-bromoethan-1-ol

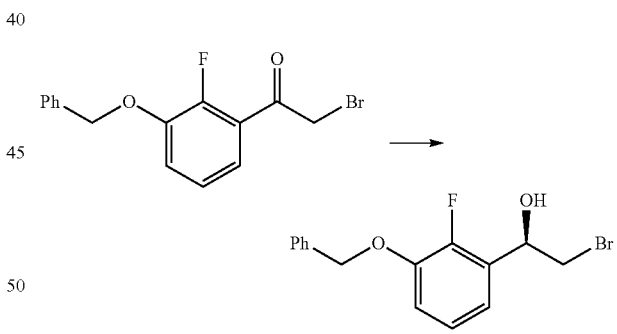

The sub-title compound was prepared from 1-(3-(benzyloxy)-2-fluorophenyl)-2-bromoethan-1-one e in accordance with the procedure in Example 5, Step (a).

(d) (R)-1-(3-(Benzyloxy)-2-fluorophenyl)-2-(tert-butylamino)ethan-1-ol

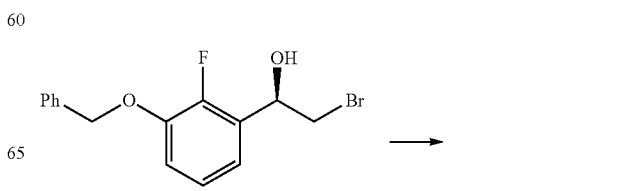

-continued

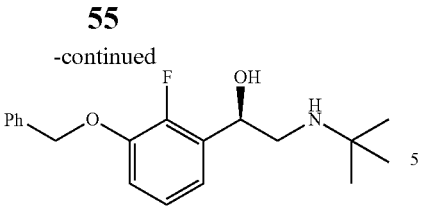

NaOH (18.45 mg, 0.46 mmol) was added to a mixture of (R)-1-(3-(benzyloxy)-2-fluorophenyl)-2-bromoethan-1-ol (150 mg, 0.46 mmol), tert-butylamine (0.49 mL, 4.61 mmol) and MeOH (0.2 mL) at rt. The mixture was heated at 70° C. for 16 h, cooled to rt, diluted with EtOAc, washed with water, dried over Na₂SO₄ and concentrated. The residue was purified by chromatography to give the sub-title compound (120 mg, 0.38 mmol, 82%).

(e) (R)-3-(2-(tert-Butylamino)-1-hydroxyethyl)-2-fluorophenol

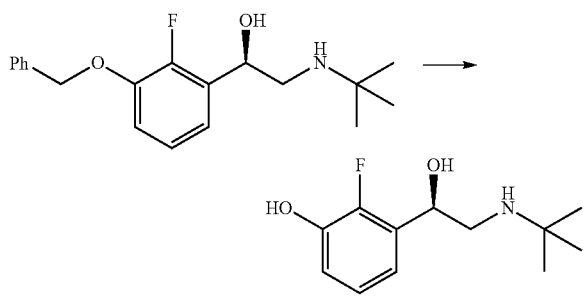

Et₃SiH (0.60 mL, 3.78 mmol) was added dropwise to a mixture of (R)-1-(3-(benzyloxy)-2-fluorophenyl)-2-(tert-butylamino)ethan-1-ol (120 mg, 0.38 mmol), Pd—C(10%, 80.5 mg, 0.08 mmol) and MeOH (1 mL) at rt. The mixture was stirred at rt for 10 min, filtered through Celite, concentrated and purified by chromatography. The material was triturated with Et₂O to give the title compound (56 mg, 0.25 mmol, 65%).

¹H NMR (400 MHz, CD₃OD): δ 7.04-6.95 (m, 2H), 6.91-6.84 (m, 1H), 5.14 (dd, J=9.7, 3.3 Hz, 1H), 3.00 (ddd, J=12.0, 3.3, 0.6 Hz, 1H), 2.91 (dd, J=12.0, 9.7 Hz, 1H), 1.28 (s, 9H).

Example 26: (R)-3-(2-(Butylamino)-1-hydroxyethyl)-2-fluorophenol

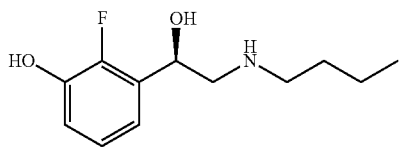 [SMILES: CCCCNC[C@H](O)c1cccc(O)c1F]

(a) (R)-1-(3-(Benzyloxy)-2-fluorophenyl)-2-(butylamino)ethan-1-ol

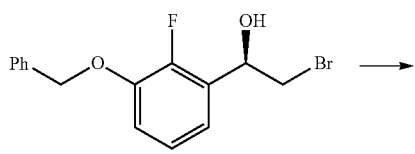

-continued

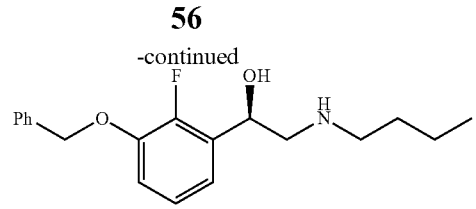

The sub-title compound was prepared from (R)-1-(3-(benzyloxy)-2-fluorophenyl)-2-bromoethan-1-ol in accordance with the procedure in Example 25, Step (d).

(b) (R)-3-(2-(Butylamino)-1-hydroxyethyl)-2-fluorophenol

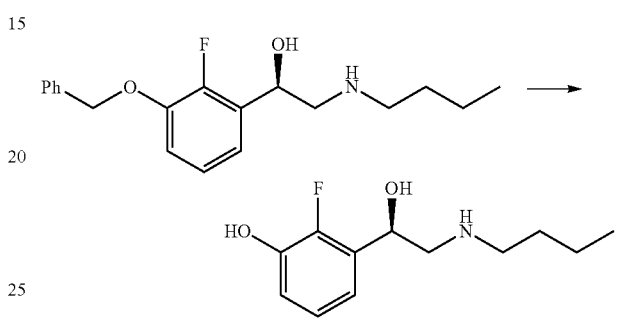

The title compound was prepared from (R)-1-(3-(benzyloxy)-2-fluorophenyl)-2-(butylamino)ethan-1-ol in accordance with the procedure in Example 25, Step (e)

¹H NMR (400 MHz, CDCl₃): δ 6.96-6.88 (m, 2H), 6.86-6.81 (m, 1H), 5.07 (dd, J=8.9, 3.6 Hz, 1H), 4.43 (br s, 3H), 2.92 (dd, J=12.1, 3.6 Hz, 1H), 2.78 (dd, J=12.1, 8.8 Hz, 1H), 2.72-7.59 (m, 2H), 1.54-1.40 (m, 2H), 1.36-1.27 (m, 2H), 0.88 (t, J=7.3 Hz, 3H).

Example 27: (R)-1-(3-Amino-2-fluorophenyl)-2-(tert-butylamino)ethan-1-ol

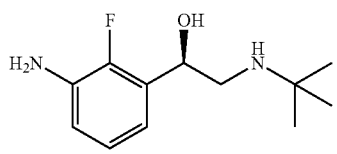 [SMILES: CC(C)(C)NC[C@H](O)c1cccc(N)c1F]

(a) 2-Fluoro-3-isobutyramidobenzoic acid

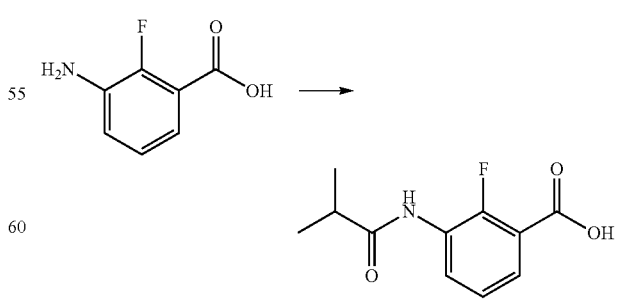

A mixture of 3-amino-2-fluorobenzoic acid (2.00 g; 12.9 mmol), isobutyric anhydride (4.3 mL, 25.8 mmol) and CH₂Cl₂ was heated at 50° C. for 2 h. The mixture was allowed to cool and concentrated. Purification of the residue by chromatography gave the sub-title compound (1.24 g, 5.51 mmol, 43%).

(b) N-(3-(2-Bromoacetyl)-2-fluorophenyl)isobutyramide

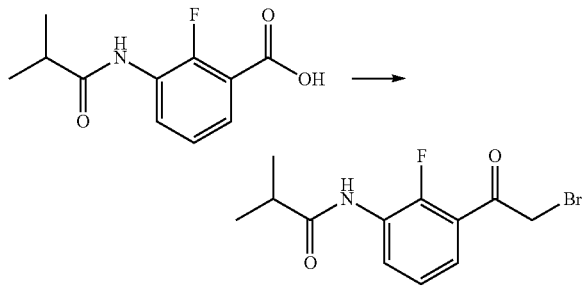

A mixture of 2-fluoro-3-isobutyramidobenzoic acid (300 mg, 1.33 mmol), SOCl$_2$ (1.9 mL) and dioxane (3 mL) was heated at 50° C. for 12 h, concentrated and dried in vacuo. The residue was dissolved in CH$_2$Cl$_2$ (15 mL) and trimethylsilyl diazomethane (1.33 mL, 2.66 mmol) was added dropwise at 0° C. The mixture was stirred at rt for 2 h and cooled to 0° C. HBr (33% in AcOH, 0.91 mL) was added dropwise. The mixture was stirred at 0° C. for 30 min and at rt for 2 h. NaHCO$_3$ (aq, sat) was added until the pH was ~7. Purification of the residue by chromatography gave the sub-title compound (0.22 mg, 0.73 mmol, 55%).

(c) (R)—N-(3-(2-bromo-1-hydroxyethyl)-2-fluorophenyl)isobutyramide

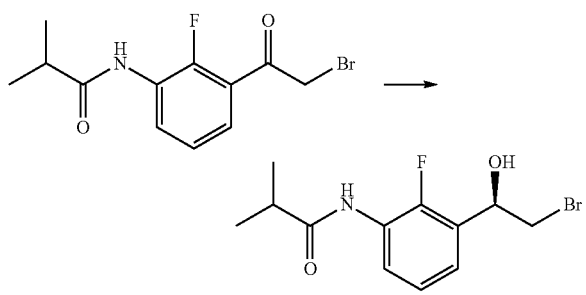

The sub-title compound was prepared from N-(3-(2-Bromoacetyl)-2-fluorophenyl)-isobutyramide in accordance with the procedure in Example 5, Step (a).

(d) (R)—N-(3-(2-(tert-butylamino)-1-hydroxyethyl)-2-fluorophenyl)isobutyramide

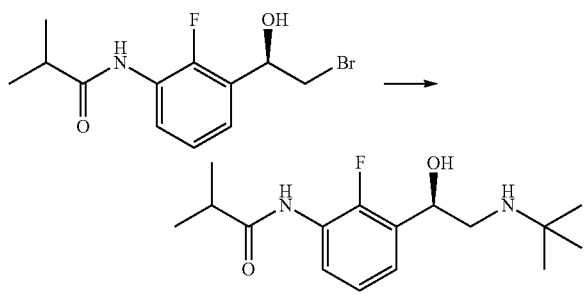

A mixture of (R)—N-(3-(2-bromo-1-hydroxyethyl)-2-fluorophenyl)isobutyramide (240 mg, 0.79 mmol), tert-butylamine (0.83 mL, 7.89 mmol), NaOH (31.6 mg, 0.79 mmol) and iPrOH (0.60 mL, 7.89 mmol) was heated at 65° C. for 3 h, cooled to rt, diluted with EtOAc, washed with water, dried over Na$_2$SO$_4$ and concentrated. The residue was purified by chromatography to give the sub-title compound (180 mg, 0.61 mmol, 77%).

(e) (R)-1-(3-Amino-2-fluorophenyl)-2-(butylamino)ethan-1-ol dihydrochloride

A mixture of (R)—N-(3-(2-(tert-butylamino)-1-hydroxyethyl)-2-fluorophenyl)isobutyramide (55 mg, 0.19 mmol) and HCl (1 M, aq, 1 mL) was heated at 85° C. for 3 h, concentrated and dried to give the title compound (50 mg, 0.17 mmol, 90%), ee=94%.

$^1$H NMR (400 MHz, CD$_3$OD): δ 6.94 (td, J=7.8, 1.0 Hz, 1H), 6.81 (dddd, J=14.7, 9.4, 7.2, 1.8 Hz, 2H), 5.05 (t, J=6.4 Hz, 1H), 2.78 (d, J=6.4 Hz, 2H), 1.17 (s, 9H).

Example 28: (R)-1-(3-Amino-2-fluorophenyl)-2-(butylamino)ethan-1-ol dihydrochloride

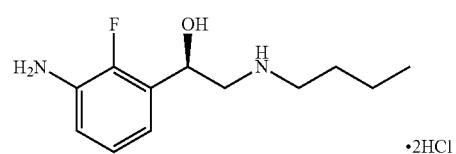 [SMILES: CCCCNC[C@H](O)c1cccc(N)c1F]

The title compound was prepared in accordance with the procedures in Example 27, using n-butylamine and MeOH in Step (d).

$^1$H NMR (400 MHz, D$_2$O): δ 7.62 (td, J=7.4, 6.7, 1.7 Hz, 1H), 7.49 (td, J=7.8, 1.7 Hz, 1H), 7.40 (t, J=7.9 Hz, 1H), 5.39 (dd, J=9.4, 3.6 Hz, 1H), 3.42 (dd, J=13.2, 3.8 Hz, 1H), 3.36 (dd, J=13.2, 9.5 Hz, 1H), 3.21-3.12 (m, 2H), 1.72 (tt, J=7.9, 6.5 Hz, 2H), 1.42 (h, J=7.4 Hz, 2H), 0.95 (t, J=7.4 Hz, 3H).

Example 29: (R)-1-(3-Fluorophenyl)-2-(neopentylamino)ethan-1-ol hydrochloride

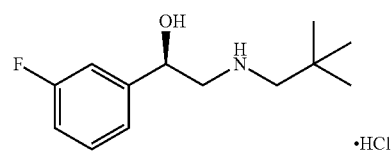 [SMILES: CC(C)(C)CNC[C@H](O)c1cccc(F)c1 ; Cl]

A mixture of (R)-2-(3-fluorophenyl)oxirane (60 mg, 0.43 mmol) and neopentylamine (379 mg, 4.34 mmol) was heated at 75° C. overnight and concentrated. The residue was dissolved in Et$_2$O (5 mL) and HCl (2 M in Et$_2$O, 0.17 mL, 0.35 mmol) was added. The solids were collected and dried to give the title compound (92 mg, 0.35 mmol, 81%).

$^1$H NMR (400 MHz, D$_2$O): δ 7.50-7.44 (m, 1H), 7.28-7.20 (m, 2H), 7.19-7.12 (m, 1H), 5.16 (dd, J=10.0, 3.7 Hz, 1H), 3.38 (dd, J=13.2, 3.8 Hz, 1H), 3.32 (dd, J=13.2, 10.0 Hz, 1H), 3.05, 3.00 (ABq, J$_{AB}$=12.5 Hz, 2H), 1.08 (s, 9H).

Example 30: (R)-1-(3-fluorophenyl)-2-((1-(trifluoromethyl)cyclopropyl)amino)ethan-1-ol hydrochloride

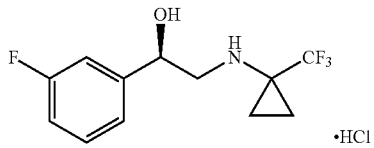 [SMILES: O[C@@H](CNC1(C(F)(F)F)CC1)c1cccc(F)c1 ; Cl]

A mixture of (R)-2-(3-fluorophenyl)oxirane (60 mg, 0.43 mmol) and 1-trifluoromethyl-1-cyclopropylamine (54 mg, 0.43 mmol) was heated at 75° C. overnight. Another portion of 1-trifluoromethyl-1-cyclopropylamine (54 mg, 0.43 mmol) and DMF (0.33 mL) was added and the heating was continued. H$_2$O (77 μL, 4.3 mmol) and 1-trifluoromethyl-1-cyclopropylamine (54 mg, 0.43 mmol) was added and heating was continued for 3 d adding portions of 1-trifluoromethyl-1-cyclopropylamine (54 mg, 0.43 mmol) each day. [The total amount of the 1-trifluoromethyl-1-cyclopropylamine was (326 mg, 2.60 mmol)]. The mixture was concentrated and dissolved in Et$_2$O (2 mL). HCl (2 M in Et$_2$O, 0.21 mL, 0.43 mmol) was added and the solids were collected and dried to give the title compound (20 mg, 67 pmol, 15%).

$^1$H NMR (400 MHz, CD$_3$OD): δ 7.45-7.39 (m, 1H), 7.28-7.20 (m, 2H), 7.12-7.05 (m, 1H), 4.99 (dd, J=10.4, 3.1 Hz, 1H), 3.47 (dd, J=12.7, 3.4 Hz, 1H), 3.33-3.25 (m, 1H, overlapping with CD$_3$OD), 1.65-1.44 (m, 4H).

Example 31: (R)-1-(3-amino-2,4-difluorophenyl)-2-(tert-butylamino)ethan-1-ol hydrochloride

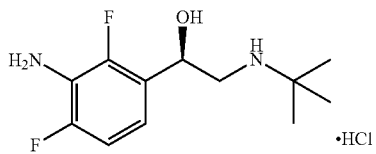 [SMILES: CC(C)(C)NC[C@H](O)c1ccc(F)c(N)c1F ; Cl]

(a) N-(2,6-difluoro-3-methylphenyl)acetamide

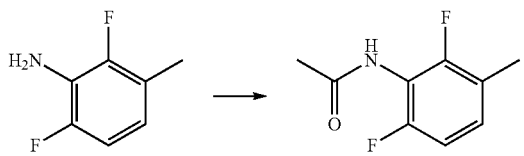

The sub-title compound was prepared from 2,6-difluoro-3-methylaniline in accordance with the procedure in Example 6, Step (a).

(b) 3-acetamido-2,4-difluorobenzoic acid

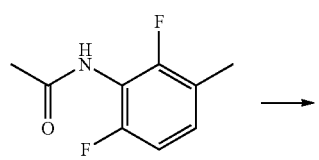

The sub-title compound was prepared from N-(2,6-difluoro-3-methylphenyl)acetamide in accordance with the procedure in Example 7, Step (b).

(c) N-(3-(2-Chloroacetyl)-2,6-difluorophenyl)acetamide

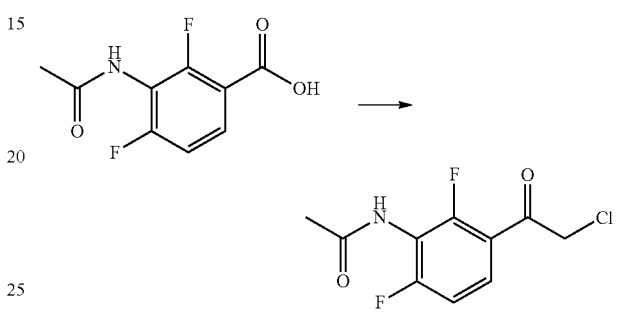

A mixture of 3-acetamido-2,4-difluorobenzoic acid (250 mg, 1.16 mmol) and SOCl$_2$ (2.6 mL) was heated at 60° C. for 4 h and allowed to cool. Toluene was added and the mixture concentrated. The procedure of adding toluene followed by concentration was repeated three times. The residue was dissolved in CH$_2$Cl$_2$ and trimethylsilyl diazomethane (1.16 mL, 2.32 mmol) was added dropwise at 0° C. The mixture was allowed to come to rt over 18 h and cooled to 0° C. HCl (4 M in dioxane, 1.45 mL, 5.81 mmol) was added dropwise. The mixture was allowed to come to rt over 1 h, diluted with EtOAc and washed with Na$_2$CO$_3$ (aq, sat), dried over MgSO$_4$ and concentrated. The residue was purified by chromatography to give the sub-title compound (198 mg, 0.80 mmol, 69%).

(d) (R)—N-(3-(2-chloro-1-hydroxyethyl)-2,6-difluorophenyl)acetamide

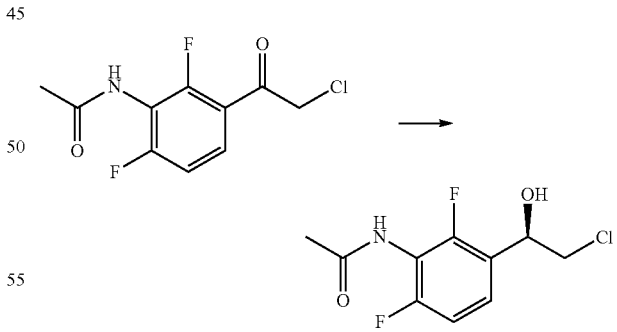

RhClCp*[(1S,2S)-p-TsNCH(C$_6$H$_5$)CH(C$_6$H$_5$)NH$_2$]/HCl.Et$_3$N (5.02 mg, 0.0065 mmol), prepared from dichloro (pentamethylcyclopentadienyl)rhodium (III) dimer, (1S, 2S)-(+)—N-(4-toluenesulphonyl)-1,2-diphenylethylene diamine and Et$_3$N as described in WO 2008/054155, was added to a mixture of N-(3-(2-chloroacetyl)-2,6-difluorophenyl)acetamide (160 mg, 0.65 mmol) in DMF (2.7 mL). Formic acid/Et$_3$N (5:2, 0.90 mL) was added and the mixture was stirred at rt for 20 min. The mixture was diluted with EtOAc, washed with H$_2$O and brine, dried (Na$_2$SO$_4$), filtered and concentrated. The residue was crystallized from CH$_2$Cl$_2$/hexane to give the sub-title compound (101 mg, 0.41 mmol, 63%, ee=97%).

(e) (R)—N-(3-(2-(tert-butylamino)-1-hydroxyethyl)-2,6-difluorophenyl)acetamide

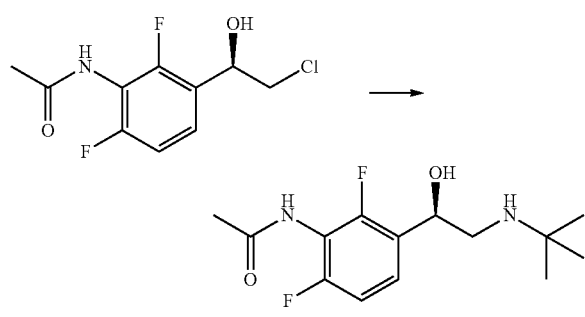

The sub-title compound was prepared from (R)—N-(3-(2-chloro-1-hydroxyethyl)-2,6-difluorophenyl)acetamide in accordance with the procedure in Example 25, Step (d).

(f) (R)-1-(3-amino-2,4-difluorophenyl)-2-(tert-butylamino)ethan-1-ol hydrochloride

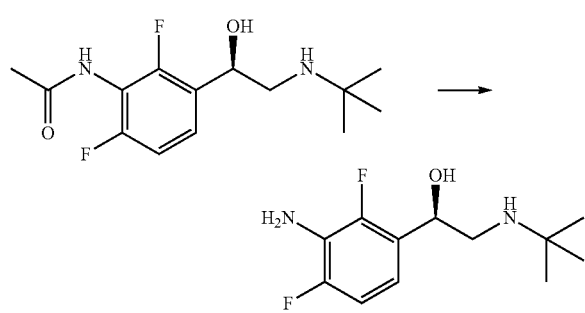

NaOH (aq, 10%, 0.52 mL) was added to of (R)—N-(3-(2-(tert-butylamino)-1-hydroxyethyl)-2,6-difluorophenyl)acetamide (52 mg, 0.18 mmol) in EtOH (0.52 mL) and the mixture was heated at 75° C. for 20 h. The EtOH was removed in vacuo and the residue extracted with CH$_2$Cl$_2$. The combined extracts were washed with water, dried over Na$_2$SO$_4$, filtered and concentrated. The residue was dissolved in Et$_2$O. HCl (2 M in Et$_2$O, 0.13 mL, 0.27 mmol) was added. The solids were collected and dried to give the title compound (32 mg, 0.11 mmol, 63%).

$^1$H NMR (400 MHz, D$_2$O): δ 7.11-7.01 (m, 2H), 5.29-5.15 (dd, J=9.6, 3.2 Hz, 1H), 3.36-3.23 (m, 2H), 1.40 (s, 9H).

Example 32: (R)-2-(tert-butylamino)-1-(3-fluoro-2-methylphenyl)ethan-1-ol

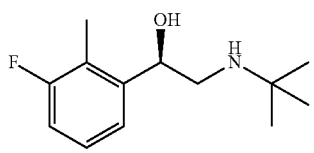

N,N'-bis[(11bS)-3,5-dihydro-3,5-dimethyl-4-oxido-4H-dinaphtho[2,1-d:1',2'-f]-[1,3,2] diazaphosphepin-4-yl]-N, N'-dimethyl-1,5-pentanediamine (15 mg, 18 pmol) and freshly distilled SiCl$_4$ (45.6 μL, 0.40 mmol) were added to 3-fluoro-2-methylbenzaldehyde (50 mg, 0.36 mmol) in CH$_2$Cl$_2$ (0.34 mL) at −78° C. A solution of tert-butylisocyanide (49.1 μL, 0.43 mmol) in CH$_2$Cl$_2$ (0.34 mL) was added over 4 h at −78° C. and the mixture was stirred at at −78° C. for 2 h. BH$_3$NH$_3$ (22.3 mg, 0.72 mmol) was added and the cooling-bath was removed and the mixture stirred for 1 h at rt and diluted with CH$_2$Cl$_2$ (2.5 mL). The mixture was added cautiously [gas evolution] to Na$_2$CO$_3$ (aq, 10%, 5 mL), stirred at rt for 30 min and filtered throug Celite. The solids were washed with CH$_2$Cl$_2$ (5 mL) and the aq phase was collected and extracted with CH$_2$Cl$_2$. The combined organic phases were dried (Na$_2$SO$_4$) and concentrated. The residue was purified by chromatography to give the title compound (53 mg, 0.24 mmol, 65%).

$^1$H NMR (400 MHz, CDCl$_3$): δ 7.32 (d, J=7.6 Hz, 1H), 7.23-7.13 (m, 1H), 6.96-6.91 (m, 1H), 4.79 (dd, J=8.8, 3.6 Hz, 1H), 2.88 (dd, J=12.4, 3.6 Hz, 1H), 2.49 (dd, J=12.0, 8.8 Hz, 1H), 2.22 (d, J=1.6 Hz, 3H), 1.11 (s, 9H).

BIOLOGICAL EXAMPLES

L6-myoblasts were grown in Dulbecco's Modified Eagle's Medium (DMEM) containing 4.5 g/l glucose supplemented with 10% fetal bovine serum, 2 mM L-Glutamine, 50 U/ml penicillin, 50 μg/ml streptomycin and 10 mM HEPES. Cells were plated at 1×10$^5$ cells per ml in 24-well plates. After reaching 90% confluence the cells were grown in medium containing 2% FBS for 7 days where upon cells differentiated into myotubes.

Biological Example 1: Glucose Uptake

Differentiated L6-myotubes were serum-starved over night in medium containing 0.5% fatty-acid free BSA and stimulated with agonist, final concentration 1×10$^{-5}$. After 1 h 40 min cells were washed with warm, glucose free medium or PBS and another portion of agonist was added to glucose free medium. After 20 min the cells were exposed to 50 nM $^3$H-2-deoxy-glucose for another 10 min before washed in ice cold glucose free medium or PBS and lysed in 0.2 M NaOH for 1 h in 60° C. Cell lysate was mixed with scintillation buffer (Emulsifier Safe, Perkin Elmer and radioactivity detected in a β-counter (Tri-Carb 2800TR, Perkin Elmer). The activity for each compound is compared to that of isoproterenol. If a compound shows activity of more than 75% of that of isoprenaline, the activity is denoted with +++, if it is between 75 and 50% it is denoted with ++; if it is between 50 and 25% it is denoted with +; if it less than 25% it is denoted with −.

Biological Example 2: Measurement of Intracellular cAMP Levels

Differentiated cells were serum-starved over night and stimulated with agonist, final concentration 1×10$^{-5}$, for 15 min in stimulation buffer (HBSS supplemented with 1% BSA, 5 mM HEPES and 1 mM IBMX, pH 7.4). The medium was then aspirated and to end the reaction 100 μL of 95% EtOH was added to each well of a 24-well plate and cells were kept in −20° C. over night. The EtOH was let to evaporate and 500 μL of lysis buffer (1% BSA, 5 mM HEPES and 0.3% Tween-20, pH 7.4) was added to each well before put in −80° C. for 30 min and then kept in −20° C. Intracellular cAMP levels were detected using an alpha screen cAMP kit (6760635D from Perkin Elmer). The activity for each compound is compared to that of isoproterenol. If a compound shows activity of more than 75% of that of isoprenaline, the activity is denoted with +++, if it is between 75 and 50% it is denoted with ++; if it is between 50 and 25% it is denoted with +; if it less than 25% it is denoted with −.

Using the assays described in Biological Examples 1 and 2 the following results were obtained.

| Compound example no. | Biological example 1 | Biological example 2 |
|---|---|---|
| 1 | ++ | − |
| 2 | ++ | − |
| 3 | + | − |
| 4 | +++ | − |
| 5 | +++ | − |
| 6 | +++ | +++ |
| 7 | +++ | − |
| 8 | + | − |
| 9 | ++ | − |
| 10 | ++ | − |
| 11 | + | − |
| 12 | +++ | − |
| 13 | ++ | − |
| 14 | +++ | − |
| 15 | +++ | + |
| 16 | +++ | − |
| 17 | ++ | − |
| 18 | +++ | − |
| 19 | ++ | − |
| 20 | +++ | − |
| 21 | +++ | + |
| 22 | +++ | − |
| 23 | +++ | ++ |
| 24 | +++ | − |
| 25 | ++ | ++ |
| 26 | +++ | + |
| 27 | +++ | + |
| 28 | ++ | − |
| 29 | + | − |
| 30 | ++ | − |
| 31 | +++ | − |
| 32 | +++ | − |

The invention claimed is:

1. A pharmaceutical composition comprising (R)-2-(tert-Butylamino)-1-(3-fluorophenyl)ethan-1-ol, having the structure:

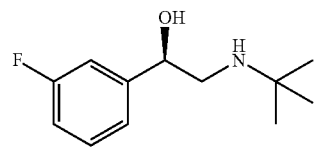

or a pharmaceutically acceptable salt thereof, and optionally one or more pharmaceutically acceptable adjuvant, diluent and/or carrier; wherein the (R)-2-(tert-Butylamino)-1-(3-fluorophenyl)ethan-1-ol is present in an enanteromeric excess of at least 90%.

2. A method of treating hyperglycaemia or a disorder characterized by hyperglycaemia comprising administering to a patient in need thereof a therapeutically effective amount of a compound as defined in claim 1, or a pharmaceutically acceptable salt thereof.

3. The method according to claim 2, wherein the hyperglycaemia or a disorder characterized by hyperglycaemia is type 2 diabetes.

4. The method according to claim 2, wherein the patient displays severe insulin resistance.

5. The method according to claim 2, wherein the disorder characterised by hyperglycaemia is selected from the group consisting of Rabson-Mendenhall syndrome, Donohue's syndrome (leprechaunism), Type A and Type B syndromes of insulin resistance, the HAIR-AN (hyperandrogenism, insulin resistance, and acanthosis *nigricans*) syndromes, pseudoacromegaly, and lipodystrophy.

\* \* \* \* \*

UNITED STATES PATENT AND TRADEMARK OFFICE
CERTIFICATE OF CORRECTION

PATENT NO. : 11,648,216 B2
APPLICATION NO. : 16/646497
DATED : May 16, 2023
INVENTOR(S) : Benjamin Pelcman et al.

It is certified that error appears in the above-identified patent and that said Letters Patent is hereby corrected as shown below:

In the Specification

At Column 45, Lines 5-18, please replace the formulas:

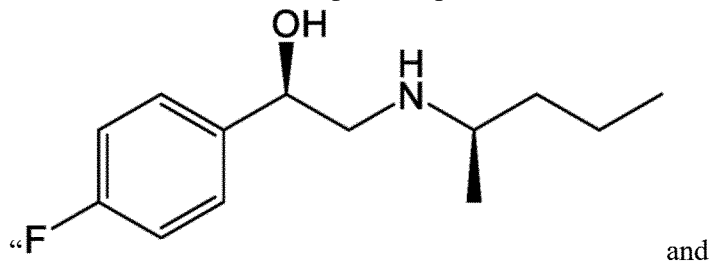

and

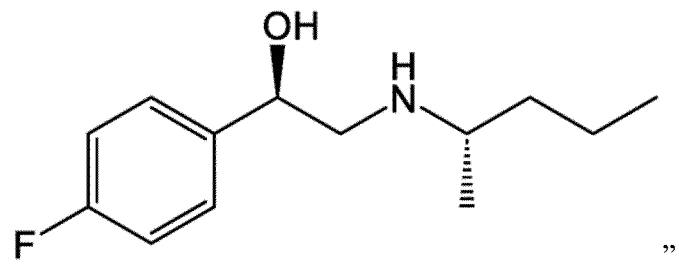

"

With the following formulas:

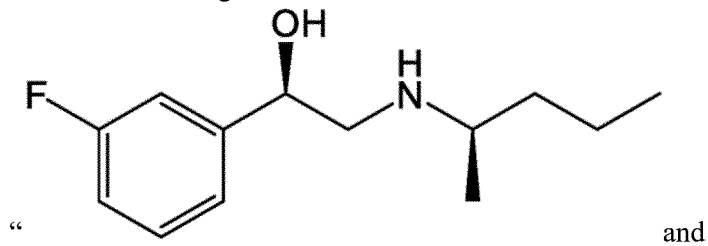

and

Signed and Sealed this
Twenty-fourth Day of September, 2024

Katherine Kelly Vidal
*Director of the United States Patent and Trademark Office*

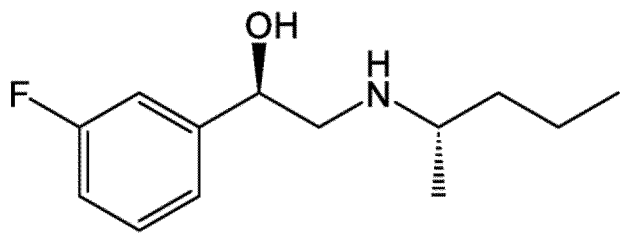 ” respectively.
At Column 29, Line 46, please replace:
"with a compound of formula"
With the following:
"with a compound of formula III".